United States Patent
Rosenberg et al.

(10) Patent No.: US 9,688,739 B2
(45) Date of Patent: Jun. 27, 2017

(54) T CELL RECEPTORS AND RELATED MATERIALS AND METHODS OF USE

(71) Applicant: The United States of America, as represented by the Secretary, Department of Health and Human Services, Washington, DC (US)

(72) Inventors: Steven A. Rosenberg, Potomac, MD (US); Richard A. Morgan, Columbia, MD (US); Timothy L. Frankel, New York, NY (US)

(73) Assignee: The United States of America, as represented by the Secretary, Department of Health and Human Services, Washington, DC (US)

(*) Notice: Subject to any disclaimer, the term of this patent is extended or adjusted under 35 U.S.C. 154(b) by 171 days.

(21) Appl. No.: 14/221,823

(22) Filed: Mar. 21, 2014

(65) Prior Publication Data

US 2014/0206620 A1 Jul. 24, 2014

Related U.S. Application Data

(62) Division of application No. 13/146,531, filed as application No. PCT/US2010/021909 on Jan. 25, 2010, now Pat. No. 8,785,601.

(60) Provisional application No. 61/147,846, filed on Jan. 28, 2009.

(51) Int. Cl.
| | |
|---|---|
| *A61K 39/395* | (2006.01) |
| *C07K 16/00* | (2006.01) |
| *C07K 14/705* | (2006.01) |
| *C07K 14/725* | (2006.01) |
| *G01N 33/574* | (2006.01) |
| *A61K 38/00* | (2006.01) |

(52) U.S. Cl.
CPC ...... *C07K 14/70503* (2013.01); *C07K 14/705* (2013.01); *C07K 14/7051* (2013.01); *G01N 33/57492* (2013.01); *A61K 38/00* (2013.01)

(58) Field of Classification Search
None
See application file for complete search history.

(56) References Cited

U.S. PATENT DOCUMENTS 5,449,752 A 9/1995 Fujii et al.

FOREIGN PATENT DOCUMENTS

| WO | WO 03/020763 A2 | 3/2003 |
| WO | WO 2007/131092 A2 | 11/2007 |
| WO | WO 2008/039818 A2 | 4/2008 |

OTHER PUBLICATIONS

U.S. Appl. No. 13/146,531, filed Sep. 28, 2011.
American Cancer Society, "What are the key Statistics About Melanoma?," *Cancer Reference Guide: Skin Cancer—Melanoma* 2008; www.cancer.org.
Boulter et al., "Stable, soluble T-cell receptor molecules for crystallization and therapeutics," *Protein Engineering*, 16 (9), 707-711 (2003).
Central Brain Tumor Registry of the United States, *Primary Brain Tumors in the United States*, Data collected 2000-2004 (2007-2008).
Choi et al., "Synthesis and Assembly of a Cholera Toxin B Subunit-Rotavirus VP7 Fusion Protein in Transgenic Potato," *Mol. Biotechnol.*, 31, 193-202 (2005).
Cohen et al., "Enhanced Antitumor Activity of Murine-Human Hybrid T-cell Receptor (TCR) in Human Lymphocytes is Associated with Improved Pairing and TCR/CD3 Stability," *Cancer Res.*, 66 (17), 8878-8886 (2006).
Cohen et al., "Enhanced Antitumor Activity of T Cells Engineered to Express T-Cell Receptors with a Second Disulfide Bond," *Cancer Res.*, 67 (8), 3898-3903 (2007).
Frankel et al., "Cloning and Modification of a T-cell Receptor Gene Targeting Tyrosinase Confers Peptide and HLA Specific Reactivity to Transduced Peripheral Blood Lymphocytes, T.L.," *J. Surgical Res.*, 151 (2), 256-257 (2009).
Hudecz, "Synthesis of Peptide Bioconjugates," *Methods Mol. Biol.*, 298, 209-223 (2005).
Johnson et al., "Gene Transfer of Tumor-Reactive TCR Confers Both High Avidity and Tumor Reactivity to Nonreactive Peripheral Blood Mononuclear Cells and Tumor-Infiltrating Lymphocytes," *J. Immunol.*, 177, 6548-6559 (2006).
Kawakami et al., "The Use of Melanosomal Proteins in the Immunotherapy of Melanoma," *J. Immunother.*, 21 (4), 237-246 (1998).
Kirin et al., "Amino Acid and Peptide Bioconjugates of Copper (II) and Zinc (II) Complexes with a Modified *N,N*-Bis(2-picolyl)amine Ligand," *Inorg Chem.*, 44 (15), 5405-5415 (2005).
Nishimura et al., "MHC Class I-restricted Recognition of a Melanoma Antigen by a Human CD4+ Tumor Infiltrating Lymphocyte," *Cancer Res.*, 59, 6230-6238 (1999).
Nishimura et al., "T-Cell Receptor Repertoire in Tumor-Infiltrating Lymphocytes. Analysis of melanoma-Specific Long-Term Lines," *J. Immunotheraphy*, 16 (2), 85-94 (1994).
Romeo et al., "Measuring Tissue-Based Biomarkers by Immunochromatography Coupled with Reverse-Phase Lysate Microarray," *Clin. Cancer Res.*, 12 (8), 2463-2467 (2006).
Roszkowski et al., "Simultaneous Generation of CD8+ and CD4+ Melanoma-Reactive T Cells by Retroviral-Mediated Transfer of a Single T-Cell Receptor," *Cancer Res.*, 65 (4), 1570-76 (2005).

(Continued)

*Primary Examiner* — Michael Pak
(74) *Attorney, Agent, or Firm* — Leydig, Voit & Mayer

(57) ABSTRACT

The invention provides T cell receptors (TCRs) having antigenic specificity for a cancer antigen, e.g., tyrosinase. Also provided are related polypeptides, proteins, nucleic acids, recombinant expression vectors, isolated host cells, populations of cells, and pharmaceutical compositions. The invention further provides a method of detecting the presence of cancer in a host and a method of treating or preventing cancer in a host using the inventive TCRs or related materials.

21 Claims, 9 Drawing Sheets

(56) References Cited

OTHER PUBLICATIONS

Roszkowski et al., "CD8-Independent Tumor Cell Recognition Is a Property of the T Cell Receptor and Not the T Cell," *J. Immunol*, 170, 2582-2589 (2003).
Topalian et al., "Tumor-Specific Cytolysis by Lymphocytes Infiltrating Human Melanomas," *J. Immunol.*, 142 (10), 3714-3725 (1989).
Zhang et al., "Antigenic Profiling of Glioma Cells to GenerateAllogeneicVaccines or Dendritic Cell-Based Therapeutics," *Clin. Cancer Res.*, 13 (2), 566-575 (2007).
PCT/US2010/021909 International Search Report dated Jun. 8, 2010.
International Preliminary Report on Patentability, Application No. PCT/US2010/021909, dated Aug. 2, 2011.
Sequences believed to be those of the T cell receptors of the T cells described in Nishimura et al., *Cancer Res.*, 59: 6230-38 (1999); Roszkowski, et al., J. Immunol, 170: 2582-89 (2003); and Roszkowski, et al., Cancer Res., 65(4): 1570-76 (2005).

SEQUENCE LISTING

```
<160> NUMBER OF SEQ ID NOS: 74

<210> SEQ ID NO 1
<211> LENGTH: 7
<212> TYPE: PRT
<213> ORGANISM: Homo sapiens

<400> SEQUENCE: 1

Asn Ile Ala Thr Asn Asp Tyr
1               5

<210> SEQ ID NO 2
<211> LENGTH: 4
<212> TYPE: PRT
<213> ORGANISM: Homo sapiens

<400> SEQUENCE: 2

Gly Tyr Lys Thr
1

<210> SEQ ID NO 3
<211> LENGTH: 14
<212> TYPE: PRT
<213> ORGANISM: Homo sapiens

<400> SEQUENCE: 3

Leu Val Ala Leu Asn Tyr Gly Gly Ser Gln Gly Asn Leu Ile
```

-continued

<210> SEQ ID NO 4
<211> LENGTH: 5
<212> TYPE: PRT
<213> ORGANISM: Homo sapiens

<400> SEQUENCE: 4

Glu Asn His Arg Tyr
1               5

<210> SEQ ID NO 5
<211> LENGTH: 6
<212> TYPE: PRT
<213> ORGANISM: Homo sapiens

<400> SEQUENCE: 5

Ser Tyr Gly Val Lys Asp
1               5

<210> SEQ ID NO 6
<211> LENGTH: 18
<212> TYPE: PRT
<213> ORGANISM: Homo sapiens

<400> SEQUENCE: 6

Ala Ile Ser Pro Thr Glu Glu Gly Gly Leu Ile Phe Pro Gly Asn Thr
1               5                   10                  15

Ile Tyr

<210> SEQ ID NO 7
<211> LENGTH: 130
<212> TYPE: PRT
<213> ORGANISM: Homo sapiens

<400> SEQUENCE: 7

Met Ala Gln Val Ala Arg Val Asn Val Phe Leu Thr Leu Ser Thr Leu
1               5                   10                  15

Ser Leu Ala Lys Thr Thr Gln Pro Ile Ser Met Asp Ser Tyr Glu Gly
                20                  25                  30

Gln Glu Val Asn Ile Thr Cys Ser His Asn Asn Ile Ala Thr Asn Asp
            35                  40                  45

Tyr Ile Thr Trp Tyr Gln Gln Phe Pro Ser Gln Gly Pro Arg Phe Ile
        50                  55                  60

Ile Gln Gly Tyr Lys Thr Lys Val Thr Asn Glu Val Ala Ser Leu Phe
65                  70                  75                  80

Ile Pro Ala Asp Arg Lys Ser Ser Thr Leu Ser Leu Pro Arg Val Ser
                85                  90                  95

Leu Ser Asp Thr Ala Val Tyr Tyr Cys Leu Val Ala Leu Asn Tyr Gly
            100                 105                 110

Gly Ser Gln Gly Asn Leu Ile Phe Gly Lys Gly Thr Lys Leu Ser Val
        115                 120                 125

Lys Pro
    130

<210> SEQ ID NO 8
<211> LENGTH: 138
<212> TYPE: PRT
<213> ORGANISM: Homo sapiens

<400> SEQUENCE: 8

```
Met Gly Thr Arg Leu Phe Phe Tyr Val Ala Leu Cys Leu Leu Trp Thr
  1               5                  10                  15

Gly His Met Asp Ala Gly Ile Thr Gln Ser Pro Arg His Lys Val Thr
             20                  25                  30

Glu Thr Gly Thr Pro Val Thr Leu Arg Cys His Gln Thr Glu Asn His
         35                  40                  45

Arg Tyr Met Tyr Trp Tyr Arg Gln Asp Pro Gly His Gly Leu Arg Leu
     50                  55                  60

Ile His Tyr Ser Tyr Gly Val Lys Asp Thr Asp Lys Gly Glu Val Ser
 65                  70                  75                  80

Asp Gly Tyr Ser Val Ser Arg Ser Lys Thr Asp Phe Leu Leu Thr
                 85                  90                  95

Leu Glu Ser Ala Thr Ser Ser Gln Thr Ser Val Tyr Phe Cys Ala Ile
                100                 105                 110

Ser Pro Thr Glu Glu Gly Gly Leu Ile Phe Pro Gly Asn Thr Ile Tyr
            115                 120                 125

Phe Gly Glu Gly Ser Trp Leu Thr Val Val
        130                 135

<210> SEQ ID NO 9
<211> LENGTH: 141
<212> TYPE: PRT
<213> ORGANISM: Homo sapiens

<400> SEQUENCE: 9

Asn Ile Gln Asn Pro Asp Pro Ala Val Tyr Gln Leu Arg Asp Ser Lys
  1               5                  10                  15

Ser Ser Asp Lys Ser Val Cys Leu Phe Thr Asp Phe Asp Ser Gln Thr
             20                  25                  30

Asn Val Ser Gln Ser Lys Asp Ser Asp Val Tyr Ile Thr Asp Lys Thr
         35                  40                  45

Val Leu Asp Met Arg Ser Met Asp Phe Lys Ser Asn Ser Ala Val Ala
     50                  55                  60

Trp Ser Asn Lys Ser Asp Phe Ala Cys Ala Asn Val Phe Asn Asn Ser
 65                  70                  75                  80

Ile Ile Pro Glu Asp Thr Phe Phe Pro Ser Pro Glu Ser Ser Cys Asp
                 85                  90                  95

Val Lys Leu Val Glu Lys Ser Phe Glu Thr Asp Thr Asn Leu Asn Phe
                100                 105                 110

Gln Asn Leu Ser Val Ile Gly Phe Arg Ile Leu Leu Leu Lys Val Ala
            115                 120                 125

Gly Phe Asn Leu Leu Met Thr Leu Arg Leu Trp Ser Ser
        130                 135                 140

<210> SEQ ID NO 10
<211> LENGTH: 177
<212> TYPE: PRT
<213> ORGANISM: Homo sapiens

<400> SEQUENCE: 10

Glu Asp Leu Asn Lys Val Phe Pro Pro Glu Val Ala Val Phe Glu Pro
  1               5                  10                  15

Ser Glu Ala Glu Ile Ser His Thr Gln Lys Ala Thr Leu Val Cys Leu
             20                  25                  30

Ala Thr Gly Phe Phe Pro Asp His Val Glu Leu Ser Trp Trp Val Asn
         35                  40                  45
```

```
Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
            115                 120                 125

Ala Asp Cys Gly Phe Thr Ser Val Ser Tyr Gln Gln Gly Val Leu Ser
            130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe

<210> SEQ ID NO 11
<211> LENGTH: 271
<212> TYPE: PRT
<213> ORGANISM: Homo sapiens

<400> SEQUENCE: 11

Met Ala Gln Val Ala Arg Val Asn Val Phe Leu Thr Leu Ser Thr Leu
1               5                   10                  15

Ser Leu Ala Lys Thr Thr Gln Pro Ile Ser Met Asp Ser Tyr Glu Gly
                20                  25                  30

Gln Glu Val Asn Ile Thr Cys Ser His Asn Asn Ile Ala Thr Asn Asp
            35                  40                  45

Tyr Ile Thr Trp Tyr Gln Gln Phe Pro Ser Gln Gly Pro Arg Phe Ile
    50                  55                  60

Ile Gln Gly Tyr Lys Thr Lys Val Thr Asn Glu Val Ala Ser Leu Phe
65                  70                  75                  80

Ile Pro Ala Asp Arg Lys Ser Ser Thr Leu Ser Leu Pro Arg Val Ser
                85                  90                  95

Leu Ser Asp Thr Ala Val Tyr Tyr Cys Leu Val Ala Leu Asn Tyr Gly
            100                 105                 110

Gly Ser Gln Gly Asn Leu Ile Phe Gly Lys Gly Thr Lys Leu Ser Val
            115                 120                 125

Lys Pro Asn Ile Gln Asn Pro Asp Pro Ala Val Tyr Gln Leu Arg Asp
            130                 135                 140

Ser Lys Ser Ser Asp Lys Ser Val Cys Leu Phe Thr Asp Phe Asp Ser
145                 150                 155                 160

Gln Thr Asn Val Ser Gln Ser Lys Asp Ser Asp Val Tyr Ile Thr Asp
                165                 170                 175

Lys Thr Val Leu Asp Met Arg Ser Met Asp Phe Lys Ser Asn Ser Ala
            180                 185                 190

Val Ala Trp Ser Asn Lys Ser Asp Phe Ala Cys Ala Asn Val Phe Asn
            195                 200                 205

Asn Ser Ile Ile Pro Glu Asp Thr Phe Phe Pro Ser Pro Glu Ser Ser
        210                 215                 220

Cys Asp Val Lys Leu Val Glu Lys Ser Phe Glu Thr Asp Thr Asn Leu
225                 230                 235                 240
```

```
Asn Phe Gln Asn Leu Ser Val Ile Gly Phe Arg Ile Leu Leu Leu Lys
                245                 250                 255

Val Ala Gly Phe Asn Leu Leu Met Thr Leu Arg Leu Trp Ser Ser
            260                 265                 270

<210> SEQ ID NO 12
<211> LENGTH: 315
<212> TYPE: PRT
<213> ORGANISM: Homo sapiens

<400> SEQUENCE: 12

Met Gly Thr Arg Leu Phe Phe Tyr Val Ala Leu Cys Leu Leu Trp Thr
1               5                   10                  15

Gly His Met Asp Ala Gly Ile Thr Gln Ser Pro Arg His Lys Val Thr
            20                  25                  30

Glu Thr Gly Thr Pro Val Thr Leu Arg Cys His Gln Thr Glu Asn His
        35                  40                  45

Arg Tyr Met Tyr Trp Tyr Arg Gln Asp Pro Gly His Gly Leu Arg Leu
    50                  55                  60

Ile His Tyr Ser Tyr Gly Val Lys Asp Thr Asp Lys Gly Glu Val Ser
65                  70                  75                  80

Asp Gly Tyr Ser Val Ser Arg Ser Lys Thr Glu Asp Phe Leu Leu Thr
                85                  90                  95

Leu Glu Ser Ala Thr Ser Ser Gln Thr Ser Val Tyr Phe Cys Ala Ile
            100                 105                 110

Ser Pro Thr Glu Glu Gly Gly Leu Ile Phe Pro Gly Asn Thr Ile Tyr
        115                 120                 125

Phe Gly Glu Gly Ser Trp Leu Thr Val Val Glu Asp Leu Asn Lys Val
    130                 135                 140

Phe Pro Pro Glu Val Ala Val Phe Glu Pro Ser Glu Ala Glu Ile Ser
145                 150                 155                 160

His Thr Gln Lys Ala Thr Leu Val Cys Leu Ala Thr Gly Phe Phe Pro
                165                 170                 175

Asp His Val Glu Leu Ser Trp Trp Val Asn Gly Lys Glu Val His Ser
            180                 185                 190

Gly Val Ser Thr Asp Pro Gln Pro Leu Lys Glu Gln Pro Ala Leu Asn
        195                 200                 205

Asp Ser Arg Tyr Cys Leu Ser Ser Arg Leu Arg Val Ser Ala Thr Phe
    210                 215                 220

Trp Gln Asn Pro Arg Asn His Phe Arg Cys Gln Val Gln Phe Tyr Gly
225                 230                 235                 240

Leu Ser Glu Asn Asp Glu Trp Thr Gln Asp Arg Ala Lys Pro Val Thr
                245                 250                 255

Gln Ile Val Ser Ala Glu Ala Trp Gly Arg Ala Asp Cys Gly Phe Thr
            260                 265                 270

Ser Val Ser Tyr Gln Gln Gly Val Leu Ser Ala Thr Ile Leu Tyr Glu
        275                 280                 285

Ile Leu Leu Gly Lys Ala Thr Leu Tyr Ala Val Leu Val Ser Ala Leu
    290                 295                 300

Val Leu Met Ala Met Val Lys Arg Lys Asp Phe
305                 310                 315

<210> SEQ ID NO 13
<211> LENGTH: 27
<212> TYPE: PRT
```

```
<213> ORGANISM: Artificial Sequence
<220> FEATURE:
<223> OTHER INFORMATION: Synthetic

<400> SEQUENCE: 13

Arg Ala Lys Arg Ser Gly Ser Gly Ala Thr Asn Phe Ser Leu Leu Lys
1               5                   10                  15

Gln Ala Gly Asp Val Glu Glu Asn Pro Gly Pro
            20                  25

<210> SEQ ID NO 14
<211> LENGTH: 141
<212> TYPE: PRT
<213> ORGANISM: Artificial Sequence
<220> FEATURE:
<223> OTHER INFORMATION: Synthetic

<400> SEQUENCE: 14

Asn Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Cys
        35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Val Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
    130                 135                 140

<210> SEQ ID NO 15
<211> LENGTH: 177
<212> TYPE: PRT
<213> ORGANISM: Artificial Sequence
<220> FEATURE:
<223> OTHER INFORMATION: Synthetic

<400> SEQUENCE: 15

Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
        35                  40                  45

Gly Lys Glu Val His Ser Gly Val Cys Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110
```

Arg Ala Lys Pro Val Thr Gln Ile Val Ser Ala Glu Ala Trp Gly Arg
            115                 120                 125

Ala Asp Cys Gly Phe Thr Ser Val Ser Tyr Gln Gln Gly Val Leu Ser
        130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe

<210> SEQ ID NO 16
<211> LENGTH: 271
<212> TYPE: PRT
<213> ORGANISM: Artificial Sequence
<220> FEATURE:
<223> OTHER INFORMATION: Synthetic

<400> SEQUENCE: 16

Met Ala Gln Val Ala Arg Val Asn Val Phe Leu Thr Leu Ser Thr Leu
1               5                   10                  15

Ser Leu Ala Lys Thr Thr Gln Pro Ile Ser Met Asp Ser Tyr Glu Gly
            20                  25                  30

Gln Glu Val Asn Ile Thr Cys Ser His Asn Asn Ile Ala Thr Asn Asp
        35                  40                  45

Tyr Ile Thr Trp Tyr Gln Gln Phe Pro Ser Gln Gly Pro Arg Phe Ile
    50                  55                  60

Ile Gln Gly Tyr Lys Thr Lys Val Thr Asn Glu Val Ala Ser Leu Phe
65                  70                  75                  80

Ile Pro Ala Asp Arg Lys Ser Ser Thr Leu Ser Leu Pro Arg Val Ser
                85                  90                  95

Leu Ser Asp Thr Ala Val Tyr Tyr Cys Leu Val Ala Leu Asn Tyr Gly
            100                 105                 110

Gly Ser Gln Gly Asn Leu Ile Phe Gly Lys Gly Thr Lys Leu Ser Val
        115                 120                 125

Lys Pro Asn Ile Gln Asn Pro Asp Pro Ala Val Tyr Gln Leu Arg Asp
    130                 135                 140

Ser Lys Ser Ser Asp Lys Ser Val Cys Leu Phe Thr Asp Phe Asp Ser
145                 150                 155                 160

Gln Thr Asn Val Ser Gln Ser Lys Asp Ser Asp Val Tyr Ile Thr Asp
                165                 170                 175

Lys Cys Val Leu Asp Met Arg Ser Met Asp Phe Lys Ser Asn Ser Ala
            180                 185                 190

Val Ala Trp Ser Asn Lys Ser Asp Phe Ala Cys Ala Asn Val Phe Asn
        195                 200                 205

Asn Ser Ile Ile Pro Glu Asp Thr Phe Phe Pro Ser Pro Glu Ser Ser
    210                 215                 220

Cys Asp Val Lys Leu Val Glu Lys Ser Phe Glu Thr Asp Thr Asn Leu
225                 230                 235                 240

Asn Phe Gln Asn Leu Ser Val Ile Gly Phe Arg Ile Leu Leu Leu Lys
                245                 250                 255

Val Ala Gly Phe Asn Leu Leu Met Thr Leu Arg Leu Trp Ser Ser
            260                 265                 270

<210> SEQ ID NO 17
<211> LENGTH: 315

<212> TYPE: PRT
<213> ORGANISM: Artificial Sequence
<220> FEATURE:
<223> OTHER INFORMATION: Synthetic

<400> SEQUENCE: 17

Met Gly Thr Arg Leu Phe Phe Tyr Val Ala Leu Cys Leu Leu Trp Thr
1               5                   10                  15

Gly His Met Asp Ala Gly Ile Thr Gln Ser Pro Arg His Lys Val Thr
            20                  25                  30

Glu Thr Gly Thr Pro Val Thr Leu Arg Cys His Gln Thr Glu Asn His
        35                  40                  45

Arg Tyr Met Tyr Trp Tyr Arg Gln Asp Pro Gly His Gly Leu Arg Leu
    50                  55                  60

Ile His Tyr Ser Tyr Gly Val Lys Asp Thr Asp Lys Gly Glu Val Ser
65                  70                  75                  80

Asp Gly Tyr Ser Val Ser Arg Ser Lys Thr Glu Asp Phe Leu Leu Thr
                85                  90                  95

Leu Glu Ser Ala Thr Ser Ser Gln Thr Ser Val Tyr Phe Cys Ala Ile
            100                 105                 110

Ser Pro Thr Glu Glu Gly Gly Leu Ile Phe Pro Gly Asn Thr Ile Tyr
        115                 120                 125

Phe Gly Glu Gly Ser Trp Leu Thr Val Val Glu Asp Leu Asn Lys Val
    130                 135                 140

Phe Pro Pro Glu Val Ala Val Phe Glu Pro Ser Glu Ala Glu Ile Ser
145                 150                 155                 160

His Thr Gln Lys Ala Thr Leu Val Cys Leu Ala Thr Gly Phe Phe Pro
                165                 170                 175

Asp His Val Glu Leu Ser Trp Trp Val Asn Gly Lys Glu Val His Ser
            180                 185                 190

Gly Val Cys Thr Asp Pro Gln Pro Leu Lys Glu Gln Pro Ala Leu Asn
        195                 200                 205

Asp Ser Arg Tyr Cys Leu Ser Ser Arg Leu Arg Val Ser Ala Thr Phe
    210                 215                 220

Trp Gln Asn Pro Arg Asn His Phe Arg Cys Gln Val Gln Phe Tyr Gly
225                 230                 235                 240

Leu Ser Glu Asn Asp Glu Trp Thr Gln Asp Arg Ala Lys Pro Val Thr
                245                 250                 255

Gln Ile Val Ser Ala Glu Ala Trp Gly Arg Ala Asp Cys Gly Phe Thr
            260                 265                 270

Ser Val Ser Tyr Gln Gln Gly Val Leu Ser Ala Thr Ile Leu Tyr Glu
        275                 280                 285

Ile Leu Leu Gly Lys Ala Thr Leu Tyr Ala Val Leu Val Ser Ala Leu
    290                 295                 300

Val Leu Met Ala Met Val Lys Arg Lys Asp Phe
305                 310                 315

<210> SEQ ID NO 18
<211> LENGTH: 137
<212> TYPE: PRT
<213> ORGANISM: Mus musculus

<400> SEQUENCE: 18

Asn Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile

-continued

```
                    20                  25                  30

Asn Val Pro Lys Thr Met Glu Ser Gly Thr Phe Ile Thr Asp Lys Thr
         35                  40                  45

Val Leu Asp Met Lys Ala Met Asp Ser Lys Ser Asn Gly Ala Ile Ala
 50                  55                  60

Trp Ser Asn Gln Thr Ser Phe Thr Cys Gln Asp Ile Phe Lys Glu Thr
 65                  70                  75                  80

Asn Ala Thr Tyr Pro Ser Ser Asp Val Pro Cys Asp Ala Thr Leu Thr
                 85                  90                  95

Glu Lys Ser Phe Glu Thr Asp Met Asn Leu Asn Phe Gln Asn Leu Ser
            100                 105                 110

Val Met Gly Leu Arg Ile Leu Leu Leu Lys Val Ala Gly Phe Asn Leu
        115                 120                 125

Leu Met Thr Leu Arg Leu Trp Ser Ser
    130                 135
```

<210> SEQ ID NO 19
<211> LENGTH: 173
<212> TYPE: PRT
<213> ORGANISM: Mus musculus

<400> SEQUENCE: 19

```
Glu Asp Leu Arg Asn Val Thr Pro Pro Lys Val Ser Leu Phe Glu Pro
1               5                  10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Lys Glu Val His Ser Gly Val Ser Thr Asp Pro Gln Ala Tyr Lys
    50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
        115                 120                 125

Ile Thr Ser Ala Ser Tyr Gln Gln Gly Val Leu Ser Ala Thr Ile Leu
    130                 135                 140

Tyr Glu Ile Leu Leu Gly Lys Ala Thr Leu Tyr Ala Val Leu Val Ser
145                 150                 155                 160

Thr Leu Val Val Met Ala Met Val Lys Arg Lys Asn Ser
                165                 170
```

<210> SEQ ID NO 20
<211> LENGTH: 267
<212> TYPE: PRT
<213> ORGANISM: Artificial Sequence
<220> FEATURE:
<223> OTHER INFORMATION: Synthetic

<400> SEQUENCE: 20

```
Met Ala Gln Val Ala Arg Val Asn Val Phe Leu Thr Leu Ser Thr Leu
1               5                  10                  15

Ser Leu Ala Lys Thr Thr Gln Pro Ile Ser Met Asp Ser Tyr Glu Gly
            20                  25                  30
```

```
Gln Glu Val Asn Ile Thr Cys Ser His Asn Ile Ala Thr Asn Asp
         35                  40                  45

Tyr Ile Thr Trp Tyr Gln Gln Phe Pro Ser Gln Pro Arg Phe Ile
 50                  55                  60

Ile Gln Gly Tyr Lys Thr Lys Val Thr Asn Glu Val Ala Ser Leu Phe
65                  70                  75                  80

Ile Pro Ala Asp Arg Lys Ser Ser Thr Leu Ser Leu Pro Arg Val Ser
                 85                  90                  95

Leu Ser Asp Thr Ala Val Tyr Tyr Cys Leu Val Ala Leu Asn Tyr Gly
                100                 105                 110

Gly Ser Gln Gly Asn Leu Ile Phe Gly Lys Gly Thr Lys Leu Ser Val
            115                 120                 125

Lys Pro Asn Ile Gln Asn Pro Glu Pro Ala Val Tyr Gln Leu Lys Asp
130                 135                 140

Pro Arg Ser Gln Asp Ser Thr Leu Cys Leu Phe Thr Asp Phe Asp Ser
145                 150                 155                 160

Gln Ile Asn Val Pro Lys Thr Met Glu Ser Gly Thr Phe Ile Thr Asp
                165                 170                 175

Lys Thr Val Leu Asp Met Lys Ala Met Asp Ser Lys Ser Asn Gly Ala
                180                 185                 190

Ile Ala Trp Ser Asn Gln Thr Ser Phe Thr Cys Gln Asp Ile Phe Lys
            195                 200                 205

Glu Thr Asn Ala Thr Tyr Pro Ser Ser Asp Val Pro Cys Asp Ala Thr
210                 215                 220

Leu Thr Glu Lys Ser Phe Glu Thr Asp Met Asn Leu Asn Phe Gln Asn
225                 230                 235                 240

Leu Ser Val Met Gly Leu Arg Ile Leu Leu Leu Lys Val Ala Gly Phe
                245                 250                 255

Asn Leu Leu Met Thr Leu Arg Leu Trp Ser Ser
                260                 265

<210> SEQ ID NO 21
<211> LENGTH: 311
<212> TYPE: PRT
<213> ORGANISM: Artificial Sequence
<220> FEATURE:
<223> OTHER INFORMATION: Synthetic

<400> SEQUENCE: 21

Met Gly Thr Arg Leu Phe Phe Tyr Val Ala Leu Cys Leu Leu Trp Thr
1               5                  10                  15

Gly His Met Asp Ala Gly Ile Thr Gln Ser Pro Arg His Lys Val Thr
                20                  25                  30

Glu Thr Gly Thr Pro Val Thr Leu Arg Cys His Gln Thr Glu Asn His
            35                  40                  45

Arg Tyr Met Tyr Trp Tyr Arg Gln Asp Pro Gly His Gly Leu Arg Leu
 50                  55                  60

Ile His Tyr Ser Tyr Gly Val Lys Asp Thr Asp Lys Gly Glu Val Ser
65                  70                  75                  80

Asp Gly Tyr Ser Val Ser Arg Ser Lys Thr Glu Asp Phe Leu Leu Thr
                85                  90                  95

Leu Glu Ser Ala Thr Ser Ser Gln Thr Ser Val Tyr Phe Cys Ala Ile
                100                 105                 110

Ser Pro Thr Glu Glu Gly Gly Leu Ile Phe Pro Gly Asn Thr Ile Tyr
            115                 120                 125
```

```
Phe Gly Glu Gly Ser Trp Leu Thr Val Val Glu Asp Leu Arg Asn Val
            130                 135                 140

Thr Pro Pro Lys Val Ser Leu Phe Glu Pro Ser Lys Ala Glu Ile Ala
145                 150                 155                 160

Asn Lys Gln Lys Ala Thr Leu Val Cys Leu Ala Arg Gly Phe Phe Pro
                165                 170                 175

Asp His Val Glu Leu Ser Trp Trp Val Asn Gly Lys Glu Val His Ser
            180                 185                 190

Gly Val Ser Thr Asp Pro Gln Ala Tyr Lys Glu Ser Asn Tyr Ser Tyr
        195                 200                 205

Cys Leu Ser Ser Arg Leu Arg Val Ser Ala Thr Phe Trp His Asn Pro
210                 215                 220

Arg Asn His Phe Arg Cys Gln Val Gln Phe His Gly Leu Ser Glu Glu
225                 230                 235                 240

Asp Lys Trp Pro Glu Gly Ser Pro Lys Pro Val Thr Gln Asn Ile Ser
                245                 250                 255

Ala Glu Ala Trp Gly Arg Ala Asp Cys Gly Ile Thr Ser Ala Ser Tyr
            260                 265                 270

Gln Gln Gly Val Leu Ser Ala Thr Ile Leu Tyr Glu Ile Leu Leu Gly
        275                 280                 285

Lys Ala Thr Leu Tyr Ala Val Leu Val Ser Thr Leu Val Val Met Ala
    290                 295                 300

Met Val Lys Arg Lys Asn Ser
305                 310

<210> SEQ ID NO 22
<211> LENGTH: 137
<212> TYPE: PRT
<213> ORGANISM: Artificial Sequence
<220> FEATURE:
<223> OTHER INFORMATION: Synthetic

<400> SEQUENCE: 22

Asn Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
            20                  25                  30

Asn Val Pro Lys Thr Met Glu Ser Gly Thr Phe Ile Thr Asp Lys Cys
        35                  40                  45

Val Leu Asp Met Lys Ala Met Asp Ser Lys Ser Asn Gly Ala Ile Ala
    50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Ser
            100                 105                 110

Val Met Gly Leu Arg Ile Leu Leu Leu Lys Val Ala Gly Phe Asn Leu
        115                 120                 125

Leu Met Thr Leu Arg Leu Trp Ser Ser
    130                 135

<210> SEQ ID NO 23
<211> LENGTH: 173
<212> TYPE: PRT
<213> ORGANISM: Artificial Sequence
```

<220> FEATURE:
<223> OTHER INFORMATION: Synthetic

<400> SEQUENCE: 23

```
Glu Asp Leu Arg Asn Val Thr Pro Pro Lys Val Ser Leu Phe Glu Pro
1               5                  10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Lys Glu Val His Ser Gly Val Cys Thr Asp Pro Gln Ala Tyr Lys
    50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
        115                 120                 125

Ile Thr Ser Ala Ser Tyr Gln Gln Gly Val Leu Ser Ala Thr Ile Leu
    130                 135                 140

Tyr Glu Ile Leu Leu Gly Lys Ala Thr Leu Tyr Ala Val Leu Val Ser
145                 150                 155                 160

Thr Leu Val Val Met Ala Met Val Lys Arg Lys Asn Ser
                165                 170
```

<210> SEQ ID NO 24
<211> LENGTH: 267
<212> TYPE: PRT
<213> ORGANISM: Artificial Sequence
<220> FEATURE:
<223> OTHER INFORMATION: Synthetic

<400> SEQUENCE: 24

```
Met Ala Gln Val Ala Arg Val Asn Val Phe Leu Thr Leu Ser Thr Leu
1               5                  10                  15

Ser Leu Ala Lys Thr Thr Gln Pro Ile Ser Met Asp Ser Tyr Glu Gly
            20                  25                  30

Gln Glu Val Asn Ile Thr Cys Ser His Asn Asn Ile Ala Thr Asn Asp
        35                  40                  45

Tyr Ile Thr Trp Tyr Gln Gln Phe Pro Ser Gln Gly Pro Arg Phe Ile
    50                  55                  60

Ile Gln Gly Tyr Lys Thr Lys Val Thr Asn Glu Val Ala Ser Leu Phe
65                  70                  75                  80

Ile Pro Ala Asp Arg Lys Ser Ser Thr Leu Ser Leu Pro Arg Val Ser
                85                  90                  95

Leu Ser Asp Thr Ala Val Tyr Tyr Cys Leu Val Ala Leu Asn Tyr Gly
            100                 105                 110

Gly Ser Gln Gly Asn Leu Ile Phe Gly Lys Gly Thr Lys Leu Ser Val
        115                 120                 125

Lys Pro Asn Ile Gln Asn Pro Glu Pro Ala Val Tyr Gln Leu Lys Asp
    130                 135                 140

Pro Arg Ser Gln Asp Ser Thr Leu Cys Leu Phe Thr Asp Phe Asp Ser
145                 150                 155                 160

Gln Ile Asn Val Pro Lys Thr Met Glu Ser Gly Thr Phe Ile Thr Asp
```

```
                165                 170                 175
Lys Cys Val Leu Asp Met Lys Ala Met Asp Ser Lys Ser Asn Gly Ala
            180                 185                 190

Ile Ala Trp Ser Asn Gln Thr Ser Phe Thr Cys Gln Asp Ile Phe Lys
        195                 200                 205

Glu Thr Asn Ala Thr Tyr Pro Ser Ser Asp Val Pro Cys Asp Ala Thr
    210                 215                 220

Leu Thr Glu Lys Ser Phe Glu Thr Asp Met Asn Leu Asn Phe Gln Asn
225                 230                 235                 240

Leu Ser Val Met Gly Leu Arg Ile Leu Leu Lys Val Ala Gly Phe
            245                 250                 255

Asn Leu Leu Met Thr Leu Arg Leu Trp Ser Ser
            260                 265

<210> SEQ ID NO 25
<211> LENGTH: 311
<212> TYPE: PRT
<213> ORGANISM: Artificial Sequence
<220> FEATURE:
<223> OTHER INFORMATION: Synthetic

<400> SEQUENCE: 25

Met Gly Thr Arg Leu Phe Phe Tyr Val Ala Leu Cys Leu Leu Trp Thr
1               5                   10                  15

Gly His Met Asp Ala Gly Ile Thr Gln Ser Pro Arg His Lys Val Thr
            20                  25                  30

Glu Thr Gly Thr Pro Val Thr Leu Arg Cys His Gln Thr Glu Asn His
        35                  40                  45

Arg Tyr Met Tyr Trp Tyr Arg Gln Asp Pro Gly His Gly Leu Arg Leu
    50                  55                  60

Ile His Tyr Ser Tyr Gly Val Lys Asp Thr Asp Lys Gly Glu Val Ser
65                  70                  75                  80

Asp Gly Tyr Ser Val Ser Arg Ser Lys Thr Glu Asp Phe Leu Leu Thr
                85                  90                  95

Leu Glu Ser Ala Thr Ser Ser Gln Thr Ser Val Tyr Phe Cys Ala Ile
            100                 105                 110

Ser Pro Thr Glu Glu Gly Gly Leu Ile Phe Pro Gly Asn Thr Ile Tyr
        115                 120                 125

Phe Gly Glu Gly Ser Trp Leu Thr Val Val Glu Asp Leu Arg Asn Val
    130                 135                 140

Thr Pro Pro Lys Val Ser Leu Phe Glu Pro Ser Lys Ala Glu Ile Ala
145                 150                 155                 160

Asn Lys Gln Lys Ala Thr Leu Val Cys Leu Ala Arg Gly Phe Phe Pro
                165                 170                 175

Asp His Val Glu Leu Ser Trp Trp Val Asn Gly Lys Glu Val His Ser
            180                 185                 190

Gly Val Cys Thr Asp Pro Gln Ala Tyr Lys Glu Ser Asn Tyr Ser Tyr
        195                 200                 205

Cys Leu Ser Ser Arg Leu Arg Val Ser Ala Thr Phe Trp His Asn Pro
    210                 215                 220

Arg Asn His Phe Arg Cys Gln Val Gln Phe His Gly Leu Ser Glu Glu
225                 230                 235                 240

Asp Lys Trp Pro Glu Gly Ser Pro Lys Pro Val Thr Gln Asn Ile Ser
                245                 250                 255

Ala Glu Ala Trp Gly Arg Ala Asp Cys Gly Ile Thr Ser Ala Ser Tyr
```

```
                    260                 265                 270
Gln Gln Gly Val Leu Ser Ala Thr Ile Leu Tyr Glu Ile Leu Leu Gly
            275                 280                 285

Lys Ala Thr Leu Tyr Ala Val Leu Val Ser Thr Leu Val Val Met Ala
        290                 295                 300

Met Val Lys Arg Lys Asn Ser
305                 310

<210> SEQ ID NO 26
<211> LENGTH: 81
<212> TYPE: DNA
<213> ORGANISM: Artificial Sequence
<220> FEATURE:
<223> OTHER INFORMATION: Synthetic

<400> SEQUENCE: 26
cgggccaagc ggtccggatc cggagccacc aacttcagcc tgctgaagca ggccggcgac      60
gtggaggaga accccggccc c                                               81

<210> SEQ ID NO 27
<211> LENGTH: 21
<212> TYPE: DNA
<213> ORGANISM: Homo sapiens

<400> SEQUENCE: 27
aacattgcta caaatgatta t                                               21

<210> SEQ ID NO 28
<211> LENGTH: 12
<212> TYPE: DNA
<213> ORGANISM: Homo sapiens

<400> SEQUENCE: 28
ggatacaaga ca                                                         12

<210> SEQ ID NO 29
<211> LENGTH: 42
<212> TYPE: DNA
<213> ORGANISM: Homo sapiens

<400> SEQUENCE: 29
ctcgtggccc tgaattatgg aggaagccaa ggaaatctca tc                        42

<210> SEQ ID NO 30
<211> LENGTH: 15
<212> TYPE: DNA
<213> ORGANISM: Homo sapiens

<400> SEQUENCE: 30
gagaaccacc gctat                                                      15

<210> SEQ ID NO 31
<211> LENGTH: 18
<212> TYPE: DNA
<213> ORGANISM: Homo sapiens

<400> SEQUENCE: 31
tcatatggtg ttaaagat                                                   18

<210> SEQ ID NO 32
<211> LENGTH: 54
<212> TYPE: DNA
```

<213> ORGANISM: Homo sapiens

<400> SEQUENCE: 32

| gccatcagcc cgacagagga gggcggactc atattccctg gaaacaccat atat | 54 |
|---|---|

<210> SEQ ID NO 33
<211> LENGTH: 390
<212> TYPE: DNA
<213> ORGANISM: Homo sapiens

<400> SEQUENCE: 33

| atggcgcaag tggcgagagt gaacgtgttc ctgaccctga gtactttgag ccttgctaag | 60 |
|---|---|
| accacccagc ccatctccat ggactcatat gaaggacaag aagtgaacat aacctgtagc | 120 |
| cacaacaaca ttgctacaaa tgattatatc acgtggtacc aacagtttcc cagccaagga | 180 |
| ccacgattta ttattcaagg atacaagaca aaagttacaa acgaagtggc ctccctgttt | 240 |
| atccctgccg acagaaagtc cagcactctg agcctgcccc gggtttccct gagcgacact | 300 |
| gctgtgtact actgcctcgt ggccctgaat tatggaggaa gccaaggaaa tctcatcttt | 360 |
| ggaaaaggca ctaaactctc tgttaaacca | 390 |

<210> SEQ ID NO 34
<211> LENGTH: 414
<212> TYPE: DNA
<213> ORGANISM: Homo sapiens

<400> SEQUENCE: 34

| atgggcacaa ggttgttctt ctatgtggcc ctttgtctcc tgtggacagg acacatggat | 60 |
|---|---|
| gctggaatca cccagagccc aagacacaag gtcacagaga caggaacacc agtgactctg | 120 |
| agatgtcacc agactgagaa ccaccgctat atgtactggt atcgacaaga cccggggcat | 180 |
| gggctgaggc tgatccatta ctcatatggt gttaaagata ctgacaaagg agaagtctca | 240 |
| gatggctata gtgtctctag atcaaagaca gaggatttcc tcctcactct ggagtccgct | 300 |
| accagctccc agacatctgt gtacttctgt gccatcagcc cgacagagga gggcggactc | 360 |
| atattccctg gaaacaccat atattttgga gagggaagtt ggctcactgt tgta | 414 |

<210> SEQ ID NO 35
<211> LENGTH: 423
<212> TYPE: DNA
<213> ORGANISM: Homo sapiens

<400> SEQUENCE: 35

| aatatccaga accctgaccc tgccgtgtac cagctgagag actctaaatc cagtgacaag | 60 |
|---|---|
| tctgtctgcc tattcaccga tttttgattct caaacaaatg tgtcacaaag taaggattct | 120 |
| gatgtgtata tcacagacaa aactgtgcta gacatgaggc tatggacttc aagagcaac | 180 |
| agtgctgtgg cctggagcaa caatctgac tttgcatgtg caaacgtctt caacaacagc | 240 |
| attattccag aagacacctt cttccccagc ccagaaagtt cctgtgatgt caagctggtc | 300 |
| gagaaaagct ttgaaacaga tacgaaccta aactttcaaa acctgtcagt gattgggttc | 360 |
| cgaatcctcc tcctgaaagt ggccgggttt aatctgctca tgacgctgcg gctgtggtcc | 420 |
| agc | 423 |

<210> SEQ ID NO 36
<211> LENGTH: 534
<212> TYPE: DNA
<213> ORGANISM: Homo sapiens

<400> SEQUENCE: 36

```
gaggacctga acaaggtgtt cccacccgag gtcgctgtgt ttgagccatc agaagcagag      60
atctcccaca cccaaaaggc cacactggtg tgcctggcca caggcttctt ccctgaccac     120
gtggagctga gctggtgggt gaatgggaag gaggtgcaca gtggggtcag cacggacccg     180
cagcccctca aggagcagcc cgccctcaat gactccagat actgcctgag cagccgcctg     240
agggtctcgg ccaccttctg gcagaacccc cgcaaccact tccgctgtca agtccagttc     300
tacgggctct cggagaatga cgagtggacc caggataggg ccaaacccgt cacccagatc     360
gtcagcgccg aggcctgggg tagagcagac tgtggcttta cctcggtgtc ctaccagcaa     420
ggggtcctgt ctgccaccat cctctatgag atcctgctag ggaaggccac cctgtatgct     480
gtgctggtca gcgcccttgt gttgatggca atggtcaaga gaaaggattt ctga          534
```

<210> SEQ ID NO 37
<211> LENGTH: 813
<212> TYPE: DNA
<213> ORGANISM: Homo sapiens

<400> SEQUENCE: 37

```
atggcgcaag tggcgagagt gaacgtgttc ctgaccctga gtactttgag ccttgctaag      60
accacccagc ccatctccat ggactcatat gaaggacaag aagtgaacat aacctgtagc     120
cacaacaaca ttgctacaaa tgattatatc acgtggtacc aacagtttcc cagccaagga     180
ccacgattta ttattcaagg atacaagaca aaagttacaa cgaagtggc ctccctgttt      240
atccctgccg acagaaagtc cagcactctg agcctgcccc gggtttccct gagcgacact     300
gctgtgtact actgcctcgt ggccctgaat tatggaggaa gccaaggaaa tctcatcttt     360
ggaaaaggca ctaaactctc tgttaaacca aatatccaga accctgaccc tgccgtgtac     420
cagctgagag actctaaatc cagtgacaag tctgtctgcc tattcaccga ttttgattct     480
caaacaaatg tgtcacaaag taaggattct gatgtgtata tcacagacaa aactgtgcta     540
gacatgaggt ctatggactt caagagcaac agtgctgtgg cctggagcaa caaatctgac     600
tttgcatgtg caaacgtctt caacaacagc attattccag aagacacctt cttccccagc     660
ccagaaagtt cctgtgatgt caagctggtc gagaaaagct ttgaaacaga tacgaaccta     720
aactttcaaa acctgtcagt gattgggttc cgaatcctcc tcctgaaagt ggccgggttt     780
aatctgctca tgacgctgcg gctgtggtcc agc                                  813
```

<210> SEQ ID NO 38
<211> LENGTH: 948
<212> TYPE: DNA
<213> ORGANISM: Homo sapiens

<400> SEQUENCE: 38

```
atgggcacaa ggttgttctt ctatgtggcc ctttgtctcc tgtggacagg acacatggat      60
gctggaatca cccagagccc aagacacaag gtcacagaga caggaacacc agtgactctg     120
agatgtcacc agactgagaa ccaccgctat atgtactggt atcgacaaga cccgggggcat    180
gggctgaggc tgatccatta ctcatatggt gttaaagata ctgacaaagg agaagtctca     240
gatggctata gtgtctctag atcaaagaca gaggatttcc ttctcactct ggagtccgct     300
accagctccc agacatctgt gtacttctgt gccatcagcc cgacagagga gggcggactc     360
atattccctg gaaacaccat atattttgga gagggaagtt ggctcactgt tgtagaggac     420
```

```
ctgaacaagg tgttcccacc cgaggtcgct gtgtttgagc catcagaagc agagatctcc    480
cacacccaaa aggccacact ggtgtgcctg gccacaggct tcttccctga ccacgtggag    540
ctgagctggt gggtgaatgg aaggaggtg cacagtgggg tcagcacgga cccgcagccc    600
ctcaaggagc agcccgccct caatgactcc agatactgcc tgagcagccg cctgagggtc    660
tcggccacct tctggcagaa ccccgcaac cacttccgct gtcaagtcca gttctacggg    720
ctctcggaga tgacgagtg gacccaggat agggccaaac ccgtcaccca gatcgtcagc    780
gccgaggcct ggggtagagc agactgtggc tttacctcgg tgtcctacca gcaagggggtc    840 ctgtctgcca ccatcctcta tgagatcctg ctagggaagg ccaccctgta tgctgtgctg    900
gtcagcgccc ttgtgttgat ggcaatggtc aagagaaagg atttctga                948

<210> SEQ ID NO 39
<211> LENGTH: 1842
<212> TYPE: DNA
<213> ORGANISM: Artificial Sequence
<220> FEATURE:
<223> OTHER INFORMATION: Synthetic

<400> SEQUENCE: 39
atggcgcaag tggcgagagt gaacgtgttc ctgaccctga gtactttgag ccttgctaag     60
accacccagc ccatctccat ggactcatat gaaggacaag aagtgaacat aacctgtagc    120
cacaacaaca ttgctacaaa tgattatatc acgtggtacc aacagtttcc cagccaagga    180
ccacgattta ttattcaagg atacaagaca aaagttacaa cgaagtggc ctccctgttt    240 atccctgccg acagaaagtc cagcactctg agcctgcccc gggtttccct gagcgacact    300
gctgtgtact actgcctcgt ggccctgaat tatggaggaa gccaaggaaa tctcatcttt    360
ggaaaaggca ctaaactctc tgttaaacca aatatccaga accctgaccc tgccgtgtac    420
cagctgagag actctaaatc cagtgacaag tctgtctgcc tattcaccga ttttgattct    480
caaacaaatg tgtcacaaag taaggattct gatgtgtata tcacagacaa aactgtgcta    540
gacatgaggt ctatggactt caagagcaac agtgctgtgg cctggagcaa caaatctgac    600
tttgcatgtg caaacgtctt caacaacagc attattccag aagacacctt cttccccagc    660
ccagaaagtt cctgtgatgt caagctggtc gagaaaagct ttgaaacaga tacgaaccta    720
aactttcaaa acctgtcagt gattgggttc cgaatcctcc tcctgaaagt ggccgggttt    780
aatctgctca tgacgctgcg gctgtggtcc agccgggcca agcggtccgg atccggagcc    840
accaacttca gcctgctgaa gcaggccggc gacgtggagg agaaccccgg ccccatgggc    900
acaaggttgt tcttctatgt ggccctttgt ctcctgtgga caggacacat ggatgctgga    960
atcacccaga gccaagacaa aggtcaca gagacaggaa caccagtgac tctgagatgt   1020
caccagactg agaaccaccg ctatatgtac tggtatcgac aagaccccgg gcatgggctg   1080
aggctgatcc attactcata tggtgttaaa gatactgaca aggagaagt ctcagatggc   1140 tatagtgtct ctagatcaaa gacagaggat ttcctcctca ctctggagtc cgctaccagc   1200
tcccagacat ctgtgtactt ctgtgccatc agcccgacag aggagggcgg actcatattc   1260
cctgaaaaca ccatatattt tggagaggga agttggctca ctgttgtaga ggacctgaac   1320
aaggtgttcc cacccgaggt cgctgtgttt gagccatcag aagcagagat ctcccacacc   1380
caaaaggcca cactggtgtg cctggccaca ggcttcttcc ctgaccacgt ggagctgagc   1440
tggtgggtga atgggaagga ggtgcacagt ggggtcagca cggacccgca gccctcaag   1500 gagcagcccg ccctcaatga ctccagatac tgcctgagca gccgcctgag ggtctcggcc   1560
```

-continued

```
accttctggc agaaccccg caaccacttc cgctgtcaag tccagttcta cgggctctcg      1620
gagaatgacg agtggaccca ggatagggcc aaacccgtca cccagatcgt cagcgccgag      1680
gcctggggta gagcagactg tggctttacc tcggtgtcct accagcaagg ggtcctgtct      1740
gccaccatcc tctatgagat cctgctaggg aaggccaccc tgtatgctgt gctggtcagc      1800
gcccttgtgt tgatggcaat ggtcaagaga aaggatttct ga                        1842
```

<210> SEQ ID NO 40
<211> LENGTH: 423
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (142)..(144)
<223> OTHER INFORMATION: nnn is tgc or tgt

<400> SEQUENCE: 40

```
aatatccaga accctgaccc tgccgtgtac cagctgagag actctaaatc cagtgacaag       60
tctgtctgcc tattcaccga ttttgattct caaacaaatg tgtcacaaag taaggattct      120
gatgtgtata tcacagacaa annngtgcta gacatgaggt ctatggactt caagagcaac      180
agtgctgtgg cctggagcaa caaatctgac tttgcatgtg caaacgtctt caacaacagc      240
attattccag aagacacctt cttccccagc ccagaaagtt cctgtgatgt caagctggtc      300
gagaaaagct ttgaaacaga tacgaaccta aactttcaaa acctgtcagt gattgggttc      360
cgaatcctcc tcctgaaagt ggccgggttt aatctgctca tgacgctgcg gctgtggtcc      420
agc                                                                    423
```

<210> SEQ ID NO 41
<211> LENGTH: 534
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (169)..(171)
<223> OTHER INFORMATION: nnn is tgc or tgt

<400> SEQUENCE: 41

```
gaggacctga acaaggtgtt cccacccgag gtcgctgtgt ttgagccatc agaagcagag       60
atctcccaca cccaaaaggc cacactggtg tgcctggcca caggcttctt ccctgaccac      120
gtggagctga gctggtgggt gaatgggaag gaggtgcaca gtggggtcnn nacggacccg      180
cagcccctca aggagcagcc cgccctcaat gactccagat actgcctgag cagccgcctg      240
agggtctcgg ccaccttctg gcagaacccc cgcaaccact tccgctgtca agtccagttc      300
tacgggctct cggagaatga cgagtggacc aggatagggc caaacccgt cacccagatc       360 gtcagcgccg aggcctgggg tagagcagac tgtggcttta cctcggtgtc ctaccagcaa      420
ggggtcctgt ctgccaccat cctctatgag atcctgctag ggaaggccac cctgtatgct      480
gtgctggtca gcgcccttgt gttgatggca atggtcaaga gaaaggattt ctga            534
```

<210> SEQ ID NO 42
<211> LENGTH: 813
<212> TYPE: DNA
<213> ORGANISM: Artificial Sequence
<220> FEATURE:

```
<223> OTHER INFORMATION: Synthetic
<220> FEATURE:
<221> NAME/KEY: misc_feature
<222> LOCATION: (532)..(534)
<223> OTHER INFORMATION: nnn is tgc or tgt

<400> SEQUENCE: 42
atggcgcaag tggcgagagt gaacgtgttc ctgaccctga gtactttgag ccttgctaag      60
accacccagc ccatctccat ggactcatat gaaggacaag aagtgaacat aacctgtagc     120
cacaacaaca ttgctacaaa tgattatatc acgtggtacc aacagtttcc cagccaagga    180
ccacgattta ttattcaagg atacaagaca aaagttacaa acgaagtggc ctccctgttt    240
atccctgccg acagaaagtc cagcactctg agcctgcccc gggtttccct gagcgacact    300
gctgtgtact actgcctcgt ggccctgaat tatggaggaa gccaaggaaa tctcatcttt    360
ggaaaaggca ctaaactctc tgttaaacca aatatccaga accctgaccc tgccgtgtac    420
cagctgagag actctaaatc cagtgacaag tctgtctgcc tattcaccga ttttgattct    480
caaacaaatg tgtcacaaag taaggattct gatgtgtata tcacagacaa annngtgcta    540
gacatgaggt ctatggactt caagagcaac agtgctgtgg cctggagcaa caaatctgac    600
tttgcatgtg caaacgtctt caacaacagc attattccag aagacacctt cttccccagc    660
ccagaaagtt cctgtgatgt caagctggtc gagaaaagct ttgaaacaga tacgaaccta    720
aactttcaaa acctgtcagt gattgggttc gaatcctcc tcctgaaagt ggccgggttt    780
aatctgctca tgacgctgcg gctgtggtcc agc                                 813

<210> SEQ ID NO 43
<211> LENGTH: 948
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (583)..(585)
<223> OTHER INFORMATION: nnn is tgc or tgt

<400> SEQUENCE: 43
atgggcacaa ggttgttctt ctatgtggcc ctttgtctcc tgtggacagg acacatggat      60
gctggaatca cccagagccc aagacacaag gtcacagaga caggaacacc agtgactctg    120
agatgtcacc agactgagaa ccaccgctat atgtactggt atcgacaaga cccggggcat    180
gggctgaggc tgatccatta ctcatatggt gttaaagata ctgacaaagg agaagtctca    240
gatggctata gtgtctctag atcaaagaca gaggatttcc tcctcactct ggagtccgct    300
accagctccc agacatctgt gtacttctgt gccatcagcc cgacagagga gggcggactc    360
atattccctg gaaacaccat atattttgga gagggaagtt ggctcactgt tgtagaggac    420
ctgaacaagg tgttcccacc cgaggtcgct gtgtttgagc atcagaagc agatctcc      480 cacacccaaa aggccacact ggtgtgcctg gccacaggct tcttccctga ccacgtggag    540
ctgagctggt gggtgaatgg gaaggaggtg cacagtgggg tcnnnacgga cccgcagccc    600
ctcaaggagc agcccgccct caatgactcc agatactgcc tgagcagccg cctgagggtc    660
tcggccacct tctggcagaa cccccgcaac cacttccgct gtcaagtcca gttctacggg    720
ctctcggaga tgacgagtg gacccaggat agggccaaac ccgtcaccca gatcgtcagc    780
gccgaggcct ggggtagagc agactgtggc tttacctcgg tgtcctacca gcaagggtc    840 ctgtctgcca ccatcctcta tgagatcctg ctagggaagg ccaccctgta tgctgtgctg    900
```

```
                  gtcagcgccc ttgtgttgat ggcaatggtc aagagaaagg atttctga      948

<210> SEQ ID NO 44
<211> LENGTH: 1842
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (532)..(534)
<223> OTHER INFORMATION: nnn is tgc or tgt
<220> FEATURE:
<221> NAME/KEY: misc_feature
<222> LOCATION: (1477)..(1479)
<223> OTHER INFORMATION: nnn is tgc or tgt

<400> SEQUENCE: 44
atggcgcaag tggcgagagt gaacgtgttc ctgaccctga gtactttgag ccttgctaag      60
accacccagc ccatctccat ggactcatat gaaggacaag aagtgaacat aacctgtagc     120
cacaacaaca ttgctacaaa tgattatatc acgtggtacc aacagtttcc cagccaagga     180
ccacgattta ttattcaagg atacaagaca aaagttacaa cgaagtggc ctccctgttt      240 atccctgccg acagaaagtc cagcactctg agcctgcccc gggtttccct gagcgacact     300
gctgtgtact actgcctcgt ggccctgaat tatggaggaa gccaaggaaa tctcatcttt     360
ggaaaaggca ctaaactctc tgttaaacca aatatccaga accctgaccc tgccgtgtac     420
cagctgagag actctaaatc cagtgacaag tctgtctgcc tattcaccga ttttgattct     480
caaacaaatg tgtcacaaag taaggattct gatgtgtata tcacagacaa annngtgcta     540
gacatgaggt ctatggactt caagagcaac agtgctgtgg cctggagcaa caaatctgac     600
tttgcatgtg caaacgtctt caacaacagc attattccag aagacacctt cttccccagc     660
ccagaaagtt cctgtgatgt caagctggtc gagaaaagct ttgaaacaga tacgaaccta     720
aactttcaaa acctgtcagt gattgggttc gaatcctcc tcctgaaagt ggccgggttt     780
aatctgctca tgacgctgcg gctgtggtcc agccgggcca agcggtccgg atccggagcc     840
accaacttca gcctgctgaa gcaggccggc gacgtggagg agaaccccgg ccccatgggc     900
acaaggttgt tcttctatgt ggccctttgt ctcctgtgga caggacacat ggatgctgga     960
atcacccaga gcccaagaca caaggtcaca gagacaggaa caccagtgac tctgagatgt     1020
caccagactg agaaccaccg ctatatgtac tggtatcgac aagacccggg catgggctg     1080 aggctgatcc attactcata tggtgttaaa gatactgaca aaggagaagt ctcagatggc     1140
tatagtgtct ctagatcaaa gacagaggat ttcctcctca ctctggagtc cgctaccagc     1200
tcccagacat ctgtgtactt ctgtgccatc agcccgacag aggagggcgg actcatattc     1260
cctggaaaca ccatatattt tggagaggga gttggctca ctgttgtaga ggacctgaac     1320
aaggtgttcc cacccgaggt cgctgtgttt gagccatcag aagcagagat ctcccacacc     1380
caaaaggcca cactggtgtg cctggccaca ggcttcttcc ctgaccacgt ggagctgagc     1440
tggtgggtga atgggaagga ggtgcacagt ggggtcnnna cggacccgca gcccctcaag     1500
gagcagcccg ccctcaatga ctccagatac tgcctgagca gccgcctgag ggtctcggcc     1560
accttctggg cagaaccccg caaccacttc cgctgtcaag tccagttcta cgggctctcg     1620
gagaatgacg agtggaccca ggatagggcc aaacccgtca cccagatcgt cagcgccgag     1680
gcctggggta gagcagactg tggctttacc tcggtgtcct accagcaagg ggtcctgtct     1740
```

| gccaccatcc tctatgagat cctgctaggg aaggccaccc tgtatgctgt gctggtcagc | 1800 |
| gcccttgtgt tgatggcaat ggtcaagaga aaggatttct ga | 1842 |

<210> SEQ ID NO 45
<211> LENGTH: 411
<212> TYPE: DNA
<213> ORGANISM: Mus musculus

<400> SEQUENCE: 45

| aatatccaga acccagaacc tgctgtgtac cagttaaaag atcctcggtc tcaggacagc | 60 |
| accctctgcc tgttcaccga ctttgactcc caaatcaatg tgccgaaaac catggaatct | 120 |
| ggaacgttca tcactgacaa aactgtgctg gacatgaaag ctatggattc caagagcaat | 180 |
| ggggccattg cctggagcaa ccagacaagc ttcacctgcc aagatatctt caaagagacc | 240 |
| aacgccacct accccagttc agacgttccc tgtgatgcca cgttgactga aaaagcttt | 300 |
| gaaacagata tgaacctaaa ctttcaaaac ctgtcagtta tgggactccg aatcctcctg | 360 |
| ctgaaagtag ccggatttaa cctgctcatg acgctgaggc tgtggtccag t | 411 |

<210> SEQ ID NO 46
<211> LENGTH: 522
<212> TYPE: DNA
<213> ORGANISM: Mus musculus

<400> SEQUENCE: 46

| gaggatctga gaaatgtgac tccacccaag gtctccttgt ttgagccatc aaaagcagag | 60 |
| attgcaaaca acaaaaaggc taccctcgtg tgcttggcca ggggcttctt ccctgaccac | 120 |
| gtggagctga gctggtgggt gaatggcaag gaggtccaca gtggggtcag cacggaccct | 180 |
| caggcctaca aggagagcaa ttatagctac tgcctgagca gccgcctgag ggtctctgct | 240 |
| accttctggc acaatcctcg caaccacttc cgctgccaag tgcagttcca tgggctttca | 300 |
| gaggaggaca gtggccaga gggctcaccc aaacctgtca cacagaacat cagtgcagag | 360 |
| gcctggggcc gagcagactg tgggattacc tcagcatcct atcaacaagg ggtcttgtct | 420 |
| gccaccatcc tctatgagat cctgctaggg aaagccaccc tgtatgctgt gcttgtcagt | 480 |
| acactggtgg tgatggctat ggtcaaaaga aagaattcat ga | 522 |

<210> SEQ ID NO 47
<211> LENGTH: 801
<212> TYPE: DNA
<213> ORGANISM: Artificial Sequence
<220> FEATURE:
<223> OTHER INFORMATION: Synthetic

<400> SEQUENCE: 47

| atggcgcaag tggcgagagt gaacgtgttc ctgaccctga gtactttgag ccttgctaag | 60 |
| accacccagc ccatctccat ggactcatat gaaggacaag aagtgaacat aacctgtagc | 120 |
| cacaacaaca ttgctacaaa tgattacatc acgtggtacc aacagtttcc cagccaagga | 180 |
| ccacgattta ttattcaagg atacaagaca aaagttacaa acgaagtggc ctccctgttt | 240 |
| atccctgccg acagaaagtc cagcactctg agcctgcccc gggtttccct gagcgacact | 300 |
| gctgtgtact actgcctcgt ggccctgaat tatggaggaa gccaaggaaa tctcatcttt | 360 |
| ggaaaaggca ctaaactctc tgttaaacca aatatccaga acccagaacc tgctgtgtac | 420 |
| cagttaaaag atcctcggtc tcaggacagc accctctgcc tgttcaccga ctttgactcc | 480 |
| caaatcaatg tgccgaaaac catggaatct ggaacgttca tcactgacaa aactgtgctg | 540 |

| | |
|---|---|
| gacatgaaag ctatggattc aagagcaat ggggccattg cctggagcaa ccagacaagc | 600 |
| ttcacctgcc aagatatctt caaagagacc aacgccacct accccagttc agacgttccc | 660 |
| tgtgatgcca cgttgactga gaaaagcttt gaaacagata tgaacctaaa ctttcaaaac | 720 |
| ctgtcagtta tgggactccg aatcctcctg ctgaaagtag ccggatttaa cctgctcatg | 780 |
| acgctgaggc tgtggtccag t | 801 |

<210> SEQ ID NO 48
<211> LENGTH: 936
<212> TYPE: DNA
<213> ORGANISM: Artificial Sequence
<220> FEATURE:
<223> OTHER INFORMATION: Synthetic

<400> SEQUENCE: 48

| | |
|---|---|
| atgggcacaa ggttgttctt ctatgtggcc ctttgtctcc tgtggacagg acacatggat | 60 |
| gctggaatca cccagagccc aagacacaag gtcacagaga caggaacacc agtgactctg | 120 |
| agatgtcacc agactgagaa ccaccgctat atgtactggt atcgacaaga cccggggcat | 180 |
| gggctgaggc tgatccatta ctcatatggt gttaaagata ctgacaaagg agaagtctca | 240 |
| gatggctata gtgtctctag atcaaagaca gaggatttcc tcctcactct ggagtccgct | 300 |
| accagctccc agacatctgt gtacttctgt gccatcagcc cgacagagga gggcggactc | 360 |
| atattccctg gaaacaccat atattttgga gagggaagtt ggctcactgt tgtagaggat | 420 |
| ctgagaaatg tgactccacc caaggtctcc ttgtttgagc catcaaaagc agagattgca | 480 |
| aacaaacaaa aggctaccct cgtgtgcttg gccaggggct tcttccctga ccacgtggag | 540 |
| ctgagctggt gggtgaatgg caaggaggtc acagtgggg tcagcacgga ccctcaggcc | 600 |
| tacaaggaga gcaattatag ctactgcctg agcagccgcc tgagggtctc tgctaccttc | 660 |
| tggcacaatc ctcgcaacca cttccgctgc caagtgcagt tccatgggct ttcagaggag | 720 |
| gacaagtggc cagagggctc acccaaacct gtcacacaga acatcagtgc agaggcctgg | 780 |
| ggccgagcag actgtgggat tacctcagca tcctatcaac aagggtctt gtctgccacc | 840 |
| atcctctatg agatcctgct agggaaagcc accctgtatg ctgtgcttgt cagtacactg | 900 |
| gtggtgatgg ctatggtcaa agaaagaat tcatga | 936 |

<210> SEQ ID NO 49
<211> LENGTH: 1818
<212> TYPE: DNA
<213> ORGANISM: Artificial Sequence
<220> FEATURE:
<223> OTHER INFORMATION: Synthetic

<400> SEQUENCE: 49

| | |
|---|---|
| atggcgcaag tggcgagagt gaacgtgttc ctgaccctga gtactttgag ccttgctaag | 60 |
| accacccagc ccatctccat ggactcatat gaaggacaag aagtgaacat aacctgtagc | 120 |
| cacaacaaca ttgctacaaa tgattacatc acgtggtacc aacagtttcc cagccaagga | 180 |
| ccacgattta ttattcaagg atacaagaca aaagttacaa cgaagtggc ctccctgttt | 240 |
| atccctgccg acagaaagtc cagcactctg agcctgcccc gggtttccct gagcgacact | 300 |
| gctgtgtact actgcctcgt ggccctgaat tatggaggaa gccaaggaaa tctcatcttt | 360 |
| ggaaaaggca ctaaactctc tgttaaacca aatatccaga cccgagaacc tgctgtgtac | 420 |
| cagttaaaag atcctcggtc tcaggacagc accctctgcc tgttcaccga ctttgactcc | 480 |

| | |
|---|---|
| caaatcaatg tgccgaaaac catggaatct ggaacgttca tcactgacaa aactgtgctg | 540 |
| gacatgaaag ctatggattc caagagcaat ggggccattg cctggagcaa ccagacaagc | 600 |
| ttcacctgcc aagatatctt caaagagacc aacgccacct accccagttc agacgttccc | 660 |
| tgtgatgcca cgttgactga gaaaagcttt gaaacagata tgaacctaaa ctttcaaaac | 720 |
| ctgtcagtta tgggactccg aatcctcctg ctgaaagtag ccggatttaa cctgctcatg | 780 |
| acgctgaggc tgtggtccag tcgggccaag cggtccggat ccggagccac caacttcagc | 840 |
| ctgctgaagc aggccggcga cgtggaggag aaccccggcc ccatgggcac aaggttgttc | 900 |
| ttctatgtgg ccctttgtct cctgtggaca ggacacatgg atgctggaat cacccagagc | 960 |
| ccaagacaca aggtcacaga cagggaacca ccagtgactc tgagatgtca ccagactgag | 1020 |
| aaccaccgct atatgtactg gtatcgacaa gacccggggc atgggctgag gctgatccat | 1080 |
| tactcatatg gtgttaaaga tactgacaaa ggagaagtct cagatggcta tagtgtctct | 1140 |
| agatcaaaga cagaggattt cctcctcact ctggagtccg ctaccagctc ccagacatct | 1200 |
| gtgtacttct gtgccatcag cccgacagag gagggcggac tcatattccc tggaaacacc | 1260 |
| atatattttg gagagggaag ttggctcact gttgtagagg atctgagaaa tgtgactcca | 1320 |
| cccaaggtct ccttgtttga gccatcaaaa gcagagattg caaacaaaca aaaggctacc | 1380 |
| ctcgtgtgct tggccagggg cttcttccct gaccacgtgg agctgagctg gtgggtgaat | 1440 |
| ggcaaggagg tccacagtgg ggtcagcacg gaccctcagg cctacaagga gagcaattat | 1500 |
| agctactgcc tgagcagccg cctgagggtc tctgctacct tctggcacaa tcctcgcaac | 1560 |
| cacttccgct gccaagtgca gttccatggg ctttcagagg aggacaagtg gccagagggc | 1620 |
| tcacccaaac ctgtcacaca gaacatcagt gcagaggcct ggggccgagc agactgtggg | 1680 |
| attacctcag catcctatca acaagggggtc ttgtctgcca ccatcctcta tgagatcctg | 1740 |
| ctagggaaag ccaccctgta tgctgtgctt gtcagtacac tggtggtgat ggctatggtc | 1800 |
| aaaagaaaga attcatga | 1818 |

<210> SEQ ID NO 50
<211> LENGTH: 411
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (142)..(144)
<223> OTHER INFORMATION: nnn is tgc or tgt

<400> SEQUENCE: 50

| | |
|---|---|
| aatatccaga acccagaacc tgctgtgtac cagttaaaag atcctcggtc tcaggacagc | 60 |
| accctctgcc tgttcaccga ctttgactcc caaatcaatg tgccgaaaac catggaatct | 120 |
| ggaacgttca tcactgacaa annngtgctg gacatgaaag ctatggattc caagagcaat | 180 |
| ggggccattg cctggagcaa ccagacaagc ttcacctgcc aagatatctt caaagagacc | 240 |
| aacgccacct accccagttc agacgttccc tgtgatgcca cgttgactga gaaaagcttt | 300 |
| gaaacagata tgaacctaaa ctttcaaaac ctgtcagtta tgggactccg aatcctcctg | 360 |
| ctgaaagtag ccggatttaa cctgctcatg acgctgaggc tgtggtccag t | 411 |

<210> SEQ ID NO 51
<211> LENGTH: 522
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (169)..(171)
<223> OTHER INFORMATION: nnn is tgc or tgt

<400> SEQUENCE: 51

```
gaggatctga gaaatgtgac tccacccaag gtctccttgt ttgagccatc aaaagcagag      60
attgcaaaca acaaaaggc taccctcgtg tgcttggcca ggggcttctt ccctgaccac     120
gtggagctga gctggtgggt gaatggcaag gaggtccaca gtggggtcnn nacggaccct     180
caggcctaca aggagagcaa ttatagctac tgcctgagca gccgcctgag ggtctctgct     240
accttctggc acaatcctcg caaccacttc cgctgccaag tgcagttcca tgggctttca     300
gaggaggaca gtggccaga gggctcaccc aaacctgtca cacagaacat cagtgcagag     360
gcctggggcc gagcagactg tgggattacc tcagcatcct atcaacaagg ggtcttgtct     420
gccaccatcc tctatgagat cctgctaggg aaagccaccc tgtatgctgt gcttgtcagt     480
acactggtgg tgatggctat ggtcaaaaga aagaattcat ga                       522
```

<210> SEQ ID NO 52
<211> LENGTH: 801
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (532)..(534)
<223> OTHER INFORMATION: nnn is tgc or tgt

<400> SEQUENCE: 52

```
atggcgcaag tggcgagagt gaacgtgttc ctgaccctga gtactttgag ccttgctaag      60
accacccagc ccatctccat ggactcatat gaaggacaag aagtgaacat aacctgtagc     120
cacaacaaca ttgctacaaa tgattacatc acgtggtacc aacagtttcc cagccaagga     180
ccacgattta ttattcaagg atacaagaca aaagttacaa acgaagtggc ctccctgttt     240
atccctgccg acagaaagtc cagcactctg agcctgcccc gggtttccct gagcgacact     300
gctgtgtact actgcctcgt ggccctgaat tatggaggaa gccaaggaaa tctcatcttt     360
ggaaaaggca ctaaactctc tgttaaacca aatatccaga acccagaacc tgctgtgtac     420
cagttaaaag atcctcggtc tcaggacagc accctctgcc tgttcaccga ctttgactcc     480
caaatcaatg tgccgaaaac catggaatct ggaacgttca tcactgacaa annngtgctg     540
gacatgaaag ctatggatc caagagcaat ggggccattg cctggagcaa ccagacaagc     600
ttcacctgcc aagatatctt caagagacc aacgccacct accccagttc agacgttccc     660
tgtgatgcca cgttgactga gaaaagcttt gaaacagata tgaacctaaa ctttcaaaac     720
ctgtcagtta tgggactccg aatcctcctg ctgaaagtag ccggatttaa cctgctcatg     780
acgctgaggc tgtggtccag t                                               801
```

<210> SEQ ID NO 53
<211> LENGTH: 936
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (583)..(585)

<223> OTHER INFORMATION: nnn is tgc or tgt

<400> SEQUENCE: 53

```
atgggcacaa ggttgttctt ctatgtggcc ctttgtctcc tgtggacagg acacatggat     60
gctggaatca cccagagccc aagacacaag gtcacagaga caggaacacc agtgactctg    120
agatgtcacc agactgagaa ccaccgctat atgtactggt atcgacaaga cccggggcat    180
gggctgaggc tgatccatta ctcatatggt gttaaagata ctgacaaagg agaagtctca    240
gatggctata gtgtctctag atcaaagaca gaggatttcc tcctcactct ggagtccgct    300
accagctccc agacatctgt gtacttctgt gccatcagcc cgacagagga gggcggactc    360
atattccctg gaaacaccat atattttgga gagggaagtt ggctcactgt tgtagaggat    420
ctgagaaatg tgactccacc caaggtctcc ttgtttgagc catcaaaagc agagattgca    480
aacaaacaaa aggctaccct cgtgtgcttg gccaggggct cttccctga ccacgtggag     540
ctgagctggt gggtgaatgg caaggaggtc cacagtgggg tcnnnacgga ccctcaggcc    600
tacaaggaga gcaattatag ctactgcctg agcagccgcc tgagggtctc tgctaccttc    660
tggcacaatc ctcgcaacca cttccgctgc caagtgcagt ccatgggct ttcagaggag     720
gacaagtggc cagagggctc acccaaacct gtcacacaga catcagtgc agaggcctgg     780
ggccgagcag actgtgggat tacctcagca tcctatcaac aagggtgtct tgtctgccacc   840
atcctctatg agatcctgct agggaaagcc accctgtatg ctgtgcttgt cagtacactg    900
gtggtgatgg ctatggtcaa agaaagaat tcatga                               936
```

<210> SEQ ID NO 54
<211> LENGTH: 1818
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (532)..(534)
<223> OTHER INFORMATION: nnn is tgc or tgt
<220> FEATURE:
<221> NAME/KEY: misc_feature
<222> LOCATION: (1465)..(1467)
<223> OTHER INFORMATION: nnn is tgc or tgt

<400> SEQUENCE: 54

```
atggcgcaag tggcgagagt gaacgtgttc ctgaccctga gtactttgag ccttgctaag    60
accacccagc ccatctccat ggactcatat gaaggacaag aagtgaacat aacctgtagc   120
cacaacaaca ttgctacaaa tgattacatc acgtggtacc aacagtttcc cagccaagga   180
ccacgattta ttattcaagg atacaagaca aaagttacaa acgaagtggc ctccctgttt   240
atccctgccg acagaaagtc cagcactctg agcctgcccc gggtttccct gagcgacact   300
gctgtgtact actgcctcgt ggccctgaat tatggaggaa gccaaggaaa tctcatcttt   360
ggaaaaggca ctaaactctc tgttaaacca aatatccaga cccagaaacc tgctgtgtac   420
cagttaaaag atcctcggtc tcaggacagc accctctgcc tgttcaccga ctttgactcc   480
caaatcaatg tgccgaaaac catggaatct ggaacgttca tcactgacaa anngngtgctg   540
gacatgaaag ctatggatc caagagcaat ggggccattg cctggagcaa ccagacaagc   600
ttcacctgcc aagatatctt caagagacc aacgccacct accccagttc agacgttccc   660
tgtgatgcca cgttgactga gaaaagcttt gaaacagata tgaacctaaa cttttcaaaac  720
ctgtcagtta tgggactccg aatcctcctg ctgaaagtag ccggatttaa cctgctcatg   780
```

```
acgctgaggc tgtggtccag tcgggccaag cggtccggat ccggagccac caacttcagc      840
ctgctgaagc aggccggcga cgtggaggag aaccccggcc ccatgggcac aaggttgttc      900
ttctatgtgg ccctttgtct cctgtggaca ggacacatgg atgctggaat cacccagagc      960
ccaagacaca aggtcacaga gacaggaaca ccagtgactc tgagatgtca ccagactgag     1020
aaccaccgct atatgtactg gtatcgacaa gacccggggc atgggctgag gctgatccat     1080
tactcatatg gtgttaaaga tactgacaaa ggagaagtct cagatggcta tagtgtctct     1140
agatcaaaga cagaggattt cctcctcact ctggagtccg ctaccagctc ccagacatct     1200
gtgtacttct gtgccatcag cccgacagag gagggcggac tcatattccc tggaaacacc     1260
atatattttg gagagggaag ttggctcact gttgtagagg atctgagaaa tgtgactcca     1320
cccaaggtct ccttgtttga gccatcaaaa gcagagattg caaacaaaca aaaggctacc     1380
ctcgtgtgct tggccagggg cttcttccct gaccacgtgg agctgagctg gtgggtgaat     1440
ggcaaggagg tccacagtgg ggtcnnnacg gaccctcagg cctacaagga gagcaattat     1500
agctactgcc tgagcagccg cctgagggtc tctgctacct tctggcacaa tcctcgcaac     1560
cacttccgct gccaagtgca gttccatggg ctttcagagg aggacaagtg gccagagggc     1620
tcacccaaac ctgtcacaca gaacatcagt gcagaggcct ggggccgagc agactgtggg     1680
attacctcag catcctatca acaagggtc ttgtctgcca ccatcctcta tgagatcctg     1740
```

```
attacctcag catcctatca acaagggtc ttgtctgcca ccatcctcta tgagatcctg     1740
ctagggaaag ccaccctgta tgctgtgctt gtcagtacac tggtggtgat ggctatggtc     1800
aaaagaaaga attcatga                                                   1818
```

<210> SEQ ID NO 55
<211> LENGTH: 130
<212> TYPE: PRT
<213> ORGANISM: Artificial Sequence
<220> FEATURE:
<223> OTHER INFORMATION: Synthetic

<400> SEQUENCE: 55

Met Gly Gln Val Ala Arg Val Asn Val Phe Leu Thr Leu Ser Thr Leu
1               5                  10                  15

Ser Leu Ala Lys Thr Thr Gln Pro Ile Ser Met Asp Ser Tyr Glu Gly
            20                  25                  30

Gln Glu Val Asn Ile Thr Cys Ser His Asn Asn Ile Ala Thr Asn Asp
        35                  40                  45

Tyr Ile Thr Trp Tyr Gln Gln Phe Pro Ser Gln Gly Pro Arg Phe Ile
    50                  55                  60

Ile Gln Gly Tyr Lys Thr Lys Val Thr Asn Glu Val Ala Ser Leu Phe
65                  70                  75                  80

Ile Pro Ala Asp Arg Lys Ser Ser Thr Leu Ser Leu Pro Arg Val Ser
                85                  90                  95

Leu Ser Asp Thr Ala Val Tyr Tyr Cys Leu Val Ala Leu Asn Tyr Gly
            100                 105                 110

Gly Ser Gln Gly Asn Leu Ile Phe Gly Lys Gly Thr Lys Leu Ser Val
        115                 120                 125

Lys Pro
    130

<210> SEQ ID NO 56
<211> LENGTH: 390
<212> TYPE: DNA
<213> ORGANISM: Artificial Sequence

```
<220> FEATURE:
<223> OTHER INFORMATION: Synthetic

<400> SEQUENCE: 56
atgggccagg tggccagagt gaacgtgttc ctgaccctga gcaccctgtc cctggccaag    60
accacccagc ccatcagcat ggacagctac gagggccagg aagtgaacat cacctgcagc   120
cacaacaata tcgccaccaa cgactacatc acctggtatc agcagttccc cagccagggc   180
cccagattca tcatccaggg ctacaagacc aaagtgacca cgaggtggc cagcctgttc    240 atccccgccg accggaagag cagcaccctg agcctgcccc gggtgtccct gagcgacacc   300
gccgtgtact actgcctggt ggccctgaac tacggcggct cccagggaaa cctgatcttc   360
ggcaagggca ccaagctgtc cgtgaagccc                                    390

<210> SEQ ID NO 57
<211> LENGTH: 423
<212> TYPE: DNA
<213> ORGANISM: Artificial Sequence
<220> FEATURE:
<223> OTHER INFORMATION: Synthetic

<400> SEQUENCE: 57
aacatccaga accccgatcc tgctgtgtac cagctgaggg acagcaagag cagcgacaag    60
agcgtgtgcc tgttcaccga cttcgacagc cagaccaacg tgtctcagtc taaggatagt   120
gatgtgtata tcaccgacaa gaccgtgctg gacatgcgga gcatggactt caagagcaac   180
agcgccgtgg cctggtccaa caagagcgac ttcgcctgcg ccaacgcctt caacaacagc   240
atcatccccg aggacacctt ttttccccagc cccgagagca gctgcgacgt gaaactggtg   300
gagaagagct tcgagacaga caccaacctg aacttccaga acctgagcgt gatcggcttc   360
agaatcctgc tgctgaaggt ggccggcttc aacctgctga tgacccctgcg gctgtggagc   420 agc                                                                 423

<210> SEQ ID NO 58
<211> LENGTH: 81
<212> TYPE: DNA
<213> ORGANISM: Artificial Sequence
<220> FEATURE:
<223> OTHER INFORMATION: Synthetic

<400> SEQUENCE: 58
cgggccaaga gaagcggcag cggcgccacc aacttcagcc tgctgaagca ggccggcgac    60
gtggaggaaa accctggccc t                                             81

<210> SEQ ID NO 59
<211> LENGTH: 414
<212> TYPE: DNA
<213> ORGANISM: Artificial Sequence
<220> FEATURE:
<223> OTHER INFORMATION: Synthetic

<400> SEQUENCE: 59
atgggcaccc ggctgttctt ctacgtggcc ctgtgcctgc tgtggaccgg ccacatggac    60
gccggcatca cccagagccc caggcacaaa gtgaccgaga caggcacccc cgtgaccctg   120
aggtgccacc agaccgagaa ccaccggtac atgtactggt acaggcagga ccccggccac   180
ggcctgcggc tgatccacta cagctacggc gtgaaggaca ccgacaaggg cgaggtgtcc   240
gacggctaca gcgtgtccag aagcaagacc gaggacttcc tgctgaccct ggaaagcgcc   300
```

```
acctccagcc agacctccgt gtacttctgc gccatcagcc ccaccgagga aggcggcctg    360
atcttccccg gcaacaccat ctacttcggc gagggcagct ggctgaccgt ggtg         414
```

<210> SEQ ID NO 60
<211> LENGTH: 534
<212> TYPE: DNA
<213> ORGANISM: Artificial Sequence
<220> FEATURE:
<223> OTHER INFORMATION: Synthetic

<400> SEQUENCE: 60

```
gaggacctga acaaggtgtt ccccccgag gtggccgtgt tcgagcccag cgaggccgag    60
atcagccaca cccagaaagc caccctggtg tgcctggcca ccggcttttt ccccgaccac   120
gtggagctgt cttggtgggt gaacggcaaa gaggtgcaca cgggcgtcag caccgacccc   180
cagcccctga aagagcagcc cgccctgaac gacagccggt actgcctgtc cagcagactg   240
cgggtgtccg ccaccttctg gcagaacccc cggaaccact ccggtgcca ggtgcagttc    300 tacgcctga gcgagaacga cgagtggacc caggacagag ccaagcctgt gacacagatc   360
gtgtccgccg aggcctgggg cagagccgac tgcggcttca ccagcgtgtc ctaccagcag   420
ggcgtgctgt ctgccaccat cctgtacgag atcctgctgg gcaaggccac cctgtacgcc   480
gtgctggtgt ctgctctggt gctgatggct atggtgaagc ggaaggactt ctga         534
```

<210> SEQ ID NO 61
<211> LENGTH: 24
<212> TYPE: DNA
<213> ORGANISM: Artificial Sequence
<220> FEATURE:
<223> OTHER INFORMATION: Synthetic

<400> SEQUENCE: 61

```
cccagcccat ctccatggac tcat                                           24
```

<210> SEQ ID NO 62
<211> LENGTH: 42
<212> TYPE: DNA
<213> ORGANISM: Artificial Sequence
<220> FEATURE:
<223> OTHER INFORMATION: Synthetic

<400> SEQUENCE: 62

```
agacctcatg tctagcacgc atttgtctgt gatatacaca tc                       42
```

<210> SEQ ID NO 63
<211> LENGTH: 42
<212> TYPE: DNA
<213> ORGANISM: Artificial Sequence
<220> FEATURE:
<223> OTHER INFORMATION: Synthetic

<400> SEQUENCE: 63

```
gatgtgtata tcacagacaa atgcgtgcta gacatgaggt ct                       42
```

<210> SEQ ID NO 64
<211> LENGTH: 74
<212> TYPE: DNA
<213> ORGANISM: Artificial Sequence
<220> FEATURE:
<223> OTHER INFORMATION: Synthetic

<400> SEQUENCE: 64

```
ccggcctgct tcagcaggct gaagttggtg gctccggatc cggaccgctt ggcccggctg    60
```

-continued

```
gaccacagcc gcag                                                     74

<210> SEQ ID NO 65
<211> LENGTH: 66
<212> TYPE: DNA
<213> ORGANISM: Artificial Sequence
<220> FEATURE:
<223> OTHER INFORMATION: Synthetic

<400> SEQUENCE: 65
agcctgctga agcaggccgg cgacgtggag gagaaccccg gcccgatggg cacaaggttg     60
ttcttc                                                              66

<210> SEQ ID NO 66
<211> LENGTH: 42
<212> TYPE: DNA
<213> ORGANISM: Artificial Sequence
<220> FEATURE:
<223> OTHER INFORMATION: Synthetic

<400> SEQUENCE: 66
gaggggctgc gggtccgtgc agacccact gtgcacctcc tt                        42

<210> SEQ ID NO 67
<211> LENGTH: 42
<212> TYPE: DNA
<213> ORGANISM: Artificial Sequence
<220> FEATURE:
<223> OTHER INFORMATION: Synthetic

<400> SEQUENCE: 67
aaggaggtgc acagtggggt ctgcacggac ccgcagcccc tc                       42

<210> SEQ ID NO 68
<211> LENGTH: 28
<212> TYPE: DNA
<213> ORGANISM: Artificial Sequence
<220> FEATURE:
<223> OTHER INFORMATION: Synthetic

<400> SEQUENCE: 68 ttttttgaa ttctcagaaa tcctttct                                       28

<210> SEQ ID NO 69
<211> LENGTH: 44
<212> TYPE: DNA
<213> ORGANISM: Artificial Sequence
<220> FEATURE:
<223> OTHER INFORMATION: Synthetic

<400> SEQUENCE: 69
ggttctgggt tctggatatt tggtttaaca gagagtttag tgcc                     44

<210> SEQ ID NO 70
<211> LENGTH: 44
<212> TYPE: DNA
<213> ORGANISM: Artificial Sequence
<220> FEATURE:
<223> OTHER INFORMATION: Synthetic

<400> SEQUENCE: 70
ggcactaaac tctctgttaa accaaatatc cagaacccag aacc                     44

<210> SEQ ID NO 71
```

-continued

```
<211> LENGTH: 77
<212> TYPE: DNA
<213> ORGANISM: Artificial Sequence
<220> FEATURE:
<223> OTHER INFORMATION: Synthetic

<400> SEQUENCE: 71
ccggcctgct tcagcaggct gaagttggtg gctccggatc cggaccgctt ggcccgactg      60
gaccacagcc tcagcgt                                                    77

<210> SEQ ID NO 72
<211> LENGTH: 48
<212> TYPE: DNA
<213> ORGANISM: Artificial Sequence
<220> FEATURE:
<223> OTHER INFORMATION: Synthetic

<400> SEQUENCE: 72
tggagtcaca tttctcagat cctctacaac agtgagccaa cttccctc                  48

<210> SEQ ID NO 73
<211> LENGTH: 48
<212> TYPE: DNA
<213> ORGANISM: Artificial Sequence
<220> FEATURE:
<223> OTHER INFORMATION: Synthetic

<400> SEQUENCE: 73
gagggaagtt ggctcactgt tgtagaggat ctgagaaatg tgactcca                  48

<210> SEQ ID NO 74
<211> LENGTH: 27
<212> TYPE: DNA
<213> ORGANISM: Artificial Sequence
<220> FEATURE:
<223> OTHER INFORMATION: Synthetic

<400> SEQUENCE: 74
gactacgtag cggccgctca tgaattc                                         27
```

T CELL RECEPTORS AND RELATED MATERIALS AND METHODS OF USE

CROSS-REFERENCE TO RELATED APPLICATIONS

This patent application is a divisional of U.S. patent application Ser. No. 13/146,531, which is a U.S. National Phase of International Patent Application No. PCT/US10/21909, filed Jan. 25, 2010, which claims the benefit of U.S. Provisional Patent Application No. 61/147,846, filed Jan. 28, 2009, each of which is incorporated by reference herein in its entirety.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 72,578 Byte ASCII Text) file named "716360ST25.TXT.," dated Mar. 12, 2014.

BACKGROUND OF THE INVENTION

Cancer remains one of the leading causes of death in developed countries. The American Cancer Society estimates that skin cancer, for example, is the most common of cancers, and melanoma, in particular, causes a large majority of skin cancer deaths (American Cancer Society, *Cancer Reference Guide: Skin Cancer—Melanoma* 2008; www.cancer.org). Prognosis for many types of cancers may be poor. Glioblastoma, for example, accounts for approximately 19% of all primary brain tumors, and the average five-year survival rate is less than 4% (Central Brain Tumor Registry of the United States, *Primary Brain Tumors in the United States*, Data collected 2000-2004 (2007-2008)).

Some cancers, for example, glioma and melanoma, have been considered to be immunogenic. In particular, tyrosinase has been demonstrated as an antigen in several human cancers, including melanoma and glioma (Kawakami et al., *J. Immunother.*, 21(4):237-46 (1998); Zhang et al., Clin. Cancer Res., 13:566-75 (2007)). Accordingly, tyrosinase may be a target for immunotherapy.

In spite of considerable research into immunotherapy, there is a need in the art for improved compositions and methods for treating and/or preventing cancer.

BRIEF SUMMARY OF THE INVENTION

The invention provides a T cell receptor (TCR) having antigenic specificity for a cancer antigen, e.g., tyrosinase. The TCR can comprise specified amino acid sequences as described herein. The inventive TCRs may be modified or native, i.e., unmodified.

For instance, an embodiment of the invention provides an isolated or purified TCR that comprises the amino acid sequence of SEQ ID NO: 7, both SEQ ID NOs: 7 and 8, SEQ ID NOs: 1-3 and 9, or SEQ ID NOs: 1-6 and 9-10.

In another embodiment, the invention provides a TCR that comprises the amino acid sequence of SEQ ID NOs: 1-6 and 14-15; SEQ ID NOs: 1-3 and SEQ ID NO: 18; SEQ ID NOs: 4-6 and SEQ ID NO: 19; SEQ ID NOs: 1-6 and 18-19; SEQ ID NOs: 1-6, 10 and 18; or SEQ ID NOs: 1-6, 9, and 19; SEQ ID NOs: 1-6 and 22-23; SEQ ID NO: 55; SEQ ID NOs: 55 and 8; SEQ ID NOs: 55 and 9; or SEQ ID NOs: 55 and 8-10.

The invention further provides embodiments including polypeptides and proteins, as well as related nucleic acids, recombinant expression vectors, host cells, populations of cells, and pharmaceutical compositions relating to the TCRs of the invention.

Methods of detecting the presence of cancer in a host and methods of treating or preventing cancer in a host are further provided by the invention. The inventive method of detecting the presence of cancer in a host comprises (i) contacting a sample comprising cells of the cancer with any of the inventive TCRs, polypeptides, proteins, nucleic acids, recombinant expression vectors, host cells, or populations of host cells, described herein, thereby forming a complex, and (ii) detecting the complex, wherein detection of the complex is indicative of the presence of cancer in the host.

The inventive method of treating or preventing cancer in a host comprises administering to the host any of the TCRs, polypeptides, or proteins described herein, any nucleic acid or recombinant expression vector comprising a nucleotide sequence encoding any of the TCRs, polypeptides, proteins described herein, or any host cell or population of host cells comprising a recombinant vector which encodes any of the TCRs, polypeptides, or proteins described herein, in an amount effective to treat or prevent cancer in the host.

BRIEF DESCRIPTION OF THE SEVERAL VIEWS OF THE DRAWING(S)

FIG. 1 is a graph of the % specific lysis of target cells (526Mel) by CD4/CD8 sorted populations of effector cells at the indicated effector cell:target cell (E:T) ratios. The effector cells included PBL transduced with MART-1 F4 TCR (CD4) (dashed line with □), MART-1 F4 (CD8) (solid line with ■), gp100 TCR (CD4) (solid line with Δ), gp100 (CD8) (solid line with ▲), unmodified tyrosinase TCR (CD4) (solid line with ◊), unmodified tyrosinase TCR (CD8) (solid line with ♦), murine-human chimera tyrosinase TCR (CD4) (solid line with ○), and murine-human chimera tyrosinase TCR (CD8) (solid line with ●).

FIG. 2 is a graph of the % specific lysis of target cells (624Mel) by CD4/CD8 sorted populations of effector cells at the indicated effector cell:target cell (E:T) ratios. The effector cells included PBL transduced with MART-1 F4 TCR (CD4) (dashed line with □), MART-1 F4 (CD8) (solid line with ■), gp100 TCR (CD4) (solid line with Δ), gp100 (CD8) (solid line with ▲), unmodified tyrosinase TCR (CD4) (solid line with ◊), unmodified tyrosinase TCR (CD8) (solid line with ♦), murine-human chimera tyrosinase TCR (CD4) (solid line with ○), and murine-human chimera tyrosinase TCR (CD8) (solid line with ●).

FIG. 3 is a graph of the % specific lysis of target cells (888Mel) by CD4/CD8 sorted populations of effector cells at the indicated effector cell:target cell (E:T) ratios. The effector cells included PBL transduced with MART-1 F4 TCR (CD4) (dashed line with □), MART-1 F4 (CD8) (solid line with ■), gp100 TCR (CD4) (solid line with Δ), gp100 (CD8) (solid line with ▲), unmodified tyrosinase TCR (CD4) (solid line with ◊), unmodified tyrosinase TCR (CD8) (solid line with ♦), murine-human chimera tyrosinase TCR (CD4) (solid line with ○), and murine-human chimera tyrosinase TCR (CD8) (solid line with ●).

FIG. 4 is a graph of the % specific lysis of target cells (526Mel) by CD4/CD8 sorted populations of effector cells at the indicated effector cell:target cell (E:T) ratios. The effector cells included PBL transduced with unmodified tyrosinase TCR (CD4) (dashed line with □), unmodified tyrosinase TCR (CD8) (solid line with ●), murine-human chimera tyrosinase TCR (CD4) (solid line with ▲), murine-human chimera tyrosinase TCR (CD8) (solid line with ▲), MART-1 F4 (CD4) (solid line with ◇), MART-1 F4 (CD8) (solid line with ■), gp100 (CD4) (dashed line with ○), and gp100 (CD8) (solid line with |).

FIG. 5 is a graph of the % specific lysis of target cells (624Mel) by CD4/CD8 sorted populations of effector cells at the indicated effector cell:target cell (E:T) ratios. The effector cells included PBL transduced with unmodified tyrosinase TCR (CD4) (dashed line with □), unmodified tyrosinase TCR (CD8) (solid line with ●), murine-human chimera tyrosinase TCR (CD4) (solid line with Δ), murine-human chimera tyrosinase TCR (CD8) (solid line with ▫), MART-1 F4 (CD4) (solid line with ◇), MART-1 F4 (CD8) (solid line with ■), gp100 (CD4) (dashed line with ○), and gp100 (CD8) (solid line with |).

FIG. 6 is a graph of the % specific lysis of target cells (888Mel) by CD4/CD8 sorted populations of effector cells at the indicated effector cell:target cell (E:T) ratios. The effector cells included PBL transduced with unmodified tyrosinase TCR (CD4) (dashed line with □), unmodified tyrosinase TCR (CD8) (solid line with ●), murine-human chimera tyrosinase TCR (CD4) (solid line with Δ), murine-human chimera tyrosinase TCR (CD8) (solid line with ▫), MART-1 F4 (CD4) (solid line with ◇), MART-1 F4 (CD8) (solid line with ■), gp100 (CD4) (dashed line with ○), and gp100 (CD8) (solid line with |).

DETAILED DESCRIPTION OF THE INVENTION

Figure 1:
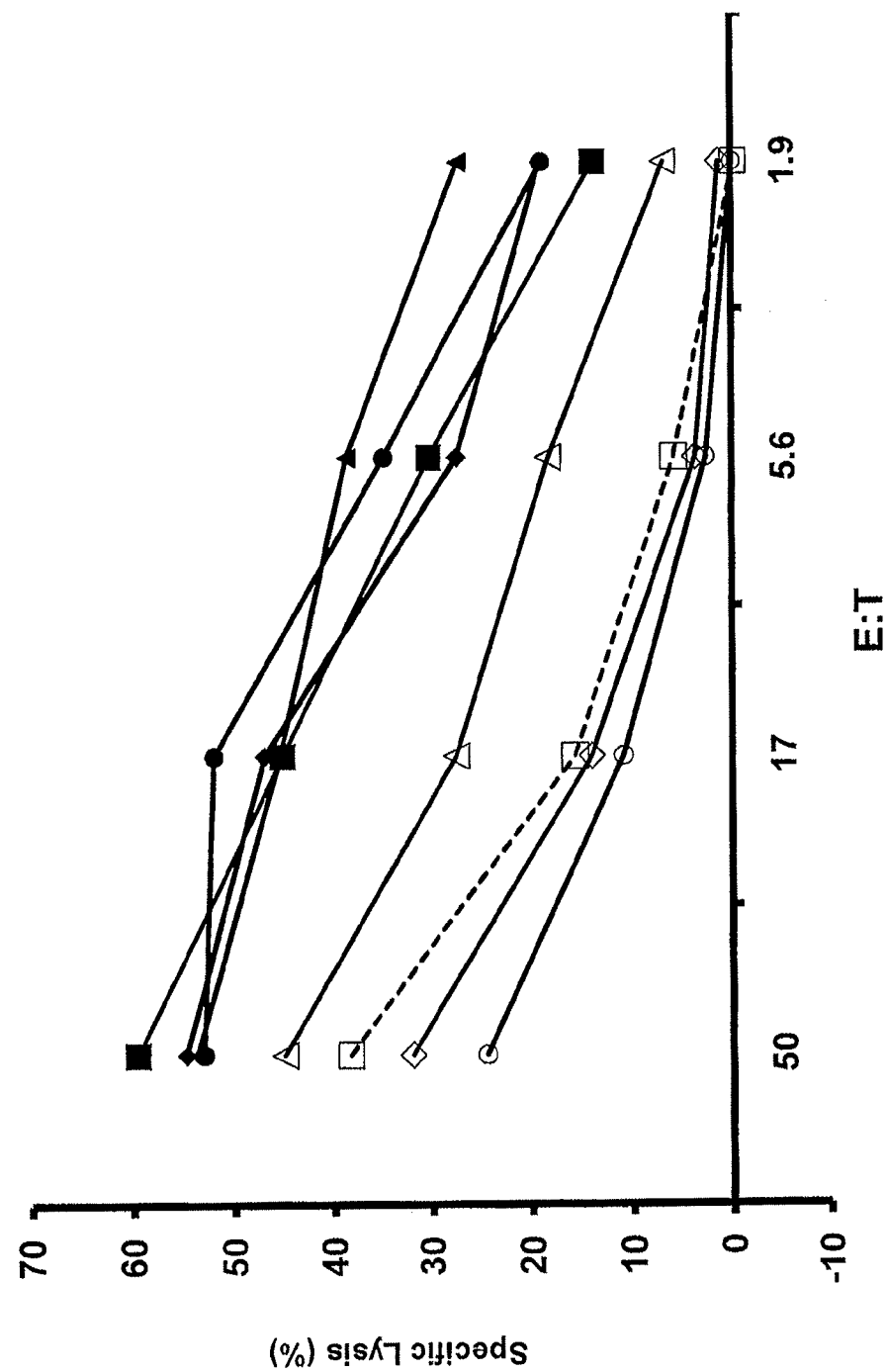

The invention provides a T cell receptor (TCR) having antigenic specificity for a cancer antigen, e.g., tyrosinase. Embodiments of the inventive TCRs (and functional portions thereof) described herein include both modified and native, i.e., unmodified TCRs (and functional portions thereof).

The phrase "having antigenic specificity" as used herein means that the TCR can specifically bind to and immunologically recognize the cancer antigen, such that binding of the TCR to the cancer antigen elicits an immune response.

The term "cancer antigen" as used herein refers to any molecule (e.g., protein, peptide, lipid, carbohydrate, etc.) expressed by a tumor cell or cancer cell, such that the antigen is associated with the tumor or cancer. The cancer antigen can additionally be expressed by normal, non-tumor, or non-cancerous cells. Also, the cancer antigen can additionally be expressed by cells of a different state of development or maturation. For instance, the cancer antigen can be additionally expressed by cells of the embryonic or fetal stage, which cells are not normally found in an adult host. Alternatively, the cancer antigen can be additionally expressed by stem cells or precursor cells, which cells are not normally found in an adult host.

The cancer antigen can be an antigen expressed by any cell of any cancer or tumor, including the cancers and tumors described herein. The cancer antigen may be a cancer antigen of only one type of cancer or tumor, such that the cancer antigen is associated with or characteristic of only one type of cancer or tumor. Alternatively, the cancer antigen may be a cancer antigen (e.g., may be characteristic) of more than one type of cancer or tumor. In a preferred embodiment of the invention, the cancer antigen is a glioma cancer antigen or a melanoma antigen. In a more preferred embodiment, the cancer antigen is tyrosinase tumor antigen.

Without being bound to any particular theory, the inventive TCRs are able to recognize a cancer antigen in an HLA-A2-restricted manner. By "HLA-A2-restricted manner" as used herein means that the TCR, upon binding to the cancer antigen, can elicit an immune response in the presence of binding to an HLA-A2 molecule.

Furthermore, without being bound to any particular theory, the inventive TCRs are able to recognize a cancer antigen in a CD8- and/or CD4-independent manner. By "CD8- and/or CD4-independent manner," it is meant that the inventive TCRs, upon binding to a cancer antigen, can elicit an immune response in the absence of a functional or nonfunctional CD8 or CD4 molecule, or the absence of both a functional or nonfunctional CD8 and a CD4 molecule, on the cell expressing the inventive TCR. The inventive TCRs do not have a preference for CD8 or CD4 and can function in the presence of either a CD8 or CD4 molecule.

The invention provides a TCR comprising two polypeptides (i.e., polypeptide chains), such as an α chain of a TCR, a β chain of a TCR, a γ chain of a TCR, a δ chain of a TCR, or a combination thereof. The polypeptides of the inventive TCR can comprise any amino acid sequence, provided that the TCR has antigenic specificity for a cancer antigen.

In a preferred embodiment of the invention, the TCR comprises two polypeptide chains, each of which comprises a variable region comprising a complementarity determining region (CDR) 1, a CDR2, and a CDR3 of a TCR. Preferably, the first polypeptide chain comprises a CDR1 comprising the amino acid sequence of SEQ ID NO: 1 (CDR1 of α chain), a CDR2 comprising the amino acid sequence of SEQ ID NO: 2 (CDR2 of α chain), and a CDR3 comprising the amino acid sequence of SEQ ID NO: 3 (CDR3 of α chain), and the second polypeptide chain comprises a CDR1 comprising the amino acid sequence of SEQ ID NO: 4 (CDR1 of β chain), a CDR2 comprising the amino acid sequence of SEQ ID NO: 5 (CDR2 of β chain), and a CDR3 comprising the amino acid sequence of SEQ ID NO: 6 (CDR3 of β chain). In this regard, the inventive TCRs described herein can comprise the amino acid sequences selected from the group consisting of SEQ ID NOs: 1-3, 4-6, and 1-6. Preferably the TCR comprises the amino acid sequences of SEQ ID NOs: 1-6.

Alternatively or additionally, the TCR can comprise an amino acid sequence of a variable region of a TCR comprising the CDRs set forth above. In this regard, any of the embodiments of the inventive TCRs described herein can comprise the amino acid sequence of SEQ ID NO: 7 or 55 (the variable region of an α chain) or 8 (the variable region of a β chain), both SEQ ID NOs: 7 and 8, or both SEQ ID NOs: 55 and 8. Preferably, the inventive TCR comprises the amino acid sequences of both SEQ ID NOs: 7 and 8 or both SEQ ID NOs: 55 and 8.

Alternatively or additionally, the unmodified TCR comprises two polypeptide chains, each of which comprises a constant region. In this regard, the first polypeptide chain comprises the amino acid sequence of SEQ ID NO: 9 (constant region of an α chain), and the second polypeptide chain comprises SEQ ID NO: 10 (constant region of a β chain). Preferably, the unmodified TCR comprises both SEQ ID NOs: 9 and 10. The unmodified TCRs of the invention may include the constant region in addition to any of the CDRs and/or variable regions described herein. In this regard, the unmodified TCR can comprise a first polypeptide chain comprising SEQ ID NOs: 1-3 and 9 and a second polypeptide chain comprising SEQ ID NOs: 4-6 and 10. Preferably, the unmodified TCR comprises the amino acid sequences of SEQ ID NOs: 1-6 and 9-10.

Alternatively or additionally, the unmodified TCR comprises an α chain of a TCR and a β chain of a TCR. Each of the α chain and β chain of the inventive unmodified TCR can independently comprise any amino acid sequence. Preferably, the α chain comprises the variable region of an α chain as set forth above. In this regard, an embodiment of the inventive unmodified TCR can comprise the amino acid sequence of SEQ ID NO: 11. An inventive TCR of this type can be paired with any β chain of a TCR. Preferably, the β chain of the inventive TCR comprises the variable region of a β chain as set forth above. In this regard, an embodiment of the inventive unmodified TCR can comprise the amino acid sequence of SEQ ID NO: 12. The inventive unmodified TCR, therefore, can comprise the amino acid sequence of SEQ ID NO: 11, 12, or both SEQ ID NOs: 11 and 12. Preferably, the inventive unmodified TCR comprises the amino acid sequences of both SEQ ID NOs: 11 and 12.

An embodiment of the invention also provides a TCR comprising an α chain comprising the amino acid sequence of both SEQ ID NOs: 55 and 9. An inventive TCR of this type can be paired with any β chain of a TCR. Preferably, the inventive TCR comprises the amino acid sequences of each of SEQ ID NOs: 55, 9, and 12.

The invention also provides modified amino acid sequences that encode modified TCRs, modified polypeptides, or modified proteins. In particular, the modified amino acid sequences include modified constant regions that may be combined with any of the CDR regions and/or variable regions described herein to provide a modified TCR. In some embodiments, the modified TCRs provide an increased reactivity against a cancer antigen and/or improved expression of the TCR in a cell as compared to an unmodified amino acid sequence. The modified TCRs may, optionally, be isolated or purified.

In one embodiment of the modified TCR, the modified amino acid sequence includes cysteine substitutions in the constant region of one or both of the α and β chains to provide a cysteine-substituted tyrosinase TCR. Opposing cysteines in the α and the β chains provide a second disulfide bond that links the constant regions of the α and the β chains of the modified TCR to one another and which is not present in the native, unmodified TCR, which has only one disulfide bond linking the constant regions of the α and the β chains.

In general, the modified amino acid sequences of the constant regions of TCR α and β chains, SEQ ID NOs: 14 and 15, respectively, correspond with all or portions of the native, unmodified amino acid sequences SEQ ID NOs: 9 and 10, respectively, with SEQ ID NOs: 14 and 15 having at least one substitution when compared to SEQ ID NOs: 9 and 10, respectively. One or both of the native Thr48 of SEQ ID NO: 9 and the native Ser57 of SEQ ID NO: 10 may be substituted with Cys. Preferably, both of the native Thr48 of SEQ ID NO: 9 and the native Ser57 of SEQ ID NO: 10 are substituted with Cys. The cysteine-substituted tyrosinase TCRs of the invention may include the modified constant region in addition to any of the CDRs and/or variable regions described herein. In this regard, the cysteine-substituted tyrosinase TCR can comprise a first polypeptide chain comprising SEQ ID NOs: 1-3 and 14 and a second polypeptide chain comprising SEQ ID NOs: 4-6 and 15. Preferably, the cysteine-substituted tyrosinase TCR comprises the amino acid sequences of SEQ ID NOs: 1-6 and 14-15.

In another embodiment of the cysteine-substituted tyrosinase TCR, the modified amino acid sequences of the TCR α and β chains, SEQ ID NOs: 16 and 17, respectively, correspond with all or portions of the native, unmodified amino acid sequences SEQ ID NOs: 11 and 12, respectively, with SEQ ID NOs: 16 and 17 having at least one substitution when compared to SEQ ID NOs: 11 and 12, respectively. One or both of the native Thr178 of SEQ ID NO: 11 and the native Ser195 of SEQ ID NO: 12 may be substituted with Cys. Preferably, both of the native Thr178 of SEQ ID NO: 11 and the native Ser195 of SEQ ID NO: 12 are substituted with Cys.

In another embodiment of the modified TCR, the modified amino acid sequence includes a murine constant region in place of the unmodified, native human constant region of one or both of the α and the β chains to provide a murine-human chimera tyrosinase TCR. In general, the modified amino acid sequences of the constant regions of TCR α and β chains, SEQ ID NOs: 18 and 19, respectively, correspond with all or portions of the native, unmodified human amino acid sequences SEQ ID NOs: 9 and 10, respectively, with SEQ ID NOs: 18 and 19 including a sequence that corresponds to the murine constant region in place of the human constant region sequences of SEQ ID NOs: 9 and 10, respectively. The murine-human chimera tyrosinase TCRs of the invention may include the modified constant region in addition to any of the CDRs and/or variable regions described herein. In this regard, the murine-human chimera tyrosinase TCR can comprise a first polypeptide chain comprising SEQ ID NOs: 1-3 and 18 and a second polypeptide chain comprising SEQ ID NOs: 4-6 and 19. In some embodiments, the murine-human chimera tyrosinase TCR can comprise a first polypeptide chain including a murine constant region and a second polypeptide chain including an unmodified constant region. In this regard, the murine-human chimera tyrosinase TCR can comprise a first polypeptide chain comprising SEQ ID NOs: 1-3 and 9 and a second polypeptide chain comprising SEQ ID NOs: 4-6 and 19 or a first polypeptide chain comprising SEQ ID NOs: 1-3 and 18 and a second polypeptide chain comprising SEQ ID NOs: 4-6 and 10. Preferably, the murine-human chimera tyrosinase TCR comprises the amino acid sequences of SEQ ID NOs: 1-6 and 18-19. Accordingly, modified constant region sequences SEQ ID NOs: 18 and 19 may provide a murine-human chimera tyrosinase TCR when combined with any of the CDR regions or variable regions described herein.

In another embodiment of the murine-human chimera tyrosinase TCR, the modified amino acid sequences of the TCR α and β chains, SEQ ID NOs: 20 and 21, respectively, correspond with all or portions of the native, unmodified human amino acid sequences SEQ ID NOs: 11 and 12, respectively, with SEQ ID NOs: 20 and 21 including a sequence that corresponds to the murine constant region in place of the human constant region sequences of SEQ ID NOs: 11 and 12, respectively. In this regard, the modified TCR can comprise a first polypeptide chain comprising SEQ ID NO: 20 and a second polypeptide chain comprising SEQ ID NO: 21. In some embodiments, the TCR can comprise a first polypeptide chain including a murine constant region and a second polypeptide chain including an unmodified constant region. In this regard, the modified TCR can comprise a first polypeptide chain comprising SEQ ID NO: 20 and a second polypeptide chain comprising SEQ ID NO: 12 or a first polypeptide chain comprising SEQ ID NO: 11 and a second polypeptide chain comprising SEQ ID NO: 21. Preferably, the modified TCR comprises the amino acid sequences of SEQ ID NOs: 20 and 21.

In still another embodiment of the modified TCR, the modified amino acid sequence includes a murine constant region in place of the unmodified, native human constant region of one or both of the α and the β chains in addition to cysteine substitutions in the constant region of one or both of the α and β chains to provide a cysteine-substituted murine-human chimera tyrosinase TCR. Opposing cysteines in the α and the β chains provide a second disulfide bond that links the constant regions of the α and the β chains of the modified TCR to one another and which is not present in the native, unmodified murine TCR constant region, which has only one disulfide bond linking the constant regions of the α and the β chains. In general, the modified amino acid sequences of the constant regions of TCR α and β chains, SEQ ID NOs: 22 and 23, respectively, correspond with all or portions of the native, unmodified human amino acid sequences SEQ ID NOs: 9 and 10, respectively, with SEQ ID NOs: 22 and 23 having a sequence that corresponds to the murine constant region in place of the human constant region sequences of SEQ ID NOs: 9 and 10, respectively, and having at least one substitution when compared to the unmodified murine constant regions of SEQ ID NOs: 18 and 19, respectively. One or both of the native murine Thr48 of SEQ ID NO: 18 and the native murine Ser57 of SEQ ID NO: 19 may be substituted with Cys. Preferably, both of the native murine Thr48 of SEQ ID NO: 18 and the native murine Ser57 of SEQ ID NO: 19 are substituted with Cys.

The cysteine-substituted murine-human chimera tyrosinase TCRs of the invention may include the modified constant region in addition to any of the CDRs and/or variable regions described herein. In this regard, the cysteine-substituted murine-human chimera tyrosinase TCR can comprise a first polypeptide chain comprising SEQ ID NOs: 1-3 and 22 and a second polypeptide chain comprising SEQ ID NOs: 4-6 and 23. Preferably, the cysteine-substituted murine-human chimera tyrosinase TCR comprises the amino acid sequences of SEQ ID NOs: 1-6 and 22-23. Accordingly, modified constant region sequences SEQ ID NOs: 22 and 23 may provide a cysteine-substituted murine-human chimera tyrosinase TCR when combined with any of the CDR regions or variable regions described herein.

In another embodiment of the cysteine-substituted murine-human chimera tyrosinase TCR, the modified amino acid sequences of the TCR α and β chains, SEQ ID NOs: 24 and 25, correspond with all or portions of the native, unmodified human amino acid sequences SEQ ID NOs: 11 and 12, respectively, with SEQ ID NOs: 24 and 25 having a sequence that corresponds to the murine constant region in place of the human constant region sequences of SEQ ID NOs: 11 and 12 and having at least one substitution when compared to the unmodified murine constant regions of SEQ ID NOs: 20 and 21, respectively. One or both of the native murine Thr178 of SEQ ID NO: 20 and the native murine Ser195 of SEQ ID NO: 21 may be substituted with Cys. Preferably, both of the native murine Thr178 of SEQ ID NO: 20 and the native murine Ser195 of SEQ ID NO: 21 are substituted with Cys.

Embodiments of modified TCRs comprise two polypeptide chains, each of which comprises a variable region comprising a complementarity determining region (CDR) 1, a CDR2, and a CDR3 of a TCR. The modified TCRs may comprise one or more of the CDRs described for the unmodified TCRs described herein. Preferably, the first polypeptide chain comprises a CDR1 comprising the amino acid sequence of SEQ ID NO: 1 (CDR1 of α chain), a CDR2 comprising the amino acid sequence of SEQ ID NO: 2 (CDR2 of α chain), and a CDR3 comprising the amino acid sequence of SEQ ID NO: 3 (CDR3 of α chain), and the second polypeptide chain comprises a CDR1 comprising the amino acid sequence of SEQ ID NO: 4 (CDR1 of β chain), a CDR2 comprising the amino acid sequence of SEQ ID NO: 5 (CDR2 of β chain), and a CDR3 comprising the amino acid sequence of SEQ ID NO: 6 (CDR3 of β chain). In this regard, an embodiment of the inventive modified TCRs can comprise the amino acid sequences selected from the group consisting of SEQ ID NOs: 1-3, 4-6, and 1-6. Preferably, the inventive modified TCRs comprise each of the amino acid sequences SEQ ID NO: 1-6.

Alternatively or additionally, the modified TCRs can comprise an amino acid sequence of a variable region of a TCR comprising the CDRs set forth above. The modified TCRs may comprise one or more of the variable regions described herein. In this regard, an embodiment of the inventive TCRs can comprise the amino acid sequence of SEQ ID NO: 7 or 55 (the variable region of an α chain) or 8 (the variable region of a β chain), both SEQ ID NOs: 7 and 8, or both SEQ ID NOs: 55 or 8. Preferably, the inventive TCRs comprise the amino acid sequences of both SEQ ID NOs: 7 and 8 or both SEQ ID NOs: 55 and 8.

Alternatively or additionally, the modified TCRs can comprise a modified α chain of a TCR and/or a modified β chain of a TCR. Each of the α chain and β chain of the inventive modified TCRs can independently comprise any amino acid sequence. Preferably, the modified α chain comprises a modified constant region of an α chain as set forth above. In this regard, the an embodiment of the inventive modified α chain of the modified TCR can comprise the amino acid sequence of SEQ ID NOs: 14, 18, or 22 (modified constant regions of α chain). An inventive modified α chain of this type can be paired with any β chain of a TCR. Preferably, the modified β chain comprises a modified constant region of a β chain as set forth above. In this regard, an embodiment of the inventive modified β chain of the modified TCR can comprise the amino acid sequence of SEQ ID NO: 15, 19, or 23 (modified constant regions of β chain). The inventive TCR, therefore, can comprise the amino acid sequence of SEQ ID NO: 14, 15, 18, 19, 22, or 23, both SEQ ID NOs: 14 and 15, both SEQ ID NOs: 18 and 19, or both SEQ ID NOs: 22 and 23. Preferably, the inventive modified TCR comprises the amino acid sequences of both SEQ ID NOs: 14 and 15, both SEQ ID NOs: 18 and 19, or both SEQ ID NOs: 22 and 23.

Also provided by the invention is an isolated or purified polypeptide comprising a functional portion of any of the TCRs described herein. The term "polypeptide" as used herein includes oligopeptides and refers to a single chain of amino acids connected by one or more peptide bonds.

With respect to the inventive polypeptides, the functional portion can be any portion comprising contiguous amino acids of the TCR of which it is a part, provided that the functional portion specifically binds to the cancer antigen. The term "functional portion" when used in reference to a TCR refers to any part or fragment of the TCR of the invention, which part or fragment retains the biological activity of the TCR of which it is a part (the parent TCR). Functional portions encompass, for example, those parts of a TCR that retain the ability to specifically bind to the cancer antigen (e.g., in a CD8- and/or CD4-independent manner), or detect, treat, or prevent cancer, to a similar extent, the same extent, or to a higher extent, as the parent TCR. In reference to the parent TCR, the functional portion can comprise, for instance, about 10%, 25%, 30%, 50%, 68%, 80%, 90%, 95%, or more, of the parent TCR.

The functional portion can comprise additional amino acids at the amino or carboxy terminus of the portion, or at both termini, which additional amino acids are not found in the amino acid sequence of the parent TCR. Desirably, the additional amino acids do not interfere with the biological function of the functional portion, e.g., specifically binding to a cancer antigen in a CD8- and/or CD4-independent manner, having the ability to detect cancer, treat or prevent cancer, etc. More desirably, the additional amino acids enhance the biological activity, as compared to the biological activity of the parent TCR.

The polypeptide can comprise a functional portion of either or both of the α and β chains of the TCRs of the invention, such as a functional portion comprising one of more of CDR1, CDR2, and CDR3 of the variable region(s) of the α chain and/or β chain of a TCR of the invention. In this regard, the an embodiment of the polypeptide can comprise a functional portion comprising the amino acid sequence of SEQ ID NOs: 1 (CDR1 of α chain), 2 (CDR2 of α chain), 3 (CDR3 of α chain), 4 (CDR1 of β chain), 5 (CDR2 of β chain), 6 (CDR3 of β chain), or a combination thereof. Preferably, the inventive polypeptide comprises a functional portion comprising SEQ ID NOs: 1-3, 4-6, or all of SEQ ID NOs: 1-6. More preferably, the polypeptide comprises a functional portion comprising the amino acid sequences of SEQ ID NOs: 1-6.

Alternatively or additionally, the inventive polypeptide can comprise, for instance, a functional portion comprising the variable region of the inventive TCR comprising a combination of the CDR regions set forth above. In this regard, an embodiment of the polypeptide can comprise the amino acid sequence of SEQ ID NO: 7 or 55 (the variable region of an α chain), 8 (the variable region of a β chain), both SEQ ID NOs: 7 and 8, or both SEQ ID NOs: 55 and 8. Preferably, the polypeptide comprises the amino acid sequence of SEQ ID NO: 7 or 55, both SEQ ID NOs: 7 and 8, or both SEQ ID NOs: 55 and 8.

Alternatively or additionally, the inventive polypeptide can comprise a constant region. In this regard, an embodiment of the polypeptide can comprise the amino acid sequence of SEQ ID NOs: 9, 14, 18, or 22 (constant region of an α chain), SEQ ID NOs: 10, 15, 19, or 23 (constant region of a β chain), or SEQ ID NOs: 9-10, SEQ ID NOs: 14-15, SEQ ID NOs: 18-19, or SEQ ID NOs: 22-23.

Alternatively or additionally, the inventive polypeptide can comprise the entire length of an α or β chain of one of the TCRs described herein. In this regard, an embodiment of the inventive polypeptide can comprise an amino acid sequence of SEQ ID NOs: 11, 12, 16, 17, 20, 21, 24, 25, or SEQ ID NOs: 55 and 9. Alternatively, the polypeptide of the invention can comprise α and β chains of the TCRs described herein. For example, the inventive polypeptide can comprise both amino acid sequences of SEQ ID NOs: 11 and 12, both SEQ ID NOs: 16 and 17, both SEQ ID NOs: 20 and 21, both SEQ ID NOs: 24 and 25, or all of SEQ ID NOs: 9, 12, and 55.

The invention further provides an isolated or purified protein comprising at least one of the polypeptides described herein. By "protein" is meant a molecule comprising one or more polypeptide chains.

The protein of the invention can comprise any one or more of the polypeptide chains described herein. In this regard, the protein of an embodiment of the invention can comprise a first polypeptide chain comprising the amino acid sequence of SEQ ID NOs: 1-3 and 9, SEQ ID NO: 7, or SEQ ID NO: 55 and a second polypeptide chain comprising the amino acid sequence of SEQ ID NOs: 4-6 or SEQ ID NO: 8. The protein of the invention can, for example, comprise a first polypeptide chain comprising the amino acid sequence of SEQ ID NO: 11, 16, 20, 24, or SEQ ID NOs: 55 and 9 and a second polypeptide chain comprising the amino acid sequence of SEQ ID NO: 12, 17, 21, or 25. In this instance, the protein of the invention can be a TCR.

The inventive protein can be a fusion protein. For example, a protein of the invention can comprise a single polypeptide chain comprising both an α chain and a β chain. In this regard, the protein of an embodiment of the invention can comprise a single polypeptide chain comprising an α chain comprising any one or more of SEQ ID NOs: 11, 16, 20, 24, and SEQ ID NOs: 55 and 9 and a β chain comprising any one or more of SEQ ID NOs: 12, 17, 21, or 25. Alternatively, the first and/or second polypeptide chain(s) of the protein further comprise(s) other amino acid sequences, e.g., an amino acid sequence encoding an immunoglobulin or a portion thereof. In this regard, the invention also provides a fusion protein comprising at least one of the inventive polypeptides described herein along with at least one other polypeptide. The other polypeptide can exist as a separate polypeptide of the fusion protein, or can exist as a polypeptide, which is expressed in frame (in tandem) with one of the inventive polypeptides described herein. The other polypeptide can encode any peptidic or proteinaceous molecule, or a portion thereof, including, but not limited to an immunoglobulin, CD3, CD4, CD8, an MHC molecule, a CD1 molecule, e.g., CD1a, CD1b, CD1c, CD1d, etc.

The fusion protein can comprise one or more copies of the inventive polypeptide and/or one or more copies of the other polypeptide. For instance, the fusion protein can comprise 1, 2, 3, 4, 5, or more, copies of the inventive polypeptide and/or of the other polypeptide. Suitable methods of making fusion proteins are known in the art, and include, for example, recombinant methods. See, for instance, Choi et al., *Mol. Biotechnol.* 31: 193-202 (2005).

Included in the scope of the invention are functional variants of the inventive TCRs, polypeptides, and proteins described herein. The term "functional variant" as used herein refers to a TCR, polypeptide, or protein having substantial or significant sequence identity or similarity to a parent TCR, polypeptide, or protein, which functional variant retains the biological activity of the TCR, polypeptide, or protein of which it is a variant. Functional variants encompass, for example, those variants of the TCR, polypeptide, or protein described herein (the parent TCR, polypeptide, or protein) that retain the ability to specifically bind to the cancer antigen for which the parent TCR has antigenic specificity or to which the parent polypeptide or protein specifically binds (e.g., in a CD8- and/or CD4-independent manner), to a similar extent, the same extent, or to a higher extent, as the parent TCR, polypeptide, or protein. In reference to the parent TCR, polypeptide, or protein, the functional variant can, for instance, be at least about 30%, 50%, 75%, 80%, 90%, 98% or more identical in amino acid sequence to the parent TCR, polypeptide, or protein.

The TCR, polypeptide, or protein can consist essentially of the specified amino acid sequence or sequences described herein, such that other components of the functional variant, e.g., other amino acids, do not materially change the biological activity of the functional variant. In this regard, an embodiment of the inventive TCR, polypeptide, or protein can, for example, consist essentially of the amino acid sequence of SEQ ID NO: 11, 12, 16, 17, 20, 21, 24, 25, both SEQ ID NOs: 55 and 9, both SEQ ID NOs: 11 and 12, both SEQ ID NOs: 16 and 17, both SEQ ID NOs: 20 and 21, both SEQ ID NOs: 24 and 25, or each of SEQ ID NOs: 55, 9, and 12. Also, for instance, the inventive TCRs, polypeptides, or proteins can consist essentially of the amino acid sequence(s) of SEQ ID NO: 7, 8, 55, both SEQ ID NOs: 7 and 8, or both SEQ ID NOs: 55 and 8. Furthermore, the inventive TCRs, polypeptides, or proteins can consist essentially of the amino acid sequence of SEQ ID NO: 1 (CDR1 of α chain), 2 (CDR2 of α chain), 3 (CDR3 of α chain), 4 (CDR1 of β chain), 5 (CDR2 of β chain), 6 (CDR3 of β chain), or any combination thereof, e.g., SEQ ID NOs: 1-3, 4-6, or 1-6.

The TCRs, polypeptides, and proteins of the invention (including functional portions and functional variants) can be of any length, i.e., can comprise any number of amino acids, provided that the TCRs, polypeptides, or proteins (or functional portions or functional variants thereof) retain their biological activity, e.g., the ability to specifically bind to a cancer antigen in a CD8- and/or CD4-independent manner, detect cancer in a host, or treat or prevent cancer in a host, etc. For example, the polypeptide can be 50 to 5000 amino acids long, such as 50, 70, 75, 100, 125, 150, 175, 200, 300, 400, 500, 600, 700, 800, 900, 1000 or more amino acids in length. In this regard, the polypeptides of the invention also include oligopeptides.

The TCRs, polypeptides, and proteins of the invention (including functional portions and functional variants) of the invention can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-β-amino-2-norbornane)-carboxylic acid, α,γ-diaminobutyric acid, α,β-diaminopropionic acid, homophenylalanine, and α-tert-butylglycine.

The TCRs, polypeptides, and proteins of the invention (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

When the TCRs, polypeptides, and proteins of the invention (including functional portions and functional variants) are in the form of a salt, preferably, the polypeptides are in the form of a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

The invention also provides TCRs, polypeptides, and/or proteins comprising an amino acid sequence that is at least about 70% or more, e.g., about 80%, about 90%, about 91%, about 92%, about 93%, about 94%, about 95%, about 96%, about 97%, about 98%, or about 99% identical to any of the amino acid sequences described herein.

The TCRs, polypeptides, and/or proteins of the invention (including functional portions and functional variants thereof) can be obtained by methods known in the art. Suitable methods of de novo synthesizing polypeptides and proteins are described in references, such as Chan et al., *Fmoc Solid Phase Peptide Synthesis*, Oxford University Press, Oxford, United Kingdom, 2005; *Peptide and Protein Drug Analysis*, ed. Reid, R., Marcel Dekker, Inc., 2000; *Epitope Mapping*, ed. Westwood et al., Oxford University Press, Oxford, United Kingdom, 2001; and U.S. Pat. No. 5,449,752. Also, polypeptides and proteins can be recombinantly produced using the nucleic acids described herein using standard recombinant methods. See, for instance, Sambrook et al., *Molecular Cloning: A Laboratory Manual*, $3^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, NY, 1994. Further, some of the TCRs, polypeptides, and proteins of the invention (including functional portions and functional variants thereof) can be isolated and/or purified from a source, such as a plant, a bacterium, an insect, a mammal, e.g., a rat, a mouse, a human, etc. Methods of isolation and purification are well-known in the art. Alternatively, the TCRs, polypeptides, and/or proteins described herein (including functional portions and functional variants thereof) can be commercially synthesized by companies, such as Synpep (Dublin, Calif.), Peptide Technologies Corp. (Gaithersburg, Md.), and Multiple Peptide Systems (San Diego, Calif.). In this respect, the inventive TCRs, polypeptides, and proteins can be synthetic, recombinant, isolated, and/or purified.

Included in the scope of the invention are conjugates, e.g., bioconjugates, comprising any of the inventive TCRs, polypeptides, or proteins (including any of the functional portions or variants thereof), nucleic acids, recombinant expression vectors, host cells, or populations of host cells. Conjugates, as well as methods of synthesizing conjugates in general, are known in the art (See, for instance, Hudecz, F., *Methods Mol. Biol.* 298: 209-223 (2005) and Kirin et al., *Inorg Chem.* 44(15): 5405-5415 (2005)).

Further provided by the invention is a nucleic acid comprising a nucleotide sequence encoding any of the TCRs, polypeptides, or proteins described herein (including functional portions and functional variants thereof).

By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl)uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The nucleic acid can comprise any nucleotide sequence which encodes any of the TCRs, polypeptides, or proteins, or functional portions or functional variants thereof described herein. For example, an embodiment of the unmodified nucleic acid can comprise SEQ ID NO: 33 (variable region of α chain); SEQ ID NO: 34 (variable region of β chain); SEQ ID NOs: 33 and 34; SEQ ID NOs: 27-29 (CDR1, CDR2, CDR3 regions of α chain, respectively) and SEQ ID NO: 35 (constant region of α chain); SEQ ID NOs: 30-32 (CDR1, CDR2, CDR3 regions of β chain, respectively) and SEQ ID NO: 36 (constant region of β chain); SEQ ID NOs: 27-32 and 35-36; SEQ ID NO: 37 (α chain); SEQ ID NO: 38 (β chain); SEQ ID NOs: 37 and 38; or SEQ ID NO: 39 (unmodified TCR).

The invention also provides modified nucleic acid sequences which encode any of the modified TCRs, modified polypeptides, or modified proteins described herein. In general, the modified nucleic acids include modified nucleotide sequences that encode modified constant regions. Any of the modified nucleic acids may include the nucleotide sequence for any one or more of the CDR1, CDR2, CDR3 regions or variable regions described for the unmodified nucleotide sequences.

In one embodiment of the modified nucleic acid, the nucleotide sequence includes one or more nucleotide substitutions in the constant region of one or both of the α and chains that replaces a codon that encodes Ser or Thr with a codon that encodes Cys to provide a nucleotide sequence encoding a cysteine-substituted tyrosinase TCR. In general, the modified nucleotide sequences of the constant regions of TCR α and β chains, SEQ ID NOs: 40 and 41, respectively, correspond with all or portions of the native, unmodified nucleic acid sequences SEQ ID NOs: 35 and 36, respectively, with SEQ ID NOs: 40 and 41 having at least one substitution when compared to SEQ ID NOs: 35 and 36, respectively. One or both of the native NNN at positions 142-144 of SEQ ID NO: 35 and NNN at positions 169-171 of SEQ ID NO: 36 may be substituted with a codon that encodes Cys. Preferably, both of the native NNN at positions 142-144 of SEQ ID NO: 35 and NNN at positions 169-171 of SEQ ID NO: 36 are substituted with a codon that encodes Cys. In this regard, an embodiment of the nucleic acid comprises SEQ ID NOs: 27-29 and a nucleotide sequence comprising a) SEQ ID NO: 40, wherein NNN at positions 142-144 is selected from a codon that encodes Cys; b) SEQ ID NOs: 30-32 and a nucleotide sequence comprising SEQ ID NO: 41, wherein NNN at positions 169-171 is selected from a codon that encodes Cys; or c) SEQ ID NOs: 27-32 and a nucleotide sequence comprising SEQ ID NO: 40, wherein NNN at positions 142-144 is selected from a codon that encodes Cys and SEQ ID NO: 41, wherein NNN at positions 169-171 is selected from a codon that encodes Cys.

The modified nucleotide sequences of the cysteine-substituted tyrosinase TCR α and β chains, SEQ ID NOs: 42 and 43, respectively, correspond with all or portions of the native, unmodified nucleotide sequences SEQ ID NOs: 37 and 38, respectively, with SEQ ID NOs: 42 and 43 having at least one substitution when compared to SEQ ID NO: 37 and 38, respectively. One or both of the native NNN at positions 532-534 of SEQ ID NO: 37 and NNN at positions 583-585 of SEQ ID NO: 38 may be substituted with a codon that encodes Cys. Preferably, both of the native NNN at positions 532-534 of SEQ ID NO: 37 and NNN at positions 583-585 of SEQ ID NO: 38 are substituted with a codon that encodes Cys. In this regard, an embodiment of the nucleic acid comprises a) SEQ ID NO: 42, wherein NNN at positions 532-534 is selected from a codon that encodes Cys; b) SEQ ID NO: 43, wherein NNN at positions 583-585 is selected from a codon that encodes Cys; or c) SEQ ID NO: 42, wherein NNN at positions 532-534 is selected from a codon that encodes Cys and SEQ ID NO: 43, wherein NNN at positions 583-585 is selected from a codon that encodes Cys.

In another embodiment of the modified nucleic acid, the modified nucleotide sequence includes a murine constant region in place of the unmodified, native human constant region of one or both of the α and the β chains to provide a nucleotide sequence that encodes a murine-human chimera tyrosinase TCR. In general, the modified nucleotide sequences of the constant regions of TCR α and β chains, SEQ ID NOs: 45 and 46, respectively, correspond with all or portions of the native, unmodified human nucleotide sequences SEQ ID NOs: 35 and 36, respectively, with SEQ ID NOs: 45 and 46 including a sequence that corresponds to the murine constant region in place of the human constant region sequences of SEQ ID NOs: 35 and 36, respectively.

In this regard, an embodiment of the modified nucleic acid comprises SEQ ID NOs: 27-29 and 45; SEQ ID NOs: 30-32 and 46; SEQ ID NOs: 27-32 and 45-46; SEQ ID NOs: 27-32, 36 and 45; or SEQ ID NOs: 27-32, 35 and 46.

The modified nucleotide sequences of the murine-human chimera tyrosinase TCR α and β chains, SEQ ID NOs: 47 and 48, respectively, correspond with all or portions of the native, unmodified human nucleotide sequences SEQ ID NOs: 37 and 38, respectively, with SEQ ID NOs: 47 and 48 including a sequence that corresponds to the murine constant region in place of the human constant region sequences of SEQ ID NOs: 37 and 38, respectively. In this regard, an embodiment of the nucleic acid comprises SEQ ID NO: 47, SEQ ID NO: 48, both SEQ ID NOs: 47 and 48, both SEQ ID NOs: 37 and 48, or both SEQ ID NOs: 38 and 47.

In still another embodiment of the modified nucleic acid, the modified nucleotide sequence includes a murine constant region in place of the unmodified, native human constant region of one or both of the α and the β chains in addition to one or more nucleotide substitutions in which a codon encoding Ser or Thr is replaced with a codon encoding Cys in the constant region of one or both of the α and β chains to provide a nucleotide sequence encoding a cysteine-substituted murine-human chimera tyrosinase TCR. In general, the modified nucleotide sequences of the constant regions of TCR α and β chains, SEQ ID NOs: 50 and 51, respectively, correspond with all or portions of the native, unmodified human amino acid sequences SEQ ID NOs: 35 and 36, respectively, with SEQ ID NOs: 50 and 51 having a sequence that corresponds to the murine constant region in place of the human constant region sequences of SEQ ID NOs: 35 and 36, respectively, and having at least one substitution when compared to the unmodified murine constant regions of SEQ ID NO: 45 and 46, respectively. One or both of the native murine NNN at positions 142-144 of SEQ ID NO: 45 and the native murine NNN at positions 169-171 of SEQ ID NO: 46 may be substituted with a codon that encodes Cys. Preferably, both of the native murine NNN at positions 142-144 of SEQ ID NO: 45 and the native muring NNN at positions 169-171 of SEQ ID NO: 46 are substituted with a codon that encodes Cys. In this regard, an embodiment of the nucleic acid comprises SEQ NOs: 27-29 and a nucleotide sequence comprising SEQ ID NO: 50, wherein NNN at positions 142-144 is selected from a codon that encodes Cys; SEQ NOs: 30-32 and a nucleotide sequence comprising SEQ ID NO: 51, wherein NNN at positions 169-171 is selected from a codon that encodes Cys; or SEQ NOs: 27-32 and a nucleotide sequence comprising SEQ ID NO: 50, wherein NNN at positions 142-144 is selected from a codon that encodes Cys, and SEQ ID NO: 51, wherein NNN at positions 169-171 is selected from a codon that encodes Cys.

The modified nucleotide sequences of the cysteine substituted murine-human chimera tyrosinase TCR α and β chains, SEQ ID NOs: 52 and 53, correspond with all or portions of the native, unmodified human amino acid sequences SEQ ID NOs: 37 and 38, respectively, with SEQ ID NOs: 52 and 53 having a sequence that corresponds to the murine constant region in place of the human constant region sequences of SEQ ID NOs: 37 and 38 and having at least one substitution when compared to the unmodified murine constant regions of SEQ ID NOs: 47 and 48, respectively. One or both of the native murine NNN at positions 532-534 of SEQ ID NO: 47 and the native murine NNN at positions 583-585 of SEQ ID NO: 48 may be substituted with a codon that encodes Cys. Preferably, both of the native murine NNN at positions 532-534 of SEQ ID NO: 47 and the native muring NNN at positions 583-585 of SEQ ID NO: 48 are substituted with a codon that encodes Cys. In this regard, an embodiment of the modified nucleic acid comprises SEQ ID NO: 52, wherein NNN at positions 532-534 is selected from a codon that encodes Cys; SEQ ID NO: 53, wherein NNN at positions 583-585 is selected from a codon that encodes Cys; or SEQ ID NO: 52, wherein NNN at positions 532-534 is selected from a codon that encodes Cys and SEQ ID NO: 53, wherein NNN at positions 583-585 is selected from a codon that encodes Cys.

The codon of the modified nucleic acids of the invention that encodes Cys may be any suitable codon that encodes Cys. For example, the codon may be TGC or TGT. Preferably, the codon that encodes Cys is TGC.

An embodiment of the invention also provides a nucleic acid comprising any one or more of SEQ ID NO: 56 (variable region of α chain); SEQ ID NO: 57 (constant region of α chain); SEQ ID NO: 58 (ribosomal "skip" sequence); SEQ ID NO: 59 (variable region of I chain); and SEQ ID NO: 60 (constant region of β chain). Nucleic acid SEQ ID NO: 56 encodes amino acid sequence SEQ ID NO: 55 (variable region of α chain). In this regard, the nucleic acid comprises SEQ ID NO: 56; SEQ ID NOs: 56 and 57; SEQ ID NOs: 56 and 59; SEQ ID NOs: 56-57 and 59-60; or SEQ ID NOs: 56-60.

Any of the nucleic acids of the invention may further comprise a ribosomal "skip" nucleotide sequence. In this regard, any of the embodiments of the inventive nucleic acids may also include SEQ ID NO: 26 or a sequence that is degenerate to SEQ ID NO: 26. The ribosomal "skip" sequence may be downstream of the nucleotide sequence for the α chain and upstream of the nucleotide sequence for the β chain. Alternatively, the ribosomal "skip" sequence may be downstream of the nucleotide sequence for the β chain and upstream of the nucleotide sequence for the α chain. Without being bound to a particular theory, although SEQ ID NO: 26 is transcribed and would hypothetically encode amino acid sequence SEQ ID NO: 13, it is believed that SEQ ID NO: 13 is not actually translated by the host cell. It is, instead, believed that the ribosomal "skip" sequence improves translation efficiency by providing a single transcript that may be translated by a single ribosome to provide two separate α and β polypeptide chains. Thus, it is believed that a single nucleotide sequence comprising, for example, from the 5' to the 3' end: a nucleotide sequence encoding an α chain, the ribosomal "skip" sequence SEQ ID NO: 26, and a nucleotide sequence encoding a β chain, is transcribed into a single, mRNA transcript including the α chain, the ribosomal "skip" sequence, and the β chain. It is believed that this single mRNA transcript is translated to produce two, separate polypeptide chains, i.e., an α chain and a β chain.

Further embodiments of the modified nucleic acid comprise SEQ ID NO: 39 (unmodified TCR with ribosomal "skip" sequence); SEQ ID NO: 44, wherein NNN at positions 532-534 and 1477-1479 is selected from a codon that encodes Cys (cysteine-substituted tyrosinase TCR and ribosomal "skip" sequence); SEQ ID NO: 49 (murine-human chimera tyrosinase TCR and ribosomal "skip" sequence); or SEQ ID NO: 54, wherein NNN at positions 532-534 and 1465-1467 is selected from a codon that encodes Cys (cysteine-substituted murine-human TCR with ribosomal "skip" sequence).

The nucleic acid alternatively can comprise a nucleotide sequence which is degenerate to any one or more of SEQ ID NOs: 26-54 and 56-60.

The invention also provides a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein.

The invention also provides a nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions preferably hybridizes under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive TCRs. It is generally appreciated that conditions can be rendered more stringent by the addition of increasing amounts of formamide.

The nucleic acids of the invention can be incorporated into a recombinant expression vector. In this regard, an embodiment of the invention provides recombinant expression vectors comprising any of the nucleic acids of the invention. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages does not hinder the transcription or replication of the vector.

The recombinant expression vector of the invention can be any suitable recombinant expression vector, and can be used to transform or transduce any suitable host. Suitable vectors include those designed for propagation and expansion or for expression or both, such as plasmids and viruses. The vector can be selected from the group consisting of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-Cl, pMAM and pMAMneo (Clontech). Preferably, the recombinant expression vector is a viral vector, e.g., a retroviral vector.

The recombinant expression vectors of the invention can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColEl, 2μ plasmid, λ, SV40, bovine papilloma virus, and the like.

Desirably, the recombinant expression vector comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based.

The recombinant expression vector can include one or more marker genes, which allow for selection of transformed or transduced hosts. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or normative promoter operably linked to the nucleotide sequence encoding the TCR, polypeptide, or protein (including functional portions and functional variants thereof), or to the nucleotide sequence which is complementary to or which hybridizes to the nucleotide sequence encoding the TCR, polypeptide, or protein. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, and a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression. Further, the recombinant expression vectors can be made to include a suicide gene.

As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, *Suicide Gene Therapy: Methods and Reviews*, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine deaminase, purine nucleoside phosphorylase, and nitroreductase.

Another embodiment of the invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α E. coli cells, Chinese hamster ovarian cells, monkey VERO cells, COS cells, HEK293 cells, and the like. For purposes of amplifying or replicating the recombinant expression vector, the host cell is preferably a prokaryotic cell, e.g., a DH5α cell. For purposes of producing a recombinant TCR, polypeptide, or protein, the host cell is preferably a mammalian cell. Most preferably, the host cell is a human cell. While the host cell can be of any cell type, can originate from any type of tissue, and can be of any developmental stage, the host cell preferably is a peripheral blood leukocyte (PBL) or a peripheral blood mononuclear cell (PBMC). More preferably, the host cell is a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. Preferably, the T cell is a human T cell. More preferably, the T cell is a T cell isolated from a human. The T cell can be any type of T cell and can be of any developmental stage, including but not limited to, CD4$^+$/CD8$^+$ double positive T cells, CD4$^+$ helper T cells, e.g., Th$_1$ and Th$_2$ cells, CD8$^+$ T cells (e.g., cytotoxic T cells), tumor infiltrating lymphocytes (TILs), memory T cells, naïve T cells, and the like. Preferably, the T cell is a CD8$^+$ T cell or a CD4$^+$ T cell.

Also provided by an embodiment of the invention is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cells, a muscle cell, a brain cell, etc. Alternatively, the population of cells can be a substantially homogeneous population, in which the population comprises mainly of host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

In some embodiments, the TCR or antigen binding portion thereof can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

The inventive TCRs, polypeptides, proteins, (including functional portions and functional variants thereof), nucleic acids, recombinant expression vectors, and host cells (including populations thereof) can be isolated and/or purified. The term "isolated" as used herein means having been removed from its natural environment. The term "purified" as used herein means having been increased in purity, wherein "purity" is a relative term, and not to be necessarily construed as absolute purity. For example, the purity can be at least about 50%, can be greater than 60%, 70% or 80%, or can be 100%.

The inventive TCRs, polypeptides, proteins (including functional portions and variants thereof), nucleic acids, recombinant expression vectors, and host cells (including populations thereof), all of which are collectively referred to as "inventive TCR materials" hereinafter, can be formulated into a composition, such as a pharmaceutical composition. In this regard, an embodiment of the invention provides a pharmaceutical composition comprising any of the TCRs, polypeptides, proteins, functional portions, functional variants, nucleic acids, expression vectors, and host cells (including populations thereof), and a pharmaceutically acceptable carrier. The inventive pharmaceutical compositions containing any of the inventive TCR materials can comprise more than one inventive TCR material, e.g., a polypeptide and a nucleic acid, or two or more different TCRs. Alternatively, the pharmaceutical composition can comprise an inventive TCR material in combination with another pharmaceutically active agents or drugs, such as a chemotherapeutic agent(s), e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

Preferably, the carrier is a pharmaceutically acceptable carrier. With respect to pharmaceutical compositions, the carrier can be any of those conventionally used and is limited only by chemico-physical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular inventive TCR material, as well as by the particular method used to administer the inventive TCR material. Accordingly, there are a variety of suitable formulations of the pharmaceutical composition of the invention. The following formulations for parenteral, intratumoral, subcutaneous, intravenous, intramuscular, intraarterial, intrathecal, and interperitoneal administration are exemplary and are in no way limiting. More than one route can be used to administer the inventive TCR materials, and in certain instances, a particular route can provide a more immediate and more effective response than another route.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The inventive TCR material can be administered in a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-1, 3-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5% to about 25% by weight of the inventive TCR material in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Injectable formulations are in accordance with the invention. The requirements for effective pharmaceutical carriers for injectable compositions are well-known to those of ordinary skill in the art (see, e.g., *Pharmaceutics and Pharmacy Practice*, J. B. Lippincott Company, Philadelphia, Pa., Banker and Chalmers, eds., pages 238-250 (1982), and *ASHP Handbook on Injectable Drugs*, Toissel, 4th ed., pages 622-630 (1986)). Preferably, when administering cells, e.g., T cells, the cells are administered via injection.

It will be appreciated by one of skill in the art that, in addition to the above-described pharmaceutical compositions, the inventive TCR materials of the invention can be formulated as inclusion complexes, such as cyclodextrin inclusion complexes, or liposomes.

For purposes of the invention, the amount or dose of the inventive TCR material administered should be sufficient to effect, e.g., a therapeutic or prophylactic response, in the subject or animal over a reasonable time frame. For example, the dose of the inventive TCR material should be sufficient to bind to a cancer antigen, or detect, treat or prevent cancer in a period of from about 2 hours or longer, e.g., 12 to 24 or more hours, from the time of administration. In certain embodiments, the time period could be even longer. The dose will be determined by the efficacy of the particular inventive TCR material and the condition of the animal (e.g., human), as well as the body weight of the animal (e.g., human) to be treated.

Many assays for determining an administered dose are known in the art. For purposes of the invention, an assay, which comprises comparing the extent to which target cells are lysed or IFN-γ is secreted by T cells expressing the inventive TCR, polypeptide, or protein upon administration of a given dose of such T cells to a mammal among a set of mammals of which is each given a different dose of the T cells, could be used to determine a starting dose to be administered to a mammal. The extent to which target cells are lysed or IFN-γ is secreted upon administration of a certain dose can be assayed by methods known in the art, including, for instance, the methods described herein as Example 6.

The dose of the inventive TCR material also will be determined by the existence, nature and extent of any adverse side effects that might accompany the administration of a particular inventive TCR material. Typically, the attending physician will decide the dosage of the inventive TCR material with which to treat each individual patient, taking into consideration a variety of factors, such as age, body weight, general health, diet, sex, inventive TCR material to be administered, route of administration, and the severity of the condition being treated. By way of example and not intending to limit the invention, the dose of the inventive TCR material can be about 0.001 to about 1000 mg/kg body weight of the subject being treated/day, from about 0.01 to about 10 mg/kg body weight/day, about 0.01 mg to about 1 mg/kg body weight/day.

One of ordinary skill in the art will readily appreciate that the inventive TCR materials of the invention can be modified in any number of ways, such that the therapeutic or prophylactic efficacy of the inventive TCR materials is increased through the modification. For instance, the inventive TCR materials can be conjugated either directly or indirectly through a linker to a targeting moiety. The practice of conjugating compounds, e.g., inventive TCR materials, to targeting moieties is known in the art. See, for instance, Wadwa et al., *J. Drug Targeting* 3: 111 (1995) and U.S. Pat. No. 5,087,616. The term "targeting moiety" as used herein, refers to any molecule or agent that specifically recognizes and binds to a cell-surface receptor, such that the targeting moiety directs the delivery of the inventive TCR materials to a population of cells on which surface the receptor is expressed. Targeting moieties include, but are not limited to, antibodies, or fragments thereof, peptides, hormones, growth factors, cytokines, and any other natural or non-natural ligands, which bind to cell surface receptors (e.g., Epithelial Growth Factor Receptor (EGFR), T-cell receptor (TCR), B-cell receptor (BCR), CD28, Platelet-derived Growth Factor Receptor (PDGF), nicotinic acetylcholine receptor (nAChR), etc.). The term "linker" as used herein, refers to any agent or molecule that bridges the inventive TCR materials to the targeting moiety. One of ordinary skill in the art recognizes that sites on the inventive TCR materials, which are not necessary for the function of the inventive TCR materials, are ideal sites for attaching a linker and/or a targeting moiety, provided that the linker and/or targeting moiety, once attached to the inventive TCR materials, do(es) not interfere with the function of the inventive TCR materials, i.e., the ability to bind to a cancer antigen, or to detect, treat, or prevent cancer.

Alternatively, the inventive TCR materials can be modified into a depot form, such that the manner in which the inventive TCR materials is released into the body to which it is administered is controlled with respect to time and location within the body (see, for example, U.S. Pat. No. 4,450,150). Depot forms of inventive TCR materials can be, for example, an implantable composition comprising the inventive TCR materials and a porous or non-porous material, such as a polymer, wherein the inventive TCR materials is encapsulated by or diffused throughout the material and/or degradation of the non-porous material. The depot is then implanted into the desired location within the body and the inventive TCR materials are released from the implant at a predetermined rate.

It is contemplated that the inventive pharmaceutical compositions, TCRs, polypeptides, proteins, nucleic acids, recombinant expression vectors, host cells, or populations of cells can be used in the prophylaxis of cancer or in methods of treating or preventing cancer. Without being bound to a particular theory, the inventive TCRs are believed to bind specifically to a cancer antigen, e.g., a glioma or melanoma antigen, such that the TCR (or related inventive polypeptide or protein) when expressed by a cell is able to mediate an immune response against the cell expressing the cancer antigen. In this regard, an embodiment of the invention provides a method of promoting the prophylaxis of cancer or of treating or preventing cancer in a host, comprising administering to the host any of the TCRs, polypeptides, or proteins described herein, any nucleic acid or recombinant expression vector comprising a nucleotide sequence encoding any of the TCRs, polypeptides, proteins described herein, or any host cell or population of cells comprising a recombinant vector which encodes any of the TCRs, polypeptides, or proteins described herein, in an amount effective to treat or prevent cancer in the host.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

Also provided is a method of detecting the presence of cancer in a host. The method comprises (i) contacting a sample comprising cells of the cancer any of the inventive TCRs, polypeptides, proteins, nucleic acids, recombinant expression vectors, or host cells, populations of cells, described herein, thereby forming a complex, and detecting the complex, wherein detection of the complex is indicative of the presence of cancer in the host.

With respect to the inventive method of detecting cancer in a host, the sample of cells of the cancer can be a sample comprising whole cells, lysates thereof, or a fraction of the whole cell lysates, e.g., a nuclear or cytoplasmic fraction, a whole protein fraction, or a nucleic acid fraction.

For purposes of the inventive detecting method, the contacting step can take place in vitro or in vivo with respect to the host. Preferably, the contacting is in vitro.

Also, detection of the complex can occur through any number of ways known in the art. For instance, the inventive TCRs, polypeptides, proteins, nucleic acids, recombinant expression vectors, host cells, or populations of cells described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

For purposes of the inventive methods, wherein host cells or populations of cells are administered, the cells can be cells that are allogeneic or autologous to the host. Preferably, the cells are autologous to the host.

With respect to the inventive methods, the cancer can be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, gastrointestinal carcinoid tumor, glioma (e.g., glioblastoma), Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), skin cancer, small intestine cancer, soft tissue cancer, stomach cancer, testicular cancer, thyroid cancer, ureter cancer, and urinary bladder cancer. Preferably, the cancer is skin cancer or brain cancer. More preferably, the cancer melanoma or glioma.

The host referred to in the inventive methods can be any host. Preferably, the host is a mammal. As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

EXAMPLES

The following examples further illustrate the invention but, of course, should not be construed as in any way limiting its scope.

Example 1

Tumor infiltrating lymphocytes (TIL) 1383 were grown from the inguinal lymph node of a patient with metastatic melanoma who had a partial response to adoptive cell transfer. Limited dilution cloning identified a CD4 positive clone reactive against the tyrosinse epitope 368-376 in an HLA-A2 restricted manner.

This example demonstrated a method of making a T-cell clone that is specific for tyrosinase (Tyr) epitope 368-376.

Example 2

This example demonstrated a method of making a nucleotide sequence encoding an unmodified tyrosinase TCR.

The TCR alpha and beta chain genes of the clones of Example 1 were identified using 5' rapid amplification of cDNA ends (5'RACE) using a Clonetech SMART™ RACE cDNA Amplification Kit (Mountain View, Calif.) according to the manufacturer's instructions and cloned into RNA expression vectors. Donor PBLs electroporated with this RNA was reactive against tyrosinase expressing tumor lines.

An MSGV1-based retroviral vector including the alpha and beta chain genes linked by a FrnSgsgP2A ribosomal "skip" sequence (SEQ ID NO: 26) was constructed using overlap PCR to provide a vector encoding an unmodified tyrosinase TCR (SEQ ID NO: 39). A first PCR reaction was performed using the RNA expression vector as a template and the following primers to produce a first nucleotide sequence including the unmodified tyrosinase TCR α chain: TCR α forward (SEQ ID NO: 61) and reverse (SEQ ID NO: 64). A second PCR reaction was performed using the RNA expression vector as a template and the following primers to produce a second nucleotide sequence including the unmodified tyrosinase TCR β chain: TCR β forward (SEQ ID NO: 65) and reverse (SEQ ID NO: 68). The products of the first and second PCR reactions were combined and used as a template for a third PCR reaction using the following combination of primers: TCR forward (SEQ ID NO: 61) and reverse (SEQ ID NO: 68) to produce a third nucleotide sequence including both the α and the β chains of the unmodified tyrosinase TCR (SEQ ID NO: 39). This nucleotide sequence was ligated into the MSGV1-based retroviral vector at the restriction endonuclease site NcoI or NotI.

This example demonstrated a method of making a recombinant expression vector encoding an unmodified tyrosinase TCR.

Example 3

This example demonstrates a method of making a nucleotide sequence encoding a cysteine-substituted tyrosinase TCR.

A nucleotide sequence encoding a cysteine-substituted tyrosinase TCR and including a FrnSgsgP2A ribosomal "skip" sequence (SEQ ID NO: 26) was constructed using overlap PCR. A first PCR reaction was performed using the RNA expression vector as a template and the following primers to produce a first nucleotide sequence including the variable region of the cysteine-substituted tyrosinase TCR α chain: TCR α forward (SEQ ID NO: 61) and reverse (SEQ ID NO: 62). A second PCR reaction was performed using the RNA expression vector as a template and the following primers to produce a second nucleotide sequence including the constant region of the cysteine-substituted tyrosinase TCR α chain: TCR α forward (SEQ ID NO: 63) and reverse (SEQ ID NO: 64). The products of the first and second PCR reactions were combined and used as a template for a third PCR reaction using the following combination of primers: TCR forward (SEQ ID NO: 61) and reverse (SEQ ID NO: 64) to produce a third nucleotide sequence including both the variable and the constant regions of the cysteine-substituted tyrosinase TCR α chain.

A fourth PCR reaction was performed using the RNA expression vector as a template and the following primers to produce a fourth nucleotide sequence including the variable region of the cysteine-substituted tyrosinase TCR β chain: TCR β forward (SEQ ID NO: 65) and reverse (SEQ ID NO: 66). A fifth PCR reaction was performed using the RNA expression vector as a template and the following primers to produce a fifth nucleotide sequence including the constant region of the cysteine-substituted tyrosinase TCR β chain: TCR β forward (SEQ ID NO: 67) and reverse (SEQ ID NO: 68). The products of the fourth and fifth PCR reactions were combined and used as a template for a sixth PCR reaction using the following combination of primers: TCR forward (SEQ ID NO: 65) and reverse (SEQ ID NO: 68) to produce a sixth nucleotide sequence including both the variable and the constant regions of the cysteine-substituted tyrosinase TCR β chain.

The products of the third and sixth PCR reactions were combined and used as a template for a seventh PCR reaction using the following combination of primers: TCR forward (SEQ ID NO: 61) and reverse (SEQ ID NO: 68) to produce a seventh nucleotide sequence including both the cysteine-substituted tyrosinase TCR α and β chains and the ribosomal "skip" sequence (SEQ ID NO: 44). This seventh nucleotide sequence was ligated into the MSGV1-based retroviral vector at the restriction endonuclease site NcoI or NotI.

This example demonstrated a method of making a recombinant expression vector encoding a cysteine-substituted tyrosinase TCR.

Example 4

This example demonstrates a method of making a nucleotide sequence encoding a murine-human chimera tyrosinase TCR.

A nucleotide sequence encoding a murine-human chimera tyrosinase TCR and including a FrnSgsgP2A ribosomal "skip" sequence (SEQ ID NO: 26) was constructed using overlap PCR as described in Example 3 using the primers set forth in Table 1.

TABLE 1

| PCR Reaction | Forward Primer | Reverse Primer |
| --- | --- | --- |
| First PCR Reaction | SEQ ID NO: 61 | SEQ ID NO: 69 |
| Second PCR Reaction | SEQ ID NO: 70 | SEQ ID NO: 71 |
| Third PCR Reaction | SEQ ID NO: 61 | SEQ ID NO: 71 |
| Fourth PCR Reaction | SEQ ID NO: 65 | SEQ ID NO: 72 |
| Fifth PCR Reaction | SEQ ID NO: 73 | SEQ ID NO: 74 |
| Sixth PCR Reaction | SEQ ID NO: 65 | SEQ ID NO: 74 |
| Seventh PCR Reaction | SEQ ID NO: 61 | SEQ ID NO: 74 |

Overlap PCR produced a nucleotide sequence including both the murine-human chimera tyrosinase TCR α and β chains and the ribosomal "skip" sequence (SEQ ID NO: 49). This nucleotide sequence was ligated into the MSGV1-based retroviral vector as described in Example 3.

This example demonstrated a method of making a recombinant expression vector encoding a murine-human chimera tyrosinase TCR.

Example 5

This example demonstrates a method of making a nucleotide sequence encoding a cysteine-substituted murine-human chimera tyrosinase TCR.

A nucleotide sequence encoding a cysteine-substituted murine-human chimera tyrosinase TCR and including a FrnSgsgP2A ribosomal "skip" sequence (SEQ ID NO: 26) was constructed using overlap PCR as described in Example 3 using the primers set forth in Table 2.

TABLE 2

| PCR Reaction | Forward Primer | Reverse Primer |
| --- | --- | --- |
| First PCR Reaction | SEQ ID NO: 61 | SEQ ID NO: 62 |
| Second PCR Reaction | SEQ ID NO: 63 | SEQ ID NO: 71 |
| Third PCR Reaction | SEQ ID NO: 61 | SEQ ID NO: 71 |
| Fourth PCR Reaction | SEQ ID NO: 65 | SEQ ID NO: 66 |
| Fifth PCR Reaction | SEQ ID NO: 67 | SEQ ID NO: 74 |
| Sixth PCR Reaction | SEQ ID NO: 65 | SEQ ID NO: 74 |
| Seventh PCR Reaction | SEQ ID NO: 61 | SEQ ID NO: 74 |

Overlap PCR produced a nucleotide sequence including both the cysteine-substituted murine-human chimera tyrosinase TCR α and β chains and the ribosomal "skip" sequence (SEQ ID NO: 54). This nucleotide sequence was ligated into the MSGV1-based retroviral vector as described in Example 3.

This example demonstrated a method of making a recombinant expression vector encoding a cysteine-substituted murine-human chimera tyrosinase TCR.

Example 6

This example demonstrates the biological activity of PBLs transduced with retroviral vectors encoding the TCRs of Examples 2, 3, 4, and 5.

PBLs from a normal human donor were transduced with a nucleic acid (SEQ ID NOs: 56-60) (encoding a tyrosinase TCR comprising SEQ ID NOs: 55, 9 and 12), the cysteine-substituted tyrosinase TCR vectors (NotI and NcoI) of Example 3 (encoding SEQ ID NOs: 16 and 17), the murine-human chimera tyrosinase TCR vectors (NotI and NcoI) of Example 4 (encoding SEQ ID NOs: 20 and 21), or the cysteine-substituted murine-human chimera tyrosinase TCR vector of Example 5 (encoding SEQ ID NOs: 24 and 25). Normal PBLs from a human donor were stimulated with OKT3 on day 0. Retrovirus was produced by transducing a retroviral producer cell line with the vector and a Rd114 packaging envelope. On day 2, retroviral supernatant was spin loaded onto retronectin coated plates for 2 hours at 2000 g. Stimulated donor PBLs were spin loaded onto the coated plates for 10 minutes at 1500 rpm. Control PBLs were transduced with GFP. TCR was detected on the cell surface of PBLs by FACS analysis using CD8 antibody and tyrosinase tetramer staining.

Biological activity of the transduced cells was assessed by co-culturing with target cells and measuring IFN-γ secretion. On day 7, a co-culture was performed with 100,000 effector cells (cells transduced with GFP (control), nucleic acid (encoding a tyrosinase TCR comprising SEQ ID NOs: 55, 9, and 12) (NcoI), cysteine-substituted tyrosinase TCR (NcoI), murine-human chimera tyrosinase TCR (NcoI), cysteine substituted murine-human chimera tyrosinase TCR (NcoI), cysteine-substituted tyrosinase TCR (NotI), murine-human chimera tyrosinase TCR (NotI)) and 100,000 of various target cells (526Mel-tyr+, hla-A2+; 624Mel-tyr+, hla-A2+; 888Mel-Tyr+, hla-A2−) and control cells CosEso and Cos Tyr. After 20 hours, the supernatant was removed and the IFN-γ level (pg/ml) was determined using a colormetric ELISA (Pierce Inc.). The results are shown in Table 3.

TABLE 3

| | Cos Eso (pg/ml) | Cos Tyr (pg/ml) | 526Mel (pg/ml) | 624Mel (pg/ml) | 888Mel (pg/ml) |
| --- | --- | --- | --- | --- | --- |
| GFP (control) | 154 | 257 | 195 | 232 | 164 |
| Tyr TCR comprising SEQ ID NOs: 55, 9, and 12 (NcoI) | 148 | 7072 | 5837 | 5884 | 154 |
| Cysteine-substituted tyrosinase TCR (NcoI) | 151 | 10975 | 12397 | 10272 | 126 |
| Murine-human chimera tyrosinase TCR (NcoI) | 117 | 16361 | 20529 | 15899 | 118 |
| Cysteine-substituted murine-human chimera tyrosinase TCR (NcoI) | 163 | 16065 | 15872 | 13907 | 141 |
| Cysteine-substituted tyrosinase TCR (NotI) | 151 | 9323 | 9327 | 8251 | 199 |
| Murine-human chimera tyrosinase TCR (NotI) | 144 | 12034 | 13599 | 10692 | 169 |

As shown in Table 3, the PBLs transduced with the nucleic acid encoding a tyrosinase TCR comprising SEQ ID NOs: 55, 9, and 12 secreted higher levels of IFN-γ than cells that were transduced with control GFP for the co-cultures with 526Mel, 624Mel, and Cos Tyr cells. PBLs transduced with cysteine-substituted tyrosinase TCR, the murine-human chimera tyrosinase TCR, or the cysteine-substituted murine-human chimera tyrosinase TCR each secreted higher levels of IFN-γ than cells that were transduced with the nucleic acid encoding a tyrosinase TCR comprising SEQ ID NOs: 55, 9, and 12 for the co-cultures with 526Mel, 624Mel, and Cos Tyr cells. Furthermore, regardless of whether the nucleotide sequence (encoding the cysteine-substituted tyrosinase TCR or the murine-human chimera tyrosinase TCR) was ligated into the NcoI or NotI site of the MSGV1-based retroviral vector, the transduced PBLs secreted higher levels of IFN-γ than cells that were transduced with control GFP. Subsequent experiments were performed with the TCR nucleic acid ligated into the NcoI site.

This example demonstrated that PBLs transduced with the nucleic acid (encoding a tyrosinase TCR comprising SEQ ID NOs: 55, 9, and 12) secreted higher levels of IFN-γ than cells that were transduced with GFP. This example also demonstrated that PBLs transduced with the cysteine-substituted tyrosinase TCR, the murine-human chimera tyrosinase TCR, or the cysteine-substituted murine-human chimera tyrosinase TCR each secreted higher levels of IFN-γ than cells that were transduced with the nucleic acid encoding a tyrosinase TCR comprising SEQ ID NOs: 55, 9, and 12, and that regardless of whether the TCR nucleotide sequence was ligated into the NcoI or NotI site of the MSGV1-based retroviral vector, the transduced PBLs secreted higher levels of IFN-γ than cells that were transduced with control GFP.

Example 7

This example demonstrates the biological activity of PBLs transduced with retroviral vectors encoding the TCRs of Examples 3 and 4.

PBLs from a normal human donor were transduced with GFP (control), the cysteine-substituted tyrosinase TCR vector of Example 3 (encoding SEQ ID NOs: 16 and 17), the murine-human chimera tyrosinase TCR vector of Example 4 (encoding SEQ ID NOs: 20 and 21), MART-1 F4 TCR, or gp100 (154) TCR, and TCR was detected on the cell surface of PBLs by FACS analysis as described in Example 6.

Biological activity of the transduced cells was assessed by co-culturing with target cells (526Mel, 624Mel, 888Mel)

and control cells (T2-MART-1, T2-gp100, T2-Tyr) and measuring IFN-γ secretion and the IFN-γ level (pg/ml) as described in Example 6. The results are shown in Table 4.

TABLE 4

|  | T-2 MART-1 (pg/ml) | T2-gp100 (pg/ml) | T2-Tyr (pg/ml) | 526Mel (pg/ml) | 624Mel (pg/ml) | 888Mel (pg/ml) |
| --- | --- | --- | --- | --- | --- | --- |
| GFP (control) | 0 | 0 | 0 | 0 | 0 | 0 |
| MART-1 F4 TCR | 10382 | 33 | 19 | 1300 | 1175 | 12 |
| Gp100 (154) TCR | 49 | 721 | 59 | 4125 | 3162 | 5 |
| Murine-human chimera tyrosinase TCR | 87 | 106 | 3180 | 7765 | 6096 | 0 |
| Cysteine-substituted tyrosinase TCR | 66 | 80 | 4114 | 4790 | 4269 | 19 |

As shown in Table 4, the PBLs transduced with the cysteine-substituted tyrosinase TCR or the murine-human chimera tyrosinase TCR secreted higher levels of IFN-γ than cells that were transduced with GFP, gp100 TCR or MART-1 TCR for the co-cultures with 526Mel, 624Mel, and T2-Tyr cells.

This example demonstrated that cells transduced with a nucleic acid encoding a murine-human chimera tyrosinase TCR or a cysteine-substituted tyrosinase TCR secreted higher levels of IFN-γ than cells that were transduced with a nucleic acid encoding GFP, gp100 TCR or MART-1 TCRs.

Example 8

This example demonstrates the biological activity of PBLs transduced with a nucleic acid encoding a murine-human chimera tyrosinase TCR in both CD4 and CD8 populations of cells.

Normal PBLs from a human donor were transduced as described in Example 6 with GFP (control), MART-1 TCR, gp100 TCR, and murine-human chimera tyrosinase TCR (encoding SEQ ID NOs: 20 and 21). TCR was detected on the cell surface of PBLs by FACS analysis.

The PBLs transduced with MART-1 TCR, gp100 TCR, and murine-human chimera tyrsoinase TCR were sorted using CD4 and CD8 beads (Miltenyi, Inc.) to produce purified CD4 and CD8 populations. Purity of each population was measured and was determined to be 91% for the CD4 population and 92.5% for the CD8 population.

The activity of PBLs transduced with nucleic acids encoding GFP, MART-1 TCR, gp100 TCR, and murine-human chimera tyrosinase TCR was evaluated by assaying IFN-γ and TNF-α secretion upon stimulation with melanoma cells for both the CD4 and CD8 sorted populations. The transduced cells (100,000) are co-cultured with 100,000 target cells (526Mel, 624Mel, 888Mel). After 20 hours, the supernatant was removed and the IFN-γ (Table 5) and TNF-α (Table 6) levels were determined using colometric ELISA (Pierce, Inc.).

TABLE 5

|  | CD4 Sorted | | | CD8 Sorted | | |
| --- | --- | --- | --- | --- | --- | --- |
|  | 526Mel (pg/ml) | 624Mel (pg/ml) | 888Mel (pg/ml) | 526Mel (pg/ml) | 624Mel (pg/ml) | 888Mel (pg/ml) |
| GFP | 0 | 0 | 0 | 0 | 0 | 0 |
| MART-1 (F4) TCR | 702 | 712 | 0 | 2071 | 2413 | 0 |
| Gp100 (154) TCR | 4878 | 5473 | 0 | 2385 | 2949 | 0 |
| Human-murine chimera Tyr TCR | 10493 | 11174 | 0 | 8701 | 7367 | 0 |

TABLE 6

|  | CD4 Sorted | | | CD8 Sorted | | |
| --- | --- | --- | --- | --- | --- | --- |
|  | 526Mel (pg/ml) | 624Mel (pg/ml) | 888Mel (pg/ml) | 526Mel (pg/ml) | 624Mel (pg/ml) | 888Mel (pg/ml) |
| GFP | 0 | 0 | 0 | 0 | 0 | 0 |
| MART-1 (F4) TCR | 52 | 63 | 0 | 399 | 459 | 4 |
| Gp100 (154) TCR | 1294 | 1384 | 0 | 429 | 408 | 0 |
| Human-murine chimera Tyr TCR | 2230 | 2145 | 0 | 1074 | 1012 | 0 |

As shown in Tables 5 and 6, for both the CD4 and CD8 sorted populations of cells, the PBLs transduced with a murine-human chimera tyrosinase TCR secreted higher levels of IFN-γ and TNF-α than cells that were transduced with a nucleic acid encoding gp100 or MART-1 TCRs when co-cultured with 526Mel or 624Mel cells.

This example demonstrated that cells transduced with a nucleic acid encoding a murine-human chimera tyrosinase TCR specific for tyrosinase secreted higher levels of IFN-γ and TNF-α than cells that were transduced with a nucleic acid encoding gp100 or MART-1 TCRs for both CD4 and CD8 populations of cells.

Example 9

This example demonstrates the biological activity of PBLs transduced with a nucleic acid encoding a TCR specific for tyrosinase.

Normal PBLs were transduced with nucleic acids encoding GFP (control), MART-1 F4 TCR, gp100 (154) TCR, murine-human chimera tyrosinase TCR (comprising SEQ ID NOs: 20 and 21), and cysteine-substituted tyrosinase TCR (comprising SEQ ID NOs: 16 and 17), as described in Example 6. The transduced PBLs were sorted to produce purified CD4 and CD8 populations as described in Example 8.

CD4 and CD8 blocking studies were performed by incubating 526Mel cells with CD8 or CD4 (10 μg/ml) blocking antibody for 30 minutes. The 526Mel cells were then co-cultured with the GFP, MART-1 TCR, gp100 TCR, murine-human chimera tyrosinase TCR, and cysteine-substituted tyrosinase TCR, the supernatant was collected and IFN-γ secretion was determined as described in Example 6. Results are shown in Table 7A.

TABLE 7A

| | Mel 526 Unblock (IFN-γ pg/ml) | Mel526 CD4 block (IFN-γ pg/ml) | Mel526 CD8 block (IFN-γ pg/ml) | % decrease with CD4 block | % decrease with CD8 block |
|---|---|---|---|---|---|
| GFP | 0 | 0 | 0 | — | — |
| MART-1 F4 TCR | 1300 | 1138 | 103 | 12.5 | 92.1 |
| Gp100 154 TCR | 4125 | 3435 | 3781 | 16.7 | 8.3 |
| Cys-substituted Tyr TCR | 4790 | 4986 | 4664 | −4.1 | 2.6 |
| Murine-human Chimera Tyr TCR | 7764 | 6104 | 5580 | 21.4 | 28.1 |

As shown in Table 7A, PBLs transduced with murine-human chimera tyrosinase TCR showed a 21.4% decrease of IFN-γ secretion with a CD4 block and a 28.1% decrease with a CD8 block. The cysteine-substituted tyrosinase TCR showed a −4.1% decrease of IFN-γ secretion with a CD4 block and a 2.6% decrease with a CD8 block. MART-1, in comparison, showed a 12.5% decrease of IFN-γ secretion with a CD4 block and a 92.1% decrease with a CD8 block, and gp100 showed a 16.7% decrease with a CD4 block and a 8.3% decrease with a CD8 block.

In a separate experiment, antibody blockade was used to assess the contribution of the CD4 and CD8 co-receptors to the reactivity of PBL transduced with unmodified anti-tyrosinase TCR (SEQ ID NOs: 11 and 12). For blocking of co-stimulatory molecules CD4 and CD8, $5 \times 10^4$ TCR transduced PBL were incubated with 20 µg/ml of appropriate antibody (Becton Dickinson) for 1 hour at 37° C. then co-cultured for 20-hours with $1 \times 10^5$ targets. Values were recorded as percent activity compared to isotype (mouse IgG2) control antibody. Controls included PBL transduced with a CD8-independent anti-MART-1 TCR and a CD4-dependent TIL clone 1749-E11. The results are shown in Table 7B.

TABLE 7B

| Effector vs. Target | Isotype Antibody (% Activity vs. isotype) | Anti-CD4 (% Activity vs. isotype) | Anti-CD8 (% Activity vs. isotype) |
|---|---|---|---|
| Unmodified Tyr TCR vs. 624Mel | 100 | 112 | 100 |
| Mart-1 TCR vs. 624Mel | 100 | 118 | 3 |
| TIL1749-E11 vs. 624CIIA | 100 | 1 | 108 |

As shown in Table 7B, CD4 and CD8 blocking antibodies were able to suppress the reactivity of the TIL clone and anti-MART-1 TCR transduced PBL, respectively, but had no effect on anti-tyrosinase TCR transduced PBL.

This example demonstrated that the activity of PBLs transduced with unmodified tyrosinase TCR, murine-human chimera tyrosinase TCR, or cysteine-substituted tyrosinase TCR is CD8/CD4 independent.

Example 10

This example demonstrates the expression levels and biological activity of PBLs transduced with unmodified or modified tyrosinase TCR.

PBLs from three normal human donors were transduced with nucleic acids encoding GFP (control), GP100 TCR (154), MART-1 TCR (F4), unmodified tyrosinase TCR (comprising SEQ ID NOs: 11 and 12), cysteine-substituted tyrosinase TCR (comprising SEQ ID NOs: 16 and 17), murine-human chimera tyrosinase TCR (comprising SEQ ID NOs: 20 and 21), and murine-human chimera, cysteine-substituted tyrosinase TCR (SEQ ID NOs: 24 and 25). TCR was detected on the cell surface of the PBLs by FACS analysis using CD8 antibody, tyrosinase tetramer staining, and antibody against the beta chain variable region (Vβ). The results were averaged and are set forth in Table 8.

The transduced PBLs were co-cultured with target cells, the supernatant was collected, and IFN-γ secretion was determined as described in Example 6. The results were averaged and are set forth in Table 8.

TABLE 8

| | Tetramer Staining (%) | Vβ staining (%) | IFNg Release vs. 624Mel (pg/ml) |
|---|---|---|---|
| Unmodified Tyr TCR | 12.0 (±3.3) | 70.3 (±6.9) | 11,023 (±1185) |
| Cysteine-substituted Tyr TCR | 15.5 (±4.0) | 68.3 (±4.9) | 11,358 (±2411) |
| Murine/human chimera Tyr TCR | 50.3 (±1.8) | 87.1 (±4.2) | 13,833 (±1950) |
| Cysteine-substituted murine-human chimera Tyr TCR | 40.4 (±6.4) | 77.8 (±7.1) | 15,038 (±1726) |

As shown in Table 8, PBLs transduced with cysteine-substituted tyrosinase TCR, murine-human chimera tyrosinase TCR, or cysteine-substituted murine-human chimera tyrosinase TCR each demonstrated higher TCR expression and higher tumor cell reactivity than PBLs transfected with unmodified TCR.

In a separate experiment, specific lysis of 624 Mel cells by PBLs transduced with GFP, unmodified Tyr TCR (encoding SEQ ID NOs: 11 and 12) and murine/human chimera Tyr TCR (SEQ ID NOs: 20 and 21). Lysis was assessed by radioactivity of supernatant following co-culture of $^{51}$Cr labeled tumor targets with effectors for 4 hours as previously described (Topalian, S. L. et al. *J. Immunol.* 142:3714-3725 (1989)). The increased cytokine production was associated with improved lytic ability as PBL transduced with the murine/human chimera Tyr TCR lysed 60% more tyrosinase expressing tumor cells than the unmodified Tyr TCR (49% vs 31% at a 17:1 effector to target ratio). These findings were repeated in 2 additional donor lymphocytes.

This example demonstrates that PBLs transduced with a modified tyrosinase TCR exhibit higher levels of TCR expression and higher tumor reactivity than PBLs transduced with unmodified tyrosinase TCR.

Example 11

This example demonstrates the rapid expansion of PBLs transduced with modified or unmodified tyrosinase TCR and the biological activity of rapidly expanded cells.

PBLs from three normal human donors were untransduced or transduced with nucleic acids encoding GFP, unmodified tyrosinase TCR (comprising SEQ ID NOs: 11 and 12), cysteine-substituted tyrosinase TCR (comprising SEQ ID NOs: 16 and 17), murine-human chimera tyrosinase TCR (comprising SEQ ID NOs: 20 and 21), or cysteine-substituted murine-human chimera tyrosinase TCR (SEQ ID NOs: 24 and 25) and rapidly expanded. On day 8 after stimulation, PBLs (100,000) were cultured with OKT-3, high dose IL-2 (1000 cu/ml), and 20,000,000 irradiated feeder cells (4000 rads). After 12 days, the cells were harvested and counted for fold expansion. Persistence of TCR expression was determined using FACS analysis. Each of the unmodified tyrosinase TCR, cysteine-substituted tyrosinase TCR, murine-human chimera tyrosinase TCR, and murine-human chimera, cysteine-substituted tyrosinase TCR showed at least a 140-fold expansion.

The rapidly expanded cells were co-cultured with 526Mel, 624Mel, and 888Mel, the supernatant was collected and IFN-γ secretion was measured as described in Example 6. The co-cultures with 526Mel and 624Mel demonstrated the persistence of function of PBLs transduced with unmodified tyrosinase TCR, cysteine-substituted tyrosinase TCR, murine-human chimera tyrosinase TCR, or murine-human chimera cysteine-substituted tyrosinase TCR following rapid expansion.

This example demonstrated the rapid expansion of PBLs transduced with modified or unmodified tyrosinase TCR and the persistence of function of the rapidly expanded cells.

Example 12

This example demonstrates the biological activity of PBLs transduced with murine-human tyrosinase TCR or unmodified tyrosinase TCR for both CD4 and CD8 populations of cells.

PBLs from two normal human donors (Donors A and B) were transduced as described in Example 6 with MART-1 TCR, gp100 TCR, unmodified tyrosinase TCR (comprising SEQ ID NOs: 11 and 12), and murine-human chimera tyrosinase TCR (comprising SEQ ID NOs: 20 and 21). Transduced cells were sorted using CD4 and CD8 beads (Miltenyi, Inc.) and purity of the CD4 and CD8 populations was analyzed as described in Example 8.

Transduced PBLs were co-cultured with target cells (526Mel, 624Mel, and 888Mel), the supernatant was collected and IFN-γ secretion was measured as described in Example 6. The results are set forth in Tables 9 (Donor A) and 10 (Donor B).

TABLE 9

|  | CD4 Sorted | | | CD8 Sorted | | |
| --- | --- | --- | --- | --- | --- | --- |
|  | 526Mel (pg/ml) | 624Mel (pg/ml) | 888Mel (pg/ml) | 526Mel (pg/ml) | 624Mel (pg/ml) | 888Mel (pg/ml) |
| MART-1 (F4) | 2149 | 0 | 0 | 11770 | 3787 | 0 |
| Gp100 (154) | 2151 | 17023 | 0 | 4694 | 5638 | 0 |
| Unmodified Tyr TCR | 22703 | 28302 | 0 | 21024 | 27238 | 0 |
| Murine-human chimera Tyr TCR | 57574 | 84967 | 0 | 54400 | 96300 | 0 |

TABLE 10

|  | CD4 Sorted | | | CD8 Sorted | | |
| --- | --- | --- | --- | --- | --- | --- |
|  | 526Mel (pg/ml) | 624Mel (pg/ml) | 888Mel (pg/ml) | 526Mel (pg/ml) | 624Mel (pg/ml) | 888Mel (pg/ml) |
| MART-1 (F4) | 0 | 0 | 0 | 3780 | 2320 | 0 |
| Gp100 (154) | 20802 | 41821 | 0 | 1597 | 2860 | 0 |
| Unmodified Tyr TCR | 22528 | 43582 | 0 | 10926 | 17451 | 0 |
| Murine-human chimera Tyr TCR | 27460 | 72497 | 0 | 12872 | 30227 | 0 |

As can be seen in Tables 9 and 10, PBLs transduced with murine-human tyrosinase TCR secreted higher levels of IFN-γ than PBLs transduced with unmodified tyrosinase TCR for both CD4 and CD8 populations of cells co-cultured with 526Mel or 624Mel cells.

This example demonstrated that PBLs transduced with murine-human tyrosinase TCR secreted higher levels of IFN-γ than PBLs transduced with unmodified tyrosinase TCR for both CD4 and CD8 populations of cells.

Example 13

This example demonstrates the biological activity of PBLs transduced with unmodified tyrosinase TCR or murine-human chimera tyrosinase TCR.

PBLs from two normal human donors (Donor A and Donor B) were transduced as described in Example 6 with MART-1 TCR, gp100 TCR, unmodified tyrosinase TCR (comprising SEQ ID NOs: 11 and 12), and murine-human chimera tyrosinase TCR (comprising SEQ ID NOs: 20 and 21). Transduced cells were sorted using CD4 and CD8 beads (Miltenyi, Inc.) and purity of the CD4 and CD8 populations was analyzed as described in Example 8.

Figure 2:
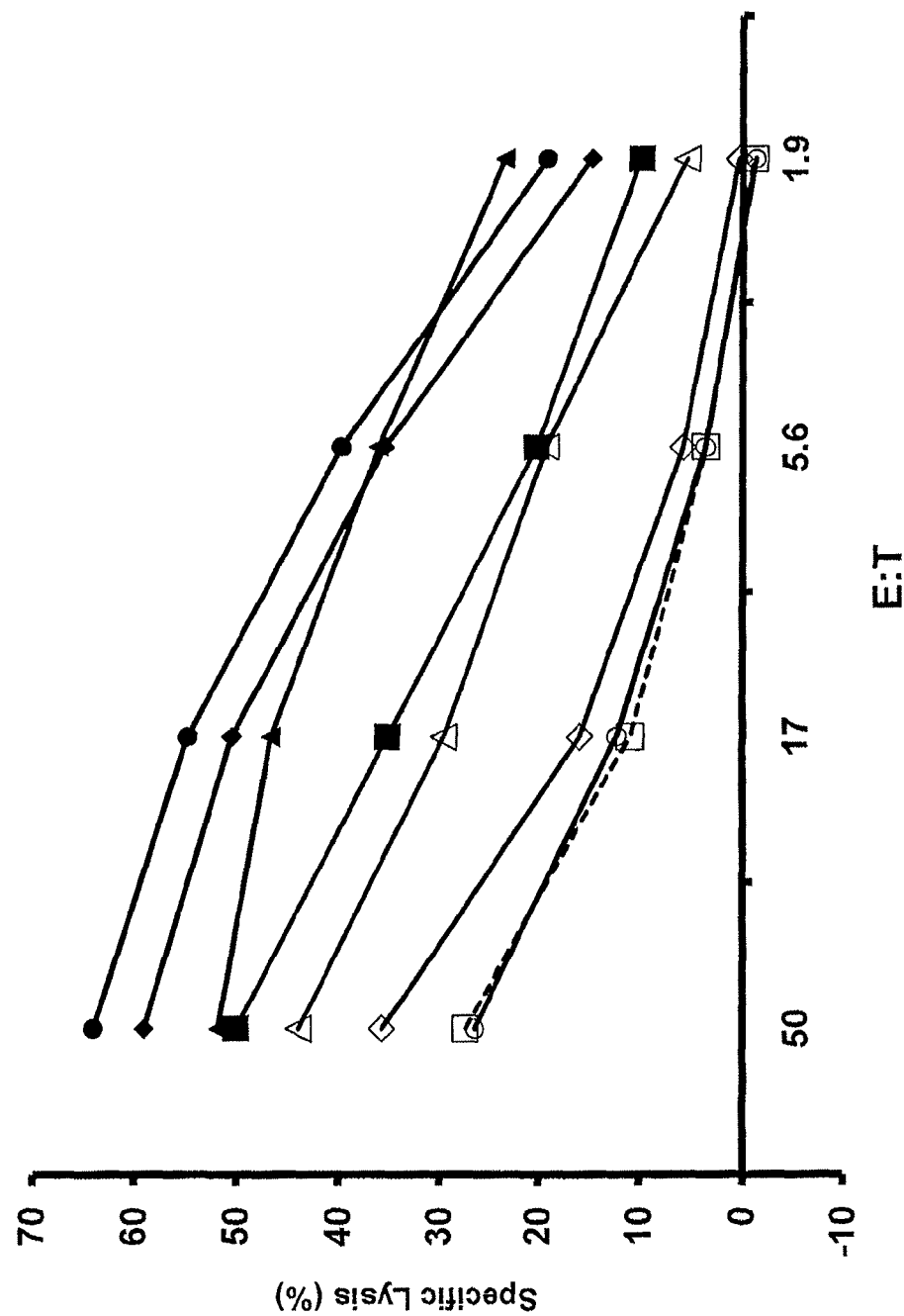
Figure 3:
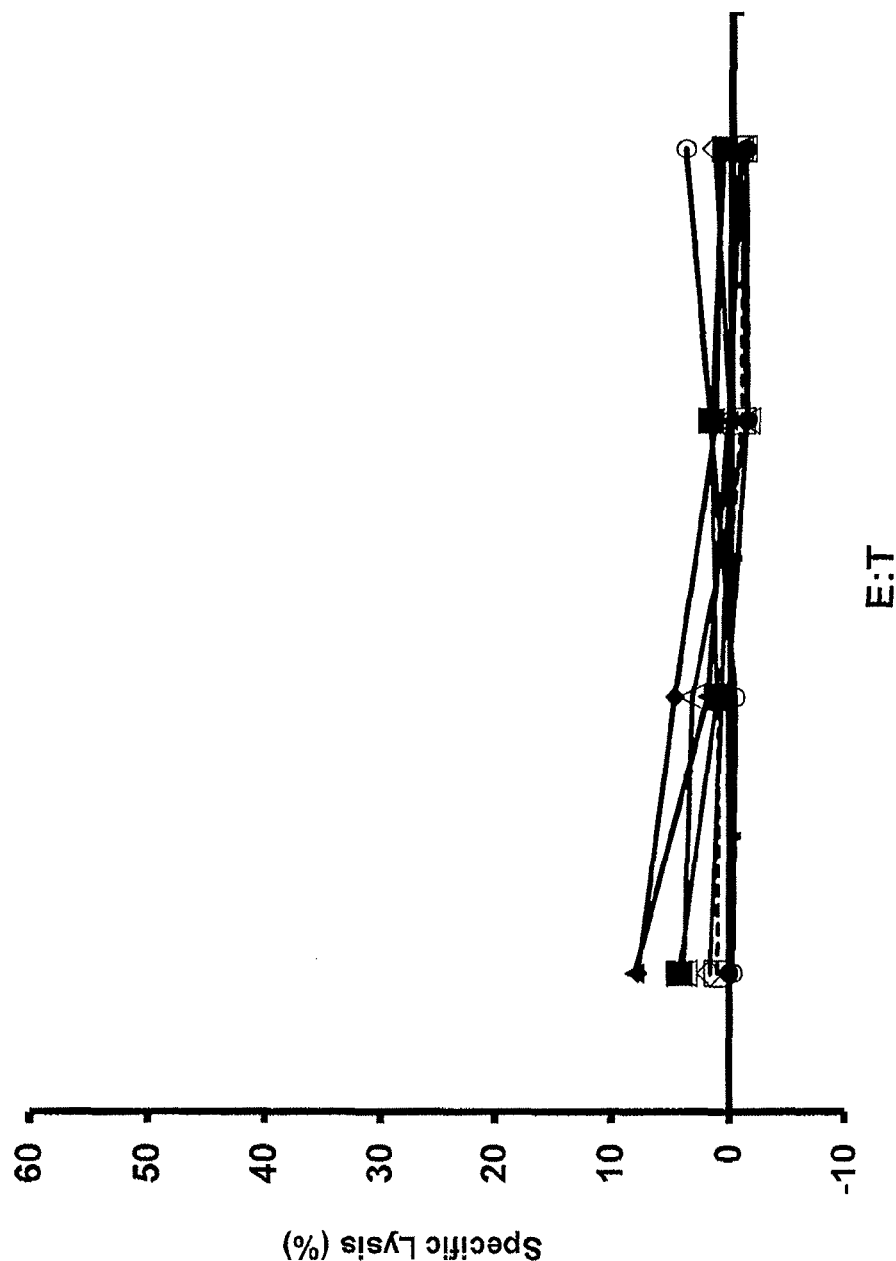
Figure 4:
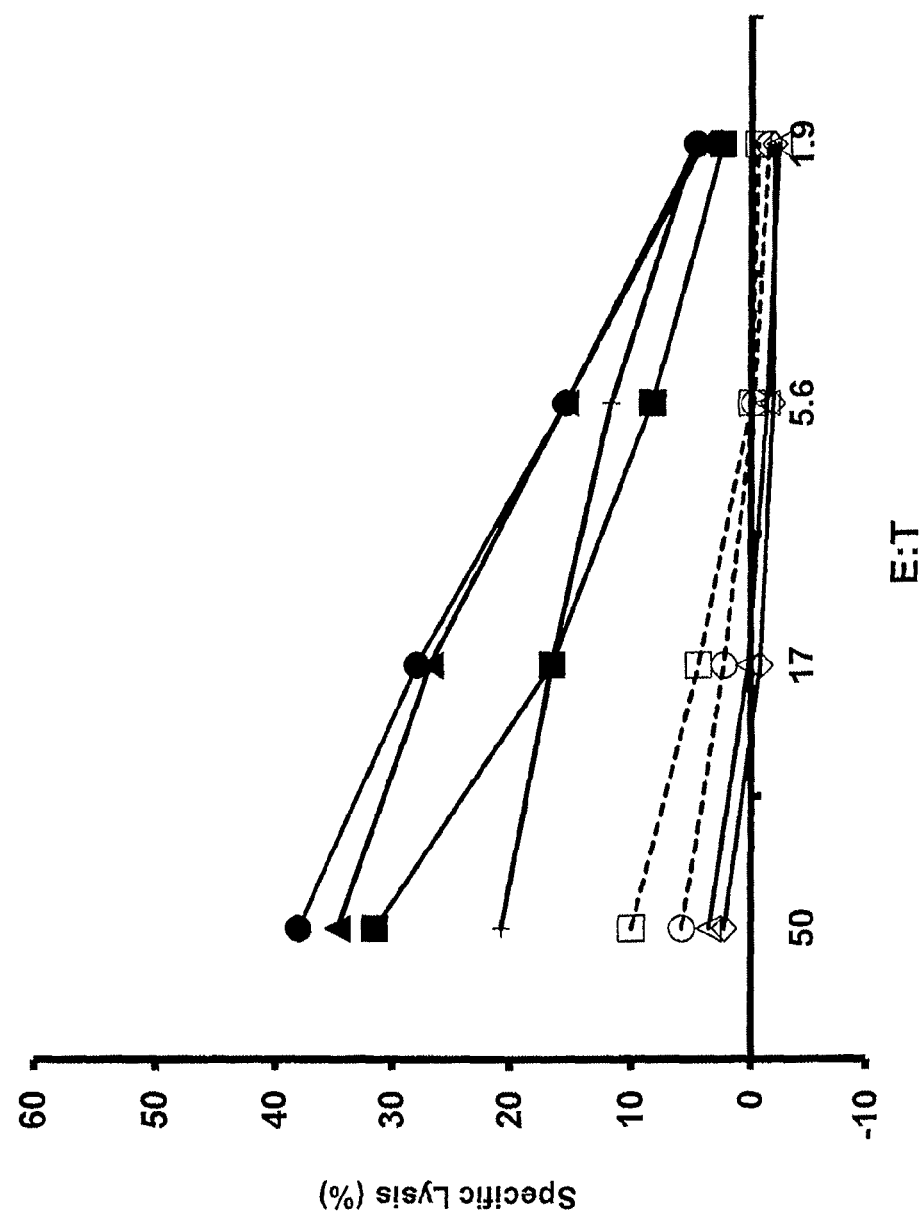
Figure 5:
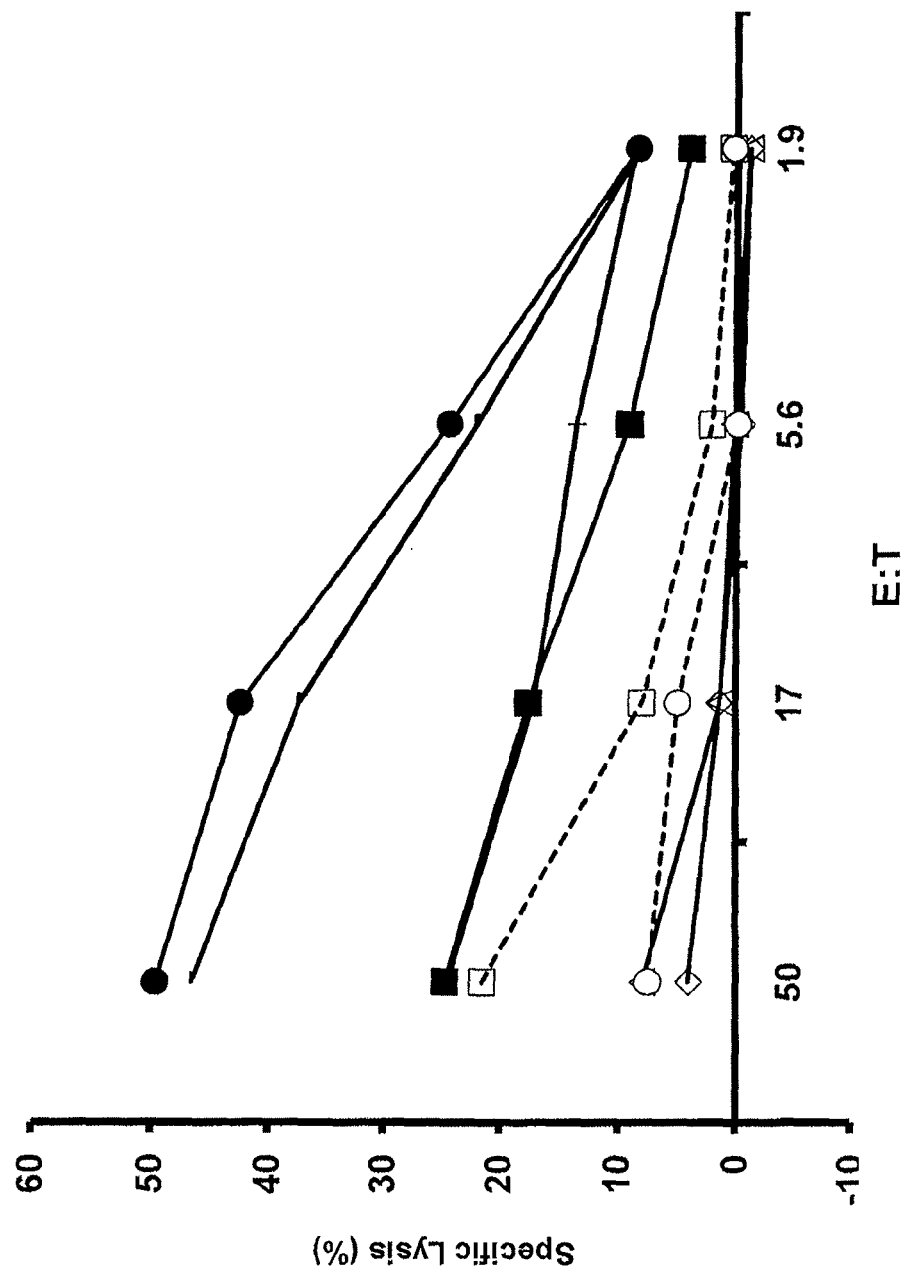
Figure 6:
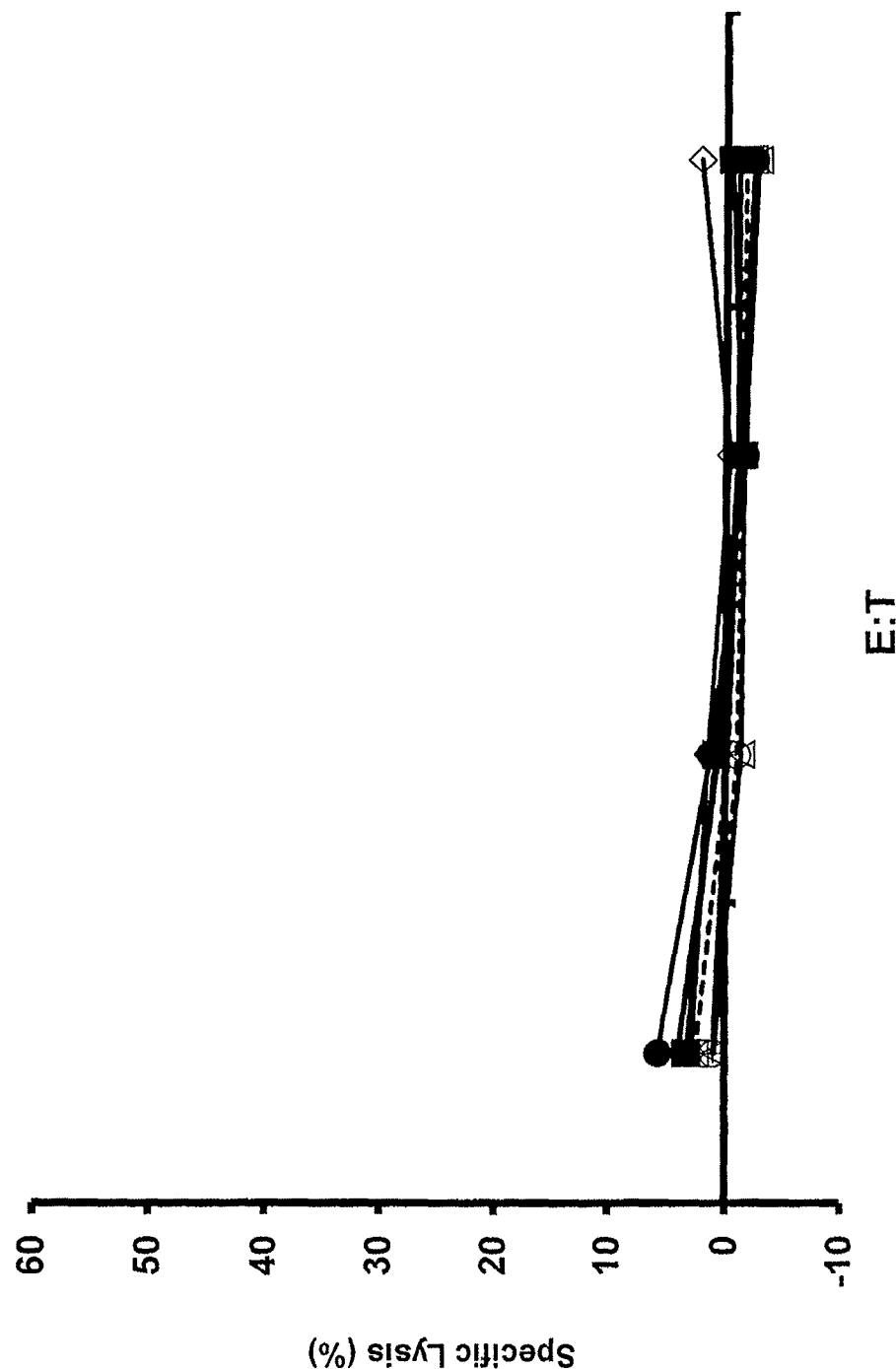

Target cells (526Mel, 624Mel, and 888Mel) were incubated with Chromium 51 (Cr-51) for 2 hours and then co-cultured with varying concentrations (effector to target ratios of 50, 17, 5.6, and 1.9) of transduced, sorted PBLs. After 4 hours, the supernatant was placed onto lumagen plates (Lumagen, Inc.) and dried overnight. Cytolysis was measured as the amount of Cr-51 released into the supernatant. The results are shown in FIGS. 1-3 (Donor A) and FIGS. 4-6 (Donor B).

This example demonstrated the ability of PBLs transduced with unmodified tyrosinase TCR or murine-human chimera tyrosinase TCR to specifically lyse melanoma cells as compared to cells transduced with MART-1 F4 TCR or gp100 TCR.

Example 14

This example demonstrates that glioma cells are reactive to tyrosinase TCRs.

Four HLA-A2 glioma cell lines (SNB 75, U251, SF-539, SNB-19) were cultured with varying levels of IFN-γ (0.5 ng, and 10 ng) and then co-cultured with PBLs transduced with GFP (control), gp100, unmodified tyrosinase TCR (comprising SEQ ID NOs: 11 and 12), TRP-2 TCR, MAGE TCR, and MART-1 TCR transduced PBLs as described in Example 6. One control melanoma cell line (624mel) was cultured with no IFN-γ and then co-cultured with GFP, gp100 TCR unmodified tyrosinase TCR, TRP-2 TCR, MAGE TCR, and MART-1 TCR transduced PBLs as described in Example 6.

Glioma cell line SNB 75 was reactive to tyrosinase TCR and gp100 TCR transduced PBLs at each tested IFN-γ concentration, but was not reactive to GFP, MAGE TCR, or MART-1 TCR transduced PBLs at any tested IFN-γ concentration. Glioma cell lines U251, SF-539, SNB-19 were not reactive to GFP, gp100 TCR, unmodified tyrosinase TCR, TRP-2 TCR, MAGE TCR, or MART-1 TCR transduced PBLs at any tested IFN-γ concentration. Control melanoma cell line 624Mel was reactive to gp100 TCR, unmodified tyrosinase TCR, TRP-2 TCR, and MART-1 TCR transduced PBLs.

This example demonstrated that glioma cell line SNB 75 is reactive to tyrosinase TCRs.

Example 15

Western blotting was performed to determine tyrosinase expression in glioma cell lines. Four HLA-A2 glioma cell lines (SNB 75, U251, SF-539, SNB-19), one control melanoma cell line (624mel), and one negative control cell line (COS-ESO) were lysed and protein was extracted. After equilibrating protein concentration, Western blotting was performed to determine tyrosinase protein expression.

The Western blot revealed that all four glioma cell lines (SNB 75, U251, SF-539, SNB-19) and 624mel expressed tyrosinase, although the glioma cell lines expressed tyrosinase to a lesser degree than the melanoma cell line 624mel.

This example demonstrated that tyrosinase is expressed in glioma cell lines.

Example 16

FACS analysis was performed to determine tyrosinase expression in glioma cell lines. The four glioma cell lines and one melanoma cell line of Example 15 were permeabilized and intracellular FACS staining was performed using an anti-tyrosinase antibody.

The FACS analysis revealed that all four glioma cell lines (SNB 75, U251, SF-539, SNB-19) and 624mel expressed tyrosinase.

This example demonstrated that tyrosinase is expressed in glioma cell lines.

Example 17

This example demonstrates the biological activity of mouse splenocytes transduced with retroviral vectors encoding the TCRs of Examples 2, 3, 4, and 5.

Mouse splenocytes were untransduced or were transduced with GFP (control), the unmodified tyrosinase TCR of Example 2 (encoding SEQ ID NOs: 11 and 12), the cysteine-substituted tyrosinase TCR of Example 3 (encoding SEQ ID NOs: 16 and 17), the murine-human chimera tyrosinase TCR of Example 4 (encoding SEQ ID NOs: 20 and 21), or the cysteine-substituted murine-human chimera tyrosinase TCR of Example 5 (encoding SEQ ID NOs: 24 and 25). The cells were transduced once or twice as described in Example 6. TCR was detected on the cell surface by FACS analysis using CD8 antibody and Vβ antibody staining.

Biological activity of the transduced cells was assessed by co-culturing with target cells and measuring IFN-γ secretion. Untransduced and transduced splenocytes were cultured alone (media) or co-cultured as described in Example 6 with 526Mel, 624Mel, 888Mel, B16 mouse melanoma line (B16), or B16 cells transduced to express human HLA-A2 (B16 A2). The supernatant was removed and the IFN-γ level (pg/ml) was determined as described in Example 6. The results are shown in Tables 11 (transduced once) and 12 (transduced twice).

TABLE 11

|  | Untransduced (pg/ml) | GFP (pg/ml) | Unmodified Tyr TCR (pg/ml) | Cysteine-substituted Tyr TCR (pg/ml) | Murine-human chimera Tyr TCR (pg/ml) | Cysteine - substituted murine-human chimera Tyr TCR (pg/ml) |
| --- | --- | --- | --- | --- | --- | --- |
| Media | 273 | 0 | 430 | 628 | 651 | 0 |
| 526Mel | 866 | 541 | 50141 | 15735 | 175119 | 151248 |
| 624Mel | 772 | 205 | 68562 | 32751 | 189528 | 188533 |
| 888Mel | 3035 | 2196 | 2978 | 2323 | 3510 | 1260 |
| B16 A2 | 6569 | 5579 | 75858 | 36552 | 184073 | 182608 |
| B16 | 4080 | 4476 | 6139 | 6219 | 6910 | 5292 |

TABLE 12

|  | Untransduced (pg/ml) | GFP (pg/ml) | Unmodified Tyr TCR (pg/ml) | Cysteine-substituted Tyr TCR (pg/ml) | Murine-human chimera Tyr TCR (pg/ml) | Cysteine - substituted murine-human chimera Tyr TCR (pg/ml) |
| --- | --- | --- | --- | --- | --- | --- |
| Media | 562 | 268 | 661 | 358 | 475 | 339 |
| 526Mel | 1553 | 451 | 52600 | 20440 | 139854 | 142313 |
| 624Mel | 1120 | 70 | 94088 | 43218 | 162328 | 168073 |
| 888Mel | 3275 | 983 | 4700 | 2271 | 4504 | 2271 |
| B16 A2 | 7610 | 5814 | 88809 | 39863 | 155307 | 139936 |
| B16 | 4669 | 5228 | 8478 | 6703 | 8155 | 6523 |

As can be seen in Tables 11 and 12, mouse splenocytes transduced with murine-human chimera tyrosinase TCR, cysteine-substituted murine-human chimera tyrosinase TCR, unmodified tyrosinase TCR, or cysteine-substituted tyrosinase TCR demonstrate higher reactivity than untransduced cells or cells transduced with GFP when co-cultured with 526Mel, 624Mel, or B16 A2 cells.

This example demonstrated the biological activity of mouse splenocytes transduced with retroviral vectors encoding unmodified and modified TCRs.

Example 18

This example demonstrates the biological activity of PBLs transduced with a retroviral vector encoding the unmodified Tyr TCR (SEQ ID NOs: 11 and 12).

The biological activity of the unmodified anti-tyrosinase TCR was compared to another CD8-independent TCR, anti-gp100:154-162, which has demonstrated objective clinical responses in melanoma patients. As target cells, tumor digests were prepared from resected melanomas as previously described (Romeo, M. J., et al. Clin. Cancer Res. 12:2463-2467 (2006)). Patient derived tumor cells used as targets were acquired from surgically resected lesions, which were digested overnight in enzymes until a single-cell suspension was obtained. Patient tumors were chosen for their tyrosinase, gp100, and HLA-A2 expression as determined by immunohistochemical analysis. The tumor from patient 1 had >75% of cells expressing both gp100 and tyrosinase and was HLA-A2+. The tumor from patient 2 had >75% tyrosinase positive cells, <5% gp100 positive cells and was HLA-A2+. The tumor from patient 3 had no tyrosinase or gp100 expression and was HLA-A2+. Finally, the tumor from patient 4 had >75% of cells expressing tyrosinase and gp100, but was HLA-A2 negative.

Untransduced PBL or PBL transduced with unmodified Tyr TCR (Example 2) or gp100 TCR were co-cultured overnight with tumor digests. Supernatants were harvested and interferon gamma (IFN-G) was measured by colorimetric ELISA (Endogen, Cambridge, Mass.). The results are shown in Table 13.

TABLE 13

|  | Patient 1 (IFN-γ (pg/ml)) | Patient 2 (IFN-γ (pg/ml)) | Patient 3 (IFN-γ (pg/ml)) | Patient 4 (IFN-γ (pg/ml)) |
| --- | --- | --- | --- | --- |
| Untransduced | 0 | 0 | 0 | 0 |
| unmodified Tyr TCR | 62500 | 30000 | 0 | 0 |
| gp100 TCR | 15000 | 0 | 0 | 0 |

As shown in Table 13, overnight co-culture with tumor digests revealed greater IFN-G release with anti-tyrosinase TCR compared to anti-gp100:154-162 TCR transduced PBL. Digests that failed to express the target antigen or HLA-A2 elicited no response.

Lysis was assessed by radioactivity of supernatant following co-culture of $^{51}$Cr labeled tumor targets with effectors for 4 hours as previously described (Topalian, S. L. et al. J. Immunol. 142:3714-3725 (1989)). The anti-tyrosinase TCR transduced PBL demonstrated a higher percentage lysis of the tumor digests compared to the anti-gp100:154-162 TCR transduced PBL at the same E:T ratio (37% vs. 15% for Patient 1 and 35% vs. 9% for Patient 2, each at a 17:1 effector to target ratio). PBL from Patients 3 and 4 elicited no response.

The anti-tyrosinase TCR (SEQ ID NOs: 11 and 12) was also compared to the previously reported high affinity anti-MART-1 (DMF5 clone) TCR vector (Johnson, L. A., et al. J. Immunol. 177:6548-6559 (2006)). This particular vector was identified by screening 24 MART-1 reactive TIL clones and was chosen for its high avidity against peptide and tumor targets. Identical gamma-retroviral vector preparations were produced for the three vectors (anti-MART-1, anti-gp100:154-162, and unmodified anti-tyrosinase TCR (SEQ ID NO: 39)) and used to transduce PBL using the same protocol and subsequently co-cultured with melanoma cell lines (526Mel, 624Mel, 888Mel, and 938Mel). Supernatants were harvested and IFN-γ was measured by colorimetric ELISA (Endogen, Cambridge, Mass.). The results are shown in Table 14.

TABLE 14

|  | 526Mel (IFN-γ (pg/ml)) | 624Mel (IFN-γ (pg/ml)) | 888Mel (IFN-γ (pg/ml)) | 938Mel (IFN-γ (pg/ml)) |
| --- | --- | --- | --- | --- |
| MART-1 TCR | 14900 | 11000 | 0 | 0 |
| GP100 TCR | 23000 | 12500 | 0 | 0 |
| Unmodified Tyr TCR | 32500 | 42500 | 0 | 0 |

As shown in Table 14, unmodified anti-tyrosinase TCR transduced cells displayed superior reactivity compared to the MART-1 and gp100:154-162 TCR vectors.

This example demonstrated that cells transduced with a nucleic acid encoding an unmodified Tyr TCR exhibit higher tumor reactivity than cells that were transduced with a nucleic acid encoding a MART-1 TCR or a gp100 TCR.

Example 19

This example demonstrates that cells transduced with unmodified anti-tyrosinase TCR (SEQ ID NOs: 11 and 12) mediate in vivo tumor regression.

All animal experiments were approved by the NIH Animal Ethics Committee. Mice were separated into 4 groups receiving: 1) irradiation alone, 2) vaccine and IL-2, 3) adoptive cell transfer (ACT) with untransduced splenocytes, vaccine and IL-2 and 4) ACT with unmodified anti-tyrosinase TCR (SEQ ID NOs: 11 and 12) transduced splenocytes, vaccine, and IL-2. HLA-A*0201/K$^b$ transgenic mice at 6 to 12 weeks were injected with 5×10$^5$ B16/A2/K$^b$ tumor cells in PBS 2 weeks prior to ACT. Mice were irradiated with 500 cGy and then separated into 4 groups of 5 mice per group. Cells were administered by tail vein injection (TVI) (10× 10$^6$) in 200 µl of PBS. For mice receiving vaccine, 2×10$^7$ PFU of recombinant fowlpox virus expressing human tyrosinase was given by TVI. All mice except those in the untreated group were given 30,000 IU of rhIL-2 intraperitoneally twice per day for 3 days. Measurements were done using a caliper by a blinded investigator. Mice were sacrificed when tumors reached 300 m$^2$, or at the discretion of the veterinary staff at NIH.

Tumor size was measured on the day of treatment and every three days after until 2 groups had less than three mice. Tumor size and survival were plotted to compare growth and survival between the groups. The results are shown in FIGS. 7A-7B.

Figure 7:
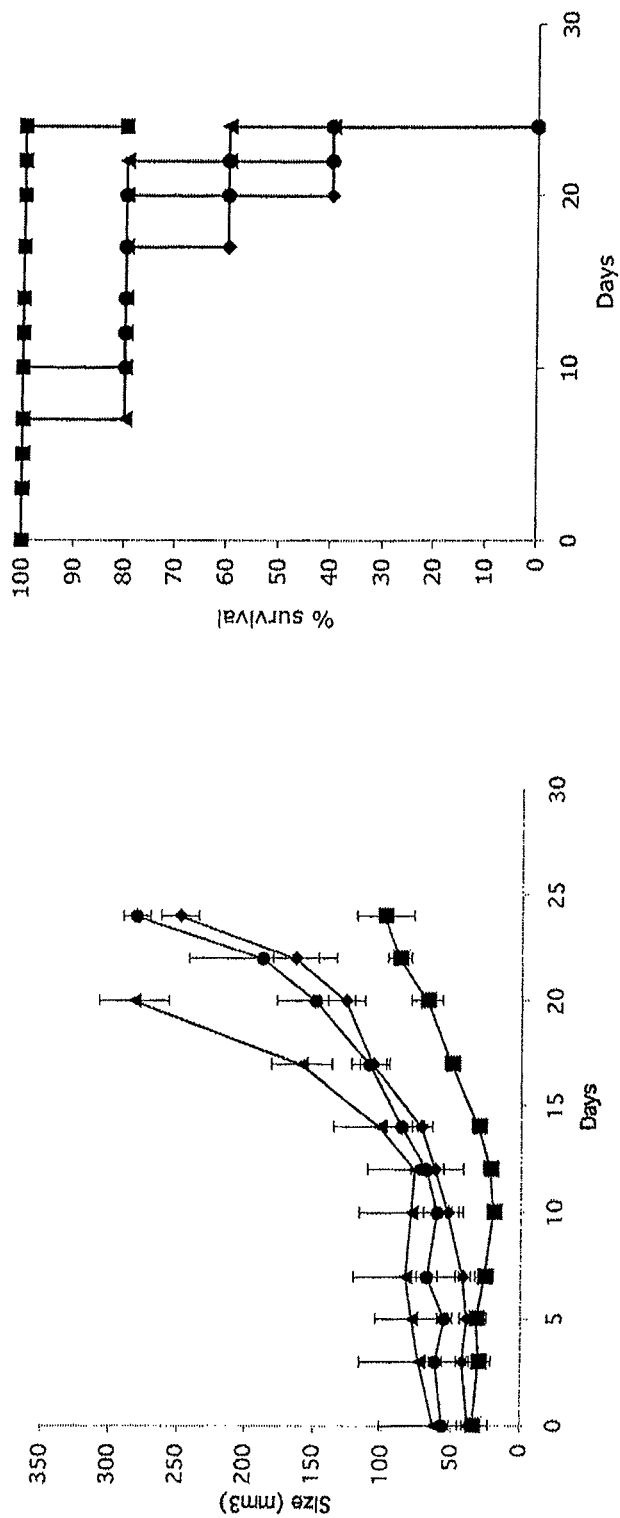
FIG. 7A is a graph of the tumor size (mm$^3$) of B16/A2 Kb tumor-bearing mice at days following irradiation only (♦), vaccine and IL-2 alone (▲), adoptive cell transfer (ACT) with untransduced splenocytes with IL-2 and vaccine (●), and ACT with unmodified anti-tyrosinase TCR transduced splenocytes with vaccine and IL-2 (■).
FIG. 7B is a graph of survival (%) of B16/A2 Kb tumor-bearing mice at days following irradiation only (♦), vaccine and IL-2 alone (▲), adoptive cell transfer (ACT) with untransduced splenocytes with IL-2 and vaccine (●), and ACT with unmodified anti-tyrosinase TCR transduced splenocytes with vaccine and IL-2 (■).

Mice receiving splenocytes transduced with the unmodified anti-tyrosinase TCR demonstrated greater tumor regression and delayed growth compared to mice treated with untransduced cells (p<0.05) (FIG. 7A). There was no difference seen between ACT with untransduced cells and irradiation alone. The group receiving vaccine alone and IL-2 appeared to do slightly worse, although this was not statistically significant. Survival among mice treated with the anti-tyrosinase TCR (SEQ ID NOs: 11 and 12) was 80% at the end of the experiment compared to 0% in the group receiving untransduced cells (FIG. 7B).

To further analyze the in vivo anti-tumor activity of this TCR, transduced murine splenocytes were separated into CD8 and CD4 T cells following transduction with the anti-tyrosinase TCR vector (SEQ ID NO: 39). B16/A2 Kb tumor bearing mice were given 500 rads irradiation on day 0 of cell transfer. All mice, except the irradiation only group, also received $2\times10^7$ pfu of rVVhTYR vaccine and 100,000 CU/ml of rhIL-2 bid ×3.

Figure 8:
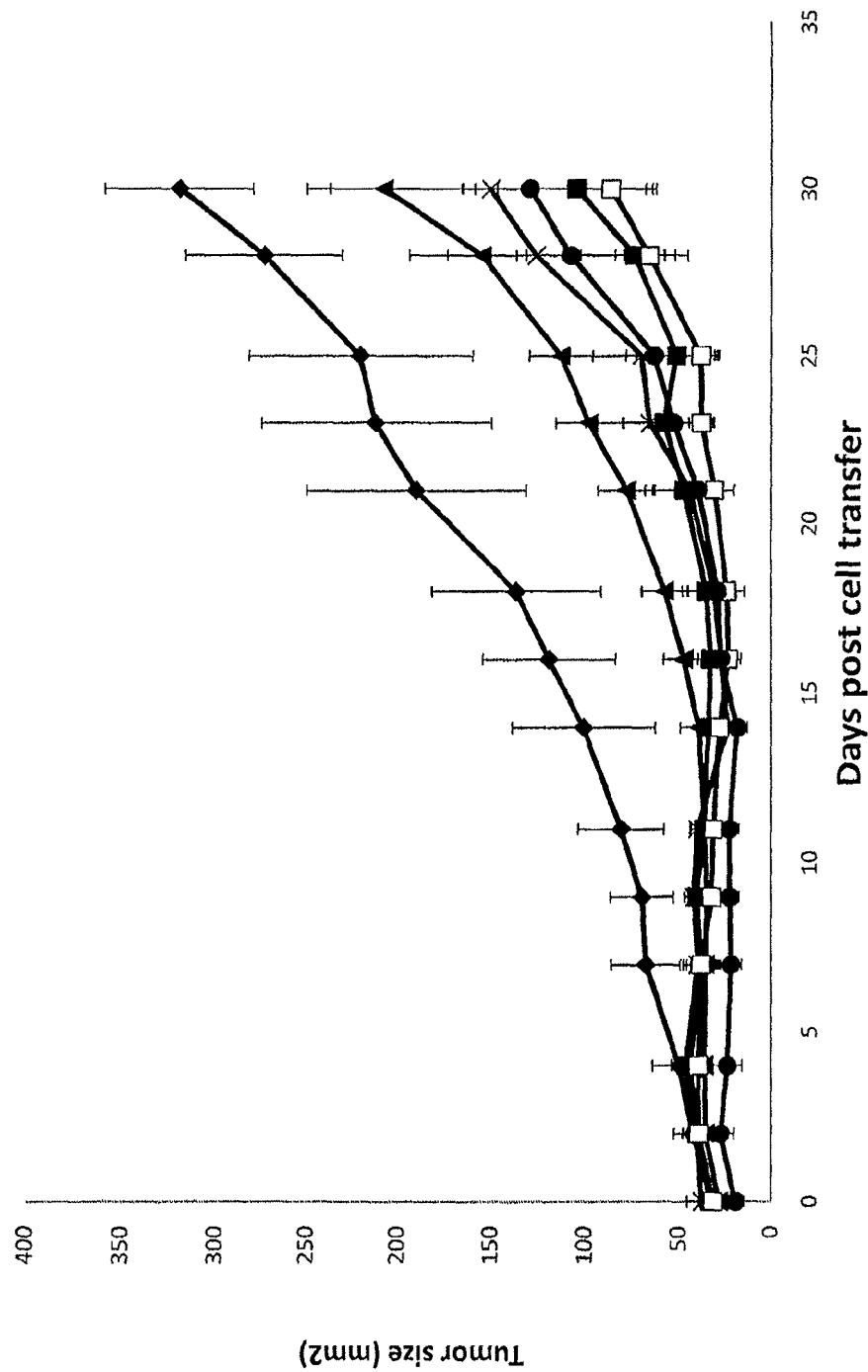
FIG. 8 is a graph of the tumor size (mm$^2$) of B16/A2 Kb tumor-bearing mice at days following irradiation only (▲) or adoptive cell transfer of unmodified anti-tyrosinase TCR transduced splenocytes (1×10$^7$ CD4 (■), 1×10$^6$ CD4 (▲), 2×10$^6$ CD8 (X), 1×10$^7$ CD8 (□), or 1×10$^7$ CD4 and CD8 (●)).
Figure 9:
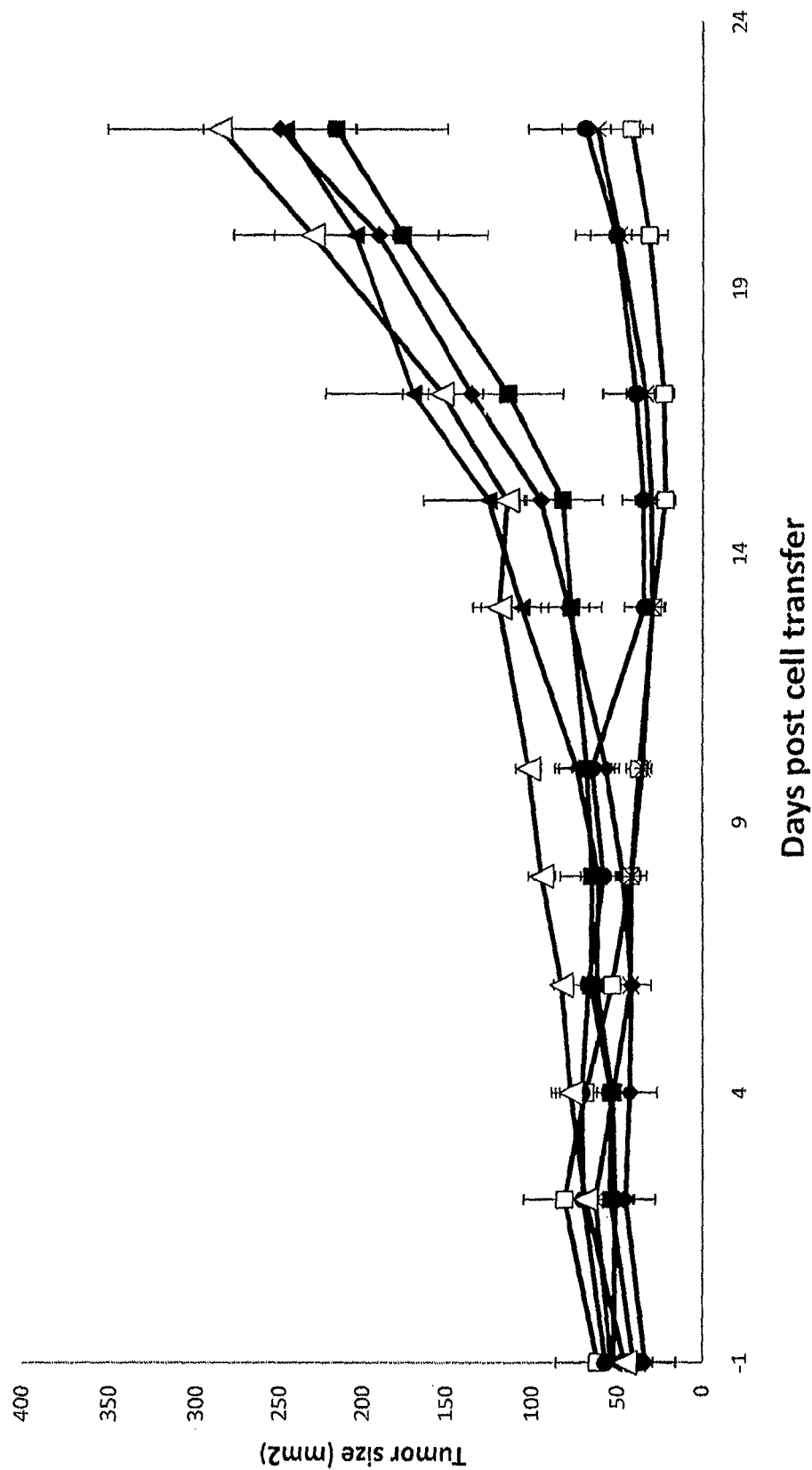
FIG. 9 is a graph of the tumor size (mm$^2$) of B16/A2 Kb tumor-bearing mice at days following irradiation only (Δ) or adoptive cell transfer of unmodified anti-tyrosinase TCR transduced splenocytes (CD8 (X), CD4 (□), or CD4 and CD8 (●)) or untransduced splenocytes (CD4 (♦), CD8 (■), or CD4 and CD8 (▲)).

With respect to FIG. 8, animals bearing established tumors were administered anti-tyrosinase transduced CD8, CD4, or CD4+ CD8 T cells ($1\times10^7$ CD4, $1\times10^6$ CD4, $2\times10^6$ CD8, $1\times10^7$ CD8, $1\times10^7$ CD4, or $1\times10^7$ CD8) (5 mice per group) and tumor growth followed. With respect to FIG. 9, animals bearing established tumors were administered anti-tyrosinase transduced CD8, CD4, or CD4+ CD8 T cells ($1\times10^7$) (5 mice per group) and tumor growth followed.

All groups treated with anti-tyrosinase TCR (SEQ ID NOs: 11 and 12) engineered cells demonstrated statistically significant (p<0.05) delay in tumor growth. In two independent experiments (FIGS. 8 and 9), we observed equal tumor treatment with all three groups; there was no statistical difference between animals receiving both CD4 and CD8 T cells versus the animals that received CD8 or CD4 T cells alone.

This example demonstrated that cells transduced with unmodified anti-tyrosinase TCR (SEQ ID NOs: 11 and 12) improve survival and mediate in vivo tumor regression in tumor-bearing mice, and that this tumor regression is CD4/CD8 independent.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A TCR comprising the amino acid sequences of SEQ ID NOs: 1-6 and 14-15.

2. The TCR of claim 1, comprising the amino acid sequences of SEQ ID NOs: 16-17.

3. A TCR comprising the amino acid sequences of SEQ ID NOs: 1-6 and 22-23.

4. The TCR of claim 3, comprising the amino acid sequences of SEQ ID NOs: 24-25.

5. A pharmaceutical composition comprising the TCR of claim 3 and a pharmaceutically acceptable carrier.

6. An isolated or purified polypeptide comprising the amino acid sequences of:
   (i) SEQ ID NOs: 1-6 and 14-15; or
   (ii) SEQ ID NOs: 1-6 and 22-23.

7. The isolated or purified polypeptide of claim 6, comprising the amino acid sequences of:
   (i) SEQ ID NOs: 7-8 and 14-15;
   (ii) SEQ ID NOs: 55, 8, and 14-15;
   (iii) SEQ ID NOs: 7-8 and 22-23; or
   (iv) SEQ ID NOs: 55, 8, and 22-23.

8. The isolated or purified polypeptide of claim 6, comprising the amino acid sequences of:
   (i) SEQ ID NOs: 16 and 17; or
   (ii) SEQ ID NOs: 24 and 25.

9. An isolated or purified protein comprising at least one of the polypeptides of claim 6.

10. An isolated or purified protein comprising:
    (i) a first polypeptide chain comprising the amino acid sequences of SEQ ID NOs: 1-3 and 14 and a second polypeptide chain comprising the amino acid sequences of SEQ ID NOs: 4-6 and 15; or
    (ii) a first polypeptide chain comprising the amino acid sequences of SEQ ID NOs: 1-3 and 22 and a second polypeptide chain comprising the amino acid sequences of SEQ ID NOs: 4-6 and 23.

11. The isolated or purified protein of claim 10, comprising a first polypeptide chain comprising the amino acid sequences of SEQ ID NOs: 7 and 14 and a second polypeptide chain comprising the amino acid sequences of SEQ ID NOs: 8 and 15.

12. The isolated or purified protein of claim 10, comprising a first polypeptide chain comprising the amino acid sequences of SEQ ID NOs: 55 and 14 and a second polypeptide chain comprising the amino acid sequences of SEQ ID NOs: 8 and 15.

13. The isolated or purified protein of claim 10, comprising a first polypeptide chain comprising the amino acid sequences of SEQ ID NOs: 7 and 22 and a second polypeptide chain comprising the amino acid sequences of SEQ ID NOs: 8 and 23.

14. The isolated or purified protein of claim 10, comprising a first polypeptide chain comprising the amino acid sequences of SEQ ID NOs: 55 and 22 and a second polypeptide chain comprising the amino acid sequences of SEQ ID NOs: 8 and 23.

15. The isolated or purified protein of claim 10, comprising a first polypeptide chain comprising the amino acid sequence of SEQ ID NO: 16 and a second polypeptide chain comprising the amino acid sequence of SEQ ID NO: 17.

16. The isolated or purified protein of claim 10, comprising a first polypeptide chain comprising the amino acid sequence of SEQ ID NO: 24 and a second polypeptide chain comprising the amino acid sequence of SEQ ID NO: 25.

17. A pharmaceutical composition comprising the TCR of claim 1 and a pharmaceutically acceptable carrier.

18. A pharmaceutical composition comprising the TCR of claim 1 and a pharmaceutically acceptable carrier.

19. A pharmaceutical composition comprising the TCR of claim 4 and a pharmaceutically acceptable carrier.

20. A pharmaceutical composition comprising the polypeptide of claim 6 and a pharmaceutically acceptable carrier.

21. A pharmaceutical composition comprising the protein of claim 10 and a pharmaceutically acceptable carrier.

\* \* \* \* \*